(12) United States Patent
Kennedy-Smith et al.

(10) Patent No.: US 7,713,974 B2
(45) Date of Patent: May 11, 2010

(54) NON-NUCLEOSIDE REVERSE TRANSCRIPTASE INHIBITORS

(75) Inventors: Joshua Kennedy-Smith, San Francisco, CA (US); Wylie Solang Palmer, Mountain View, CA (US); Zachary Kevin Sweeney, Redwood City, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 26 days.

(21) Appl. No.: 11/893,349

(22) Filed: Aug. 15, 2007

(65) Prior Publication Data
US 2008/0045511 A1 Feb. 21, 2008

Related U.S. Application Data

(60) Provisional application No. 60/838,272, filed on Aug. 16, 2006.

(51) Int. Cl.
| | |
|---|---|
| C07D 487/04 | (2006.01) |
| A61K 31/4985 | (2006.01) |
| A61P 31/18 | (2006.01) |
| C07D 231/20 | (2006.01) |
| C07D 231/12 | (2006.01) |
| C07D 231/56 | (2006.01) |
| A61K 31/415 | (2006.01) |
| A61K 31/407 | (2006.01) |
| A61K 31/519 | (2006.01) |
| C07D 471/04 | (2006.01) |

(52) U.S. Cl. ............... 514/248; 544/236; 544/262; 544/350; 514/407; 514/406; 514/303; 514/262.1; 514/249; 548/370.4; 548/362.5; 548/375.1; 546/119

(58) Field of Classification Search ............ 544/236; 514/248
See application file for complete search history.

(56) References Cited

U.S. PATENT DOCUMENTS 7,166,738 B2  1/2007  Dunn et al.

(Continued)

FOREIGN PATENT DOCUMENTS

| WO | WO 02/04424 A1 | 1/2002 |
|---|---|---|
| WO | WO 02/30907 A1 | 4/2002 |
| WO | WO 02/085860 A1 | 10/2002 |
| WO | WO 02/100853 A1 | 12/2002 |
| WO | WO 2004/029042 A1 | 4/2004 |
| WO | WO 2004/029051 A1 | 4/2004 |
| WO | WO 2004/031156 A1 | 4/2004 |
| WO | WO 2004/031178 A1 | 4/2004 |
| WO | WO 2004/085411 A1 | 10/2004 |
| WO | WO 2005/090317 A1 | 9/2005 |

| WO | WO 2006/067587 A2 | 6/2006 |
|---|---|---|

OTHER PUBLICATIONS

Chan, J. H. et. al., "Novel Benzophenones as Non-nucleoside Reverse Transcriptase Inhibitors of HIV-1," *J. Med Chem.* 2004, vol. 47, pp. 1175-1182.

(Continued)

*Primary Examiner*—James O Wilson
*Assistant Examiner*—Cecilia M Jaisle
(74) *Attorney, Agent, or Firm*—Brian L. Buckwalter

(57) ABSTRACT

The present invention provides for compounds useful for treating an HIV infection, or preventing an HIV infection, or treating AIDS or ARC. The compounds of the invention are of formula I wherein A is A1, A2, A3 or A4 and $R^1$, $R^2$, $R^3$, $R^{4a}$, $R^{4b}$, $R^5$, $R^6$, Ar, $X^1$, $X^2$, $X^4$, $X^4$ and $X^5$ are as herein defined. Also disclosed in the present invention are methods of treating an HIV infection with compounds defined herein and pharmaceutical compositions containing said compounds.

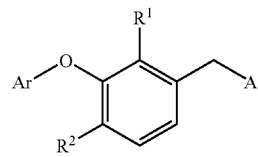

I

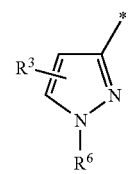

A1

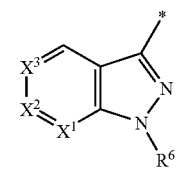

A2

A3

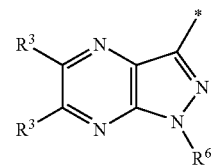

A4

7 Claims, No Drawings

U.S. PATENT DOCUMENTS

| | | |
|---|---|---|
| 7,189,718 B2 | 3/2007 | Dunn et al. |
| 7,208,509 B2 | 4/2007 | Dunn et al. |
| 7,241,794 B2 | 7/2007 | Dunn et al. |
| 2005/0054707 A1 | 3/2005 | Edwards et al. |
| 2005/0215554 A1 | 9/2005 | Dunn et al. |
| 2005/0239880 A1 | 10/2005 | Dunn et al. |
| 2006/0025462 A1 | 2/2006 | Dunn et al. |
| 2006/0069261 A1 | 3/2006 | Bonneau et al. |
| 2006/0223874 A1 | 10/2006 | Martin et al. |
| 2007/0021442 A1 | 1/2007 | Saggar et al. |
| 2007/0078128 A1 | 4/2007 | Saito et al. |
| 2007/0088015 A1 | 4/2007 | Silva et al. |
| 2007/0088053 A1 | 4/2007 | Mirzadegan et al. |

OTHER PUBLICATIONS

Genin, M. J., et. al., "Novel 1,5-Diphenylpyrazole Nonnucleoside HIV-1 Reverse Transcriptase Inhibitors with Enhanced Activity versus the Delavirdine-Resistant P236L Mutant: Lead Identification and SAR of 3- and 4-Substituted Derivatives," *Journal Med. Chem.* 2000, vol. 43, pp. 1034-1040.

Romines, K. R., et. al., "Structure-Activity Relationship Studies of Novel Benzophenones leading to the Discovery of a Potent, Next Generation HIV Nonnucleoside Reverse Transcriptase Inhibitors," *J. Med. Chem.* 2006, vol. 49, pp. 727-739.

Wyatt, P. G. et. al., "Benzophenone Derivatives: A Novel Series of Potent and Selective Inhibitors of Human Immunodeficiency Virus Type 1 Reverse Transcriptase," *Journal Med. Chem.* 1995, vol. 38, pp. 1657-1665.

NON-NUCLEOSIDE REVERSE TRANSCRIPTASE INHIBITORS

CROSS REFERENCE TO PRIOR APPLICATIONS

This application is claims benefit of U.S. Provisional Application No. 60/838,272, filed Aug. 16, 2006, which is hereby incorporated by reference in its entirety.

FIELD OF THE INVENTION

The invention relates to the field of antiviral therapy and, in particular, to non-nucleoside compounds that inhibit HIV reverse transcriptase and are useful for treating Human Immunodeficiency Virus (HIV) mediated diseases. The invention provides novel pyrazole compounds according to formula I, for treatment or prophylaxis of HIV mediated diseases, AIDS or ARC, employing said compounds in monotherapy or in combination therapy.

BACKGROUND OF THE INVENTION

The human immunodeficiency virus HIV is the causative agent of acquired immunodeficiency syndrome (AIDS), a disease characterized by the destruction of the immune system, particularly of the $CD4^+$ T-cell, with attendant susceptibility to opportunistic infections. HIV infection is also associated with a precursor AIDS—related complex (ARC), a syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two crucial viral enzymes: HIV protease and HIV reverse transcriptase. (J. S. G. Montaner et al., *Antiretroviral therapy: 'the state of the art'*, Biomed & Pharmacother. 1999 53:63-72; R. W. Shafer and D. A. Vuitton, *Highly active retroviral therapy (HAART) for the treatment of infection with human immunodeficiency virus type*, Biomed. & Pharmacother. 1999 53:73-86; E. De Clercq, *New Developments in Anti-HIV Chemotherap. Curr. Med. Chem.* 2001 8:1543-1572). Two general classes of RTI inhibitors have been identified: nucleoside reverse transcriptase inhibitors (NRTI) and non-nucleoside reverse transcriptase inhibitors. Currently the CCR5 co-receptor has emerged as a potential target for anti-HIV chemotherapy (D. Chantry, *Expert Opin. Emerg. Drugs* 2004 9(1):1-7; C. G. Barber, *Curr. Opin. Invest. Drugs* 2004 5(8):851-861; D. Schols, *Curr. Topics Med. Chem.* 2004 4(9):883-893; N. A. Meanwell and J. F. Kadow, *Curr. Opin. Drug Discov. Dev.* 2003 6(4):451-461).

NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate-binding site on the HIV reverse transcriptase thereby altering the shape of the active site or blocking polymerase activity (R. W. Buckheit, Jr., *Non-nucleoside reverse transcriptase inhibitors: perspectives for novel therapeutic compounds and strategies for treatment of HIV infection*, Expert Opin. Investig. Drugs 2001 10(8)1423-1442; E. De Clercq, *The role of non-nucleoside reverse transcriptase inhibitors (NNRTIs) in the therapy of HIV infection*, Antiviral Res. 1998 38:153-179; E. De Clercq, *New Developments in Anti-HIV Chemotherapy*, Current medicinal Chem. 2001 8(13):1543-1572; G. Moyle, *The Emerging Roles of Non-Nucleoside Reverse Transcriptase Inhibitors in Antiviral Therapy*, Drugs 2001 61 (1): 19-26). Although over thirty structural classes of NNRTIs have been identified in the laboratory, only three compounds have been approved for HIV therapy: efavirenz, nevirapine and delavirdine.

Initially viewed as a promising class of compounds, in vitro and in vivo studies quickly revealed the NNRTIs presented a low barrier to the emergence of drug resistant HIV strains and class-specific toxicity. Drug resistance frequently develops with only a single point mutation in the RT. While combination therapy with NRTIs, PIs and NNRTIs has, in many cases, dramatically lowered viral loads and slowed disease progression, significant therapeutic problems remain. (R. M. Gulick, *Eur. Soc. Clin. Microbiol. and Inf. Dis.* 2003 9(3):186-193) The cocktails are not effective in all patients, potentially severe adverse reactions often occur and the rapidly reproducing HIV virus has proven adroit at creating mutant drug-resistant variants of wild type protease and reverse transcriptase. There remains a need for safer drugs with activity against wild type and commonly occurring resistant strains of HIV.

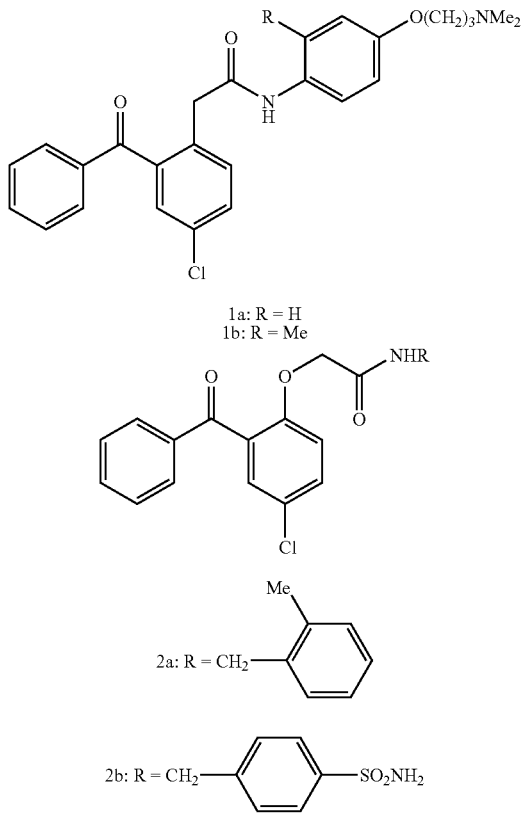

1a: R = H
1b: R = Me

2a: R = CH₂—
2b: R = CH₂—

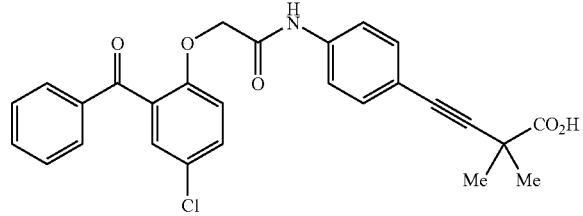

2-Benzoyl phenyl-N-[phenyl]-acetamide compounds 1a and 1b have been shown to inhibit HIV-1 reverse transcriptase (P. G. Wyatt et al., *J. Med. Chem.* 1995 38(10):1657-1665). Further screening identified related compounds, e.g. 2-benzoyl phenyloxy-N-[phenyl]-acetamide, 2a, and a sulfonamide derivative 2b which also inhibited reverse transcriptase (J. H. Chan et al., *J. Med Chem.* 2004 47(5):1175-1182; K. R Romines et al., *J. Med. Chem.* 2006 49(2): 727-739; C. L. Webster et al., WO01/17982). P. Bonneau et al. in US 20060069261 published Mar. 30, 2006 disclose 4-{4-[2-(2-benzoyl-phenoxy)-acetylamino]-phenyl}-2,2-dimethyl-but-3-ynoic acid compounds 3 which are inhibitors of HIV reverse transcriptase.

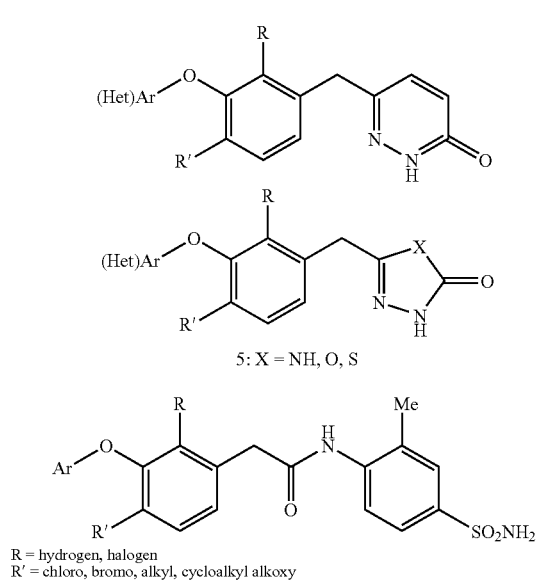

R = hydrogen, halogen
R′ = chloro, bromo, alkyl, cycloalkyl alkoxy

Pyridazinone non-nucleoside reverse transcriptase inhibitors 4 have been described by J. P. Dunn et al. in U. S. Publication 20040198736, filed Mar. 23, 2004 and by J. P. Dunn et al. in U. S. Publication No. 2005021554 filed Mar. 22, 2005. 5-Aralkyl-2,4-dihydro-[1,2,4]triazol-3-one, 5-aralkyl-3H-[1,3,4]oxadiazol-2-one and 5-aralkyl-3H-[1,3,4]thiadiazol-2-one non-nucleoside reverse transcriptase inhibitors 5 have been disclosed by J. P. Dunn et al. in U. S. Publication No. 20040192704 filed Mar. 23, 2004 and by J. P. Dunn et al. in U. S. Publication No. 20060025462 filed Jun. 27, 2005. Related compounds are disclosed by Y. D. Saito et al. in U.S. Ser. No. 60/722,335. Phenylacetamide non-nucleoside reverse transcriptase inhibitors 6 have been disclosed by J. P. Dunn et al. in U.S. Pub. No. 20050239881 published Oct. 27, 2005 and methods for treating retroviral infection with phenylacetamide compounds have been disclosed by J. P. Dunn et al. in U. S. Publication No. 20050239880 published Oct. 27, 2005; T. Mirzadegan and T. Silva in U.S. Ser. No. 60/728,443 filed Oct. 19, 2005; and Z. K. Sweeney and T. Silva in U.S. Ser. No 60/728,609 Oct. 19, 2005. These applications are hereby incorporated by reference in their entirety.

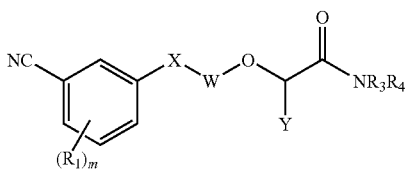

In WO2006/067587 published Jun. 26, 2006, L. H. Jones et al. disclose biaryl ether derivatives 7 and compositions containing them which bind to the enzyme reverse transcriptase and are modulators, especially inhibitors, thereof.

Pyrazole compounds which inhibit HIV reverse transcriptase have been disclosed. L. H. Jones et al. in WO2002085860 published Oct. 31, 2002 entitled "Preparation of aryloxy pyrazole derivatives as reverse transcriptase inhibitors for treating HIV", H. L. Jones et al. in WO2004031178 published Apr. 15, 2008 entitled "Preparation of pyrazole amides for treating HIV infections", D. A. Price et al. in WO2004031178 published Apr. 15, 2004, entitled "Preparation of pyrazole derivatives as HIV reverse transcriptase inhibitors", P. J. Edwards et al in WO2004031178 published Apr. 15, 2004 entitled "Preparation of pyrazole derivatives as therapeutic agents for HIV mediated diseases", O. Barba and L. H. Jones in WO2004029042 published Apr. 8, 2004, WO20040408 entitled "Preparation of pyrazole derivatives as reverse transcriptase inhibitors" and R. G. Corbau et al. in WO 2002004424 published Jan. 17, 2002 entitled "Pyrazole derivatives useful as reverse transcriptase inhibitor, for the treatment of HIV infection, and their use, formulations, and preparation" all disclose pyrazole compounds which inhibit HIV reverse transcriptase.

B. W. Dymock et al. in WO2002100853 published Dec. 12, 2002 entitled "Preparation of pyrazoles as HIV reverse transcriptase inhibitors" and J. Dunn et al. in WO 2004074257 publish Sep. 2, 2004 entitled "Preparation of pyrazole derivatives as non-nucleoside reverse transcriptase inhibitors for the treatment of HIV disorders and compositions thereof" also disclose pyrazole compounds which inhibit HIV RT.

M. J. Genin et al. (*J. Med. Chem.* 2000 43(5):1034-1040) disclose pyrazole compounds with activity against the delaviradine resistant P236L mutant.

SUMMARY OF THE INVENTION

The present invention provides novel compounds which show potent activity against wild type and mutant HIV reverse transcriptase. The compounds of the present invention are particularly active against HIV-1 reverse transcriptase. The invention is comprised of a compound according to formula I

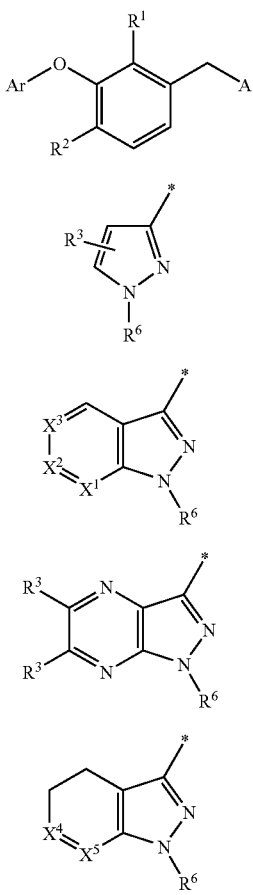

wherein:

A is selected from (i) A1, (ii) A2 wherein (a) $X^1$, $X^2$ and $X^3$ are independently $CR^3$, (b) one of $X^1$ and $X^2$ is N or N→O and the other of $X^1$ and $X^2$ along with $X^3$ are independently $CR^3$, (c) $X^1$ and one of $X^2$ or $X^3$ are N and the other of $X^2$ or $X^3$ is $CR^3$, (d) one of $X^1$ and $X^2$ is $NR^5$, the other of $X^1$ and $X^2$ is C(=O), $X^3$ is $CR^3$ and the bond between $X^1$ and $X^2$ is a single bond; (iii) A3, or (iv) A4 wherein one of $X^4$ and $X^5$ is $NR^5$, the other of $X^4$ and $X^5$ is C(=O);

$R^1$ is fluorine or hydrogen;

$R^2$ is hydrogen, halogen, $C_{1-6}$ alkyl, $C_{3-7}$ cycloalkyl, $C_{1-6}$ haloalkyl, $C_{1-6}$ alkoxy, or $C_{1-6}$ alkylsulfonyl;

Ar is phenyl substituted with one to three groups independently selected in each occurrence from the group consisting of hydrogen, halogen, cyano, $C_{1-6}$ alkyl, $C_{1-6}$ alkoxy, $C_{1-6}$ haloalkyl and $C_{3-7}$ cycloalkyl;

$R^3$ is independently selected in each occurrence from the group consisting of: (i) hydrogen, (ii) hydroxy, (iii) $C_{1-6}$ alkoxy, (iv) halogen, (v) $NR^{4a}R^{4b}$, (vi) $C_{1-6}$ acylamino, (vii) $C_{1-6}$ alkylsulfonylamino, (viii) cyano, (ix) nitro, (x) $NHNH_2$; and (xi) phenyl optionally substituted with one to three substituents independently selected from the group consisting of halogen, $C_{1-6}$ alkyl, $C_{1-6}$ alkoxy, cyano, nitro;

$R^{4a}$ and $R^{4b}$ are independently hydrogen or $C_{1-6}$ alkyl;

$R^5$ is hydrogen or $C_{1-3}$ alkyl;

$R^6$ is hydrogen or $C_{1-6}$ alkyl; and, pharmaceutically acceptable salt thereof.

Compounds of formula I are useful inhibitors of HIV reverse transcriptase and afford a method for prevention and treatment of HIV infections and the treatment of AIDS and/or ARC. HIV undergoes facile mutations of its genetic code resulting in strains with reduced susceptibility to therapy with current therapeutic options. The compounds of formula I are useful for treating patients infected with a strain of HIV with at least one mutation compared to wild type virus. The present invention also relates to compositions containing compounds of formula I useful for the prevention and treatment of HIV infections and the treatment of AIDS and/or ARC. The present invention further relates to compounds of formula I which are useful in mono therapy or combination therapy with other anti-viral agents.

DETAILED DESCRIPTION OF THE INVENTION

In one embodiment of the present invention there is provided a compound according to formula I wherein $R^1$, $R^2$, $R^3$, $R^{4a}$, $R^{4b}$, $R^5$, $R^6$, Ar, A1, A2, A3, A4, $X^1$, $X^2$, $X^4$, $X^4$, $X^5$, are as described herein above. The phrase "as defined herein above" refers to the broadest definition for each group as provided in the Summary of the Invention. In other embodiments provided below, substituents present in each embodiment which are not explicitly defined retain the broadest definition provided in the Summary of the Invention.

In one embodiment of the present invention there is provided a compound according to formula I wherein $R^2$ is hydrogen, halogen, $C_{1-6}$ alkyl, $C_{3-7}$ cycloalkyl, or $C_{1-6}$ alkoxy; and $R^1$, $R^3$, $R^{4a}$, $R^{4b}$, $R^5$, $R^6$, Ar, A1, A2, A3, A4, $X^1$, $X^2$, $X^4$, $X^4$, $X^5$, are as described herein.

In another embodiment of the present invention there is provided a compound according to formula I wherein A1 or A2.

In another embodiment of the present invention there is provided a compound according to formula I wherein A is A1.

In another embodiment of the present invention there is provided a compound according to formula I wherein A is A2 and $X^1$, $X^2$ and $X^3$ are independently $CR^3$.

In another embodiment of the present invention there is provided a compound according to formula I wherein A is A2, $X^1$, $X^2$ and $X^3$ are independently $CR^3$, $R^1$ is fluoro; $R^2$ is $C_{1-6}$ alkyl, $C_{1-6}$ alkoxy or halogen; $R^6$ is hydrogen and Ar is 3-cyano-phenyl optionally substituted with one or two groups independently selected from halogen, cyano and $C_{1-6}$ haloalkyl.

In another embodiment of the present invention there is provided a compound according to formula I wherein A is A2, $X^1$, $X^2$ and $X^3$ are independently $CR^3$, $R^1$ is fluoro; $R^2$ is bromo or chloro; $R^6$ is hydrogen and Ar is 3-cyano-phenyl optionally substituted with one or two groups independently selected from halogen, cyano and $C_{1-6}$ haloalkyl.

In another embodiment of the present invention there is provided a compound according to formula I wherein A is A2, one of $X^1$ or $X^2$ is N or N—O, the other of $X^1$ and $X^2$ along with $X^3$ are independently $CR^3$.

In another embodiment of the present invention there is provided a compound according to formula I wherein A is A2, one of $X^1$ or $X^2$ is N or N—O, the other of $X^1$ and $X^2$ along with $X^3$ are independently $CR^3$, $R^1$ is fluoro; $R^2$ is $C_{1-6}$ alkyl, $C_{1-6}$ alkoxy or halogen; $R^5$ and $R^6$ is hydrogen and Ar is 3-cyano-phenyl optionally substituted with one or two groups independently selected from halogen, cyano and $C_{1-6}$ haloalkyl.

In another embodiment of the present invention there is provided a compound according to formula I wherein A is A2, one of $X^1$ or $X^2$ is N or N—O, the other of $X^1$ and $X^2$ along with $X^3$ are independently $CR^3$, $R^1$ is fluoro; $R^2$ is $C_{1-6}$ alkyl, $C_{1-6}$ alkoxy or halogen; $R^5$ and $R^6$ is hydrogen and Ar is 3-cyano-phenyl optionally substituted with halogen, cyano or $C_{1-6}$ haloalkyl meta to the cyano substituent.

In another embodiment of the present invention there is provided a compound according to formula I wherein A is A2, one of $X^1$ or $X^2$ is N or N—O, the other of $X^1$ and $X^2$ along with $X^3$ are independently $CR^3$, $R^1$ is fluoro; $R^2$ is chloro or bromo; $R^5$ and $R^6$ is hydrogen and Ar is 3-cyano-phenyl optionally substituted with halogen, cyano or $C_{1-6}$ haloalkyl meta to the cyano substituent.

In another embodiment of the present invention there is provided a compound according to formula I wherein A is A2, one of $X^1$ or $X^2$ is $NR^5$, the other of $X^1$ or $X^2$ is C(=O), $X^3$ is $CR^3$ and the bond between $X^1$ and $X^2$ is a single bond.

In another embodiment of the present invention there is provided a compound according to formula I wherein A is A2, $X^1$ and $X^2$ are N and $X^3$ is $CR^3$.

In another embodiment of the present invention there is provided a compound according to formula I wherein A is A2, one $X^1$ and $X^2$ are N and $X^3$ is $CR^3$, $R^1$ is fluoro; $R^2$ is $C_{1-6}$ alkyl, $C_{1-6}$ alkoxy or halogen; $R^5$ and $R^6$ are hydrogen and Ar is 3-cyano-phenyl optionally substituted with halogen, cyano or $C_{1-6}$ haloalkyl meta to the cyano substituent.

In another embodiment of the present invention there is provided a compound according to formula I wherein A is A2, one $X^1$ and $X^2$ are N and $X^3$ is $CR^3$, $R^1$ is fluoro; $R^2$ is $C_{1-6}$ alkyl, $C_{1-6}$ alkoxy or halogen; $R^5$ and $R^6$ are hydrogen and Ar is 3-cyano-phenyl optionally substituted with halogen, cyano or $C_{1-6}$ haloalkyl meta to the cyano substituent.

In another embodiment of the present invention there is provided a compound according to formula I wherein A is A2, one $X^1$ and $X^2$ are N and $X^3$ is $CR^3$, $R^1$ is fluoro; $R^2$ is bromo or chloro; $R^5$ and $R^6$ are hydrogen and Ar is 3-cyano-phenyl optionally substituted with halogen, cyano or $C_{1-6}$ haloalkyl meta to the cyano substituent.

In another embodiment of the present invention there is provided a compound according to formula I wherein A is A2, $X^1$ and $X^3$ are N and $X^2$ is $CR^3$.

In another embodiment of the present invention there is provided a compound according to formula I wherein A is A3, $R^1$ is fluoro; $R^2$ is $C_{1-6}$ alkyl, $C_{1-6}$ alkoxy or halogen; and Ar is 3-cyano-phenyl optionally substituted with halogen, cyano or $C_{1-6}$ haloalkyl meta to the cyano substituent.

In another embodiment of the present invention there is provided a compound according to formula I wherein A is A3, $R^1$ is fluoro; $R^2$ is $C_{1-6}$ alkyl, $C_{1-6}$ alkoxy or halogen; $R^6$ is hydrogen and Ar is 3-cyano-phenyl optionally substituted with halogen, cyano or $C_{1-6}$ haloalkyl meta to the cyano substituent.

In another embodiment of the present invention there is provided a compound according to formula I wherein A is A4 and one of $X^4$ or $X^5$ is $NR^5$, the other of $X^4$ or $X^5$ is C(=O).

In still another embodiment of the present invention there is a compound selected from I-1 to I-63 in TABLE 1.

In yet another embodiment of the present invention there is provided a method for treating an HIV infection, or preventing an HIV infection, or treating AIDS or ARC, comprising administering to a host in need thereof a therapeutically effective amount of a compound according to formula I wherein $R^1$, $R^2$, $R^3$, $R^{4a}$, $R^{4b}$, $R^5$, $R^6$, Ar, A1, A2, A3, A4, $X^1$, $X^2$, $X^4$, $X^4$, $X^5$, are as described herein above.

In still yet another embodiment of the present invention there is provided a method for treating an HIV infection, or preventing an HIV infection, or treating AIDS or ARC, comprising co-administering to a host in need thereof a therapeutically effective amount of least one compound selected from the group consisting of HIV protease inhibitors, nucleoside reverse transcriptase inhibitors, non-nucleoside reverse transcriptase inhibitors, CCR5 antagonists and viral fusion inhibitors along with a compound according to formula I wherein $R^1$, $R^2$, $R^3$, $R^{4a}$, $R^{4b}$, $R^5$, $R^6$, Ar, A1, A2, A3, A4, $X^1$, $X^2$, $X^4$, $X^4$, $X^5$, are as described herein above.

In still yet another embodiment of the present invention there is provided a method for treating an HIV infection, or preventing an HIV infection, or treating AIDS or ARC, comprising co-administering to a host in need thereof a therapeutically effective amount of least one compound selected from the group consisting of zidovudine, lamivudine, didanosine, zalcitabine, stavudine, rescriptor, sustiva, viramune, efavirenz, nevirapine, delavirdine, saquinavir, ritonavir, nelfinavir, indinavir, amprenavir, and lopinavir and enfuvirtide along with a compound according to formula I wherein $R^1$, $R^2$, $R^3$, $R^{4a}$, $R^{4b}$, $R^5$, $R^6$, Ar, A1, A2, A3, A4, $X^1$, $X^2$, $X^4$, $X^4$, $X^5$, are as described herein above.

In another embodiment of the present invention there is provided a method for inhibiting HIV reverse transcriptase in a host infected with HIV comprising administering a compound according to formula I wherein $R^1$, $R^2$, $R^3$, $R^{4a}$, $R^{4b}$, $R^5$, $R^6$, Ar, A1, A2, A3, A4, $X^1$, $X^2$, $X^4$, $X^4$, $X^5$, are as described herein above.

In still another embodiment of the present invention there is provided a method for inhibiting HIV reverse transcriptase in a host infected with a strain of HIV expressing a reverse transcriptase with at least one mutation compared to wild type HIV comprising administering a compound according to formula I wherein $R^1$, $R^2$, $R^3$, $R^{4a}$, $R^{4b}$, $R^5$, $R^6$, Ar, A1, A2, A3, A4, $X^1$, $X^2$, $X^4$, $X^4$, $X^5$, are as described herein above.

In yet another embodiment of the present invention there is provided a method for inhibiting HIV reverse transcriptase in a host infected with a strain of HIV exhibits reduced susceptibility to efavirenz, nevirapine or delavirdine comprising administering a compound according to formula I wherein $R^1$, $R^2$, $R^3$, $R^{4a}$, $R^{4b}$, $R^5$, $R^6$, Ar, A1, A2, A3, A4, $X^1$, $X^2$, $X^4$, $X^4$, $X^5$, are as described herein above.

In another embodiment of the present invention there is provided a pharmaceutical composition comprising a compound according to formula I wherein $R^1$, $R^2$, $R^3$, $R^{4a}$, $R^{4b}$, $R^5$, $R^6$, Ar, A1, A2, A3, A4, $X^1$, $X^2$, $X^4$, $X^4$, $X^5$ and at least one carrier, excipient or diluent

DEFINITIONS

The phrase "a" or "an" entity as used herein refers to one or more of that entity; for example, a compound refers to one or more compounds or at least one compound. As such, the terms "a" (or "an"), "one or more", and "at least one" can Pbe used interchangeably herein.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term-(ar)alkyl refers to either an unsubstituted alkyl or an aralkyl group. The term (hetero)aryl or (het)aryl refers to either an aryl or a heteroaryl group. The term "(hetero)aromatic" refers to an aryl or a heteroaryl group.

"Optional" or "optionally" means that a subsequently described event or circumstance may but need not occur, and that the description includes instances where the event or circumstance occurs and instances in which it does not. For example, "optional bond" means that the bond may or may not be present, and that the description includes single, double, or triple bonds.

The phrase "optional bond" means that the bond may or may not be present, and that the description includes single, double, or triple bonds. If a substituent is designated to be a "bond" or "absent", the atoms linked to the substituents are then directly connected.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

A "stable" compound is a compound which can be prepared and isolated and whose structure and properties remain or can be made to remain essentially unchanged for a period of time sufficient to allow the use of the compound for the purposes described herein (e.g., therapeutic or prophylactic administration to a subject).

Unless expressly stated to the contrary, all ranges cited herein are inclusive. For example, a heterocyclic ring described as containing "1 to 4 heteroatoms" means the ring can contain 1, 2, 3 or 4 heteroatoms. It is also to be understood that any range cited herein includes within its scope all of the subranges within that range. Thus, for example, an aryl or a heteroaryl described as optionally substituted with "from 1 to 5 substituents" is intended to include as aspects thereof, any aryl optionally substituted with 1 to 4 substituents, 1 to 3 substituents, 1 to 2 substituents, 2 to 5 substituents, 2 to 4 substituents, 2 to 3 substituents, 3 to 5 substituents, 3 to 4 substituents, 4 to 5 substituents, 1 substituent, 2 substituents, 3 substituents, 4 substituents, and 5 substituents.

The term "acyl" as used herein denotes a group of formula —C(=O)R wherein R is hydrogen or lower alkyl as defined herein. $C_{1-3}$ acyl denotes an acyl group as defied herein wherein R is $C_{1-3}$ alkyl.

The term "acylamino" as used herein denotes a group of formula —NHC(=O)R wherein R is hydrogen or lower alkyl as defined herein The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons.

The terms "alkylsulfonylamino" and "arylsulfonylamino" as used herein denotes a group of formula —NR'S(=O)$_2$R wherein R is alkyl or aryl respectively, R' is hydrogen or $C_{1-3}$ alkyl, and alkyl and aryl are as defined herein.

The terms "amino", "alkylamino" and "dialkylamino" as used herein refer to —NH$_2$, —NHR and —NR$_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to NH$_2$(CH$_2$)$_n$—, RHN(CH$_2$)$_n$—, and R$_2$N(CH$_2$)$_n$— respectively wherein n is 1 to 10 and R is alkyl as defined above. "$C_{1-6}$ alkylamino" as used herein refers to an aminoalkyl wherein alkyl is $C_{1-6}$. The term "phenylamino" as used herein refers to —NHPh wherein Ph represents an optionally substituted phenyl group.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-5}$ cycloalkyl" as used herein refers to a cycloalkyl composed of 3 to 5 carbons in the carbocyclic ring.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" refers to an —O-alkyl wherein alkyl is $C_{1-10}$.

The term "cyano" as used herein refers to a carbon linked to a nitrogen by a triple bond, i.e., —C≡N. The term "nitro" as used herein refers to a group —NO$_2$.

The term "haloalkyl" as used herein denotes an unbranched or branched chain alkyl group as defined above wherein 1, 2, 3 or more hydrogen atoms are substituted by a halogen. "$C_{1-3}$ haloalkyl" as used herein refers to a haloalkyl composed of 1 to 3 carbons and 1-8 halogen substituents. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, difluoromethyl, 2,2-dichloroethyl, 3-bromopropyl or 2,2,2-trifluoroethyl.

The term "haloalkoxy" as used herein means a —O-haloalkyl group wherein haloalkyl is defined herein.

The term "halogen" or "halo" as used herein means fluorine, chlorine, bromine, or iodine.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. $C_{1-6}$ hydroxyalkyl refers to a $C_{1-6}$ alkyl group as herein defined wherein one to three hydrogen atoms on different carbon atoms is/are replaced by a hydroxyl groups.

The term "$C_{1-6}$ carboxyalkyl" as used herein refers to a $C_{1-6}$ alkyl group as herein defined wherein one or two hydrogen atoms on different carbon atoms is/are replaced by a hydroxyl groups. The group $NR^aR^b$ as used in claim 1 where $R^a$ is a carboxyalkyl group which includes, but is not limited to, the natural amino acids glycine, alanine, valine, leucine and isoleucine.

The terms "azetidine", "pyrrolidine", "piperidine" and "azepine" refer to a 4-, 5-, 6- or 7-membered cycloalkane respectively wherein one carbon atom is replaced by a nitrogen atom.

The term "aryl" as used herein denotes a phenyl ring which can optionally be substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group. The term "aryloxy" as used herein denotes an optionally substituted phenol.

The terms "aza-indazoles" refers generically to a fused pyrazole with one nitrogen atom at any position in the ring fused to the pyrazole (e.g., 1H-pyrazolo[3,4-c]pyridin-3-yl or a 1H-pyrazolo[3,4-b]pyridin-3-yl rings) and a "di-aza-indazoles" refers generically to a fused pyrazole with two nitrogen atoms at any positions in the fused ring (e.g., 1H-pyrazolo[3,4-d]pyrimidin-3-yl rings).

The term "inert organic solvent" or "inert solvent" means the solvent is inert under the conditions of the reaction being described in conjunction therewith. In the case of the reaction of benzaldoxime with base an inert solvent is one which neither has an acidic proton nor will react with trifluoronitrobenzene. Examples on inert solvents include ethereal solvents and hydrocarbons. The term "base" refers to an organic or inorganic base of sufficient strength to deprotonate the phenol II. Examples of such bases are numerous and well known in the art.

An acetic acid synthetic equivalent of an alkyl bromoacetate is an acetic acid derivative with a leaving group on the α-carbon which is capable of being displaced by a phenolate salt. While the reaction is exemplified herein with ethyl bromoacetate other esters could be utilized in analogously. The ester also could be replaced with an amide including the anilide derivatives described herein.

The term "wild type" as used herein refers to the HIV virus strain which possesses the dominant genotype which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system.

The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA. Recent progress in development of RTI and PI inhibitors have been reviewed: F. M. Uckun and O. J. D'Cruz, *Exp. Opin. Ther. Pat.* 2006 16:265-293; L. Menendez-Arias, *Eur. Pharmacother.* 2006 94-96 and S. Rusconi and O. Vigano, *Future Drugs* 2006 3(1):79-88.

Typical suitable NRTIs include zidovudine (AZT; RETROVIR®); didanosine (ddI; VIDEX®); zalcitabine (ddC; HIVID®); stavudine (d4T; ZERIT®); lamivudine (3TC; EPIVIR®); abacavir (ZIAGEN®); adefovir dipivoxil [bis (POM)-PMEA; PREVON®]; lobucavir (BMS-180194), a nucleoside reverse transcriptase inhibitor disclosed in EP-0358154 and EP-0736533; BCH-10652, a reverse transcriptase inhibitor (in the form of a racemic mixture of BCH-10618 and BCH-10619) under development by Biochem Pharma; emitricitabine [(−)-FTC] in development by Triangle Pharmaceuticals; β-L-FD4 (also called β-L-D4C and named β-L-2',3'-dicleoxy-5-fluoro-cytidene) licensed Vion Pharmaceuticals; DAPD, the purine nucleoside, (−)-β-D-2,6-diamino-purine dioxolane disclosed in EP-0656778 and licensed to Triangle Pharmaceuticals; and Iodenosine (FddA), 9-(2,3-dideoxy-2-fluoro-β-D-threo-pentofuranosyl) adenine, an acid stable purine-based reverse transcriptase inhibitor under development by U.S. Bioscience Inc.

Typical suitable NNRTIs include nevirapine (BI-RG-587; VIRAMUNE®); delaviradine (BHAP, U-90152; RESCRIPTOR®); efavirenz (DMP-266; SUSTIVA®); PNU-142721, a furopyridine-thio-pyrimidine under development by Pfizer; AG-1549 (formerly Shionogi # S-1153); 5-(3,5-dichlorophenyl)-thio-4-isopropyl-1-(4-pyridyl)methyl-1H-imidazol-2-ylmethyl carbonate disclosed in WO 96/10019; MKC-442 (1-(ethoxy-methyl)-5-(1-methylethyl)-6-(phenylmethyl)-(2, 4(1H,3H)-pyrimidinedione); and (+)-calanolide A (NSC-675451) and B, coumarin derivatives disclosed in U.S. Pat. No. 5,489,697; etravirine (TMC-125; 4-[6-amino-5-bromo-2-(4-cyano-phenylamino)-pyrimidin-4-yloxy]-3,5-dimethyl-benzonitrile) and DAPY (TMC278; 4-{4-[4-((E)-2-cyano-vinyl)-2,6-dimethyl-phenylamino]-pyrimidin-2-ylamino}-benzonitrile) by Tibotec-Virco and Johnson & Johnson; BILR-355 BS (12-ethyl-8-[2-(1-hydroxy-quinolin-4-yloxy)-ethyl]-5-methyl-11,12-dihydro-5H-1,5,10,12-tetraaza-dibenzo[a,e]cycloocten-6-one by Boehringer-Ingleheim; PHI-236 (7-bromo-3-[2-(2,5-dimethoxy-phenyl)-ethyl]-3,4-dihydro-1H-pyrido[1,2-a][1,3,5]triazine-2-thione) and PHI-443 (1-(5-bromo-pyridin-2-yl)-3-(2-thiophen-2-yl-ethyl)-thiourea) by Paradigm Pharmaceuticals.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN® as well as nonpeptide protease inhibitors e.g., VIRACEPT®.

Typical suitable PIs include saquinavir available in hard gel capsules as INVIRASE® and in soft gel capsules as FORTOVASE® from Roche; ritonavir (ABT-538) available as NORVIR—from Abbott Laboratories; Lopinavir (ABT-378) also available from Abbot; KALETRA®, is co-formulation lopinavir and a sub-therapeutic dose of ritonavir available from Abbott Laboratories; indinavir (MK-639) available as CRIXIVAN® from Merck & Co.; nelfnavir (AG-1343) available as VIRACEPT® from Agouron Pharmaceuticals, Inc.; amprenavir (141W94) available as AGENERASE® from Vertex Pharmaceuticals, Inc. and GSK; tipranavir (PNU-140690) available as APTIVUS® from BI; lasinavir (BMS-234475/CGP-61755) by BMS; BMS-2322623, an azapeptide under development by BMS as a 2nd-generation HIV-1 PI; GW-640385X (VX-385) under development in a collaboration between GSK and Vertex; AG-001859 in preclinical development by Agouron/Pfizer; SM-309515 under development by Sumitomo Pharmaceuticals.

Additional PIs in preclinical development include N-cycloalkylglycines by BMS, α-hydroxyarylbutanamides by Enanta Pharmaceuticals; α-hydroxy-γ-[[(carbocyclic- or heterocyclic-substituted)amino)carbonyl]alkanamide derivatives; γ-hydroxy-2-(fluoroalkylaminocarbonyl)-1-piperazinepentanamides by Merck; dihydropyrone derivatives and α- and β-amino acid hydroxyethylamino sulfonamides by Pfizer; and N-amino acid substituted L-lysine derivatives by Procyon. Entry of HIV into target cells requires CD-4 cell surface receptor and the CCR5 (M-tropic strains) and CXCR4 (T-tropic strains) chemokine co-receptors. Chemokine antagonize which block viral binding to the chemokines are useful inhibitors of viral infection. Takeda's identified TAK-779 as a potential CCR5 antagonist. (M. Shiraishi et al., *J. Med. Chem.* 2000 43(10):2049-2063; M. Babba et al. *Proc. Nat. Acad Sci. USA* 1999 96:5698-5703) and TAK-220 (C. Tremblay et al. *Antimicrob. Agents Chemother.* 2005 49(8): 3483-3485). WO0039125 (D. R. Armour et al.) and WO0190106 (M. Perros et al.) disclose heterocyclic compounds that are potent and selective CCR5 antagonists. Miraviroc (UK-427,857; MVC) has advanced by Pfizer to phase III clinical trials and show activity against HIV-1 isolates and laboratory strains (P. Dorr et al., *Antimicrob. Agents Chemother.* 2005 49(11):4721-4732; A. Wood and D. Armour, *Prog. Med. Chem.* 2005 43:239-271; C. Watson et al., *Mol. Pharm.* 2005 67(4):1268-1282; M. J. Macartney et al., 43$^{rd}$ *Intersci. Conf. Antimicrob. Agents Chemother.* Sep. 14-17, 2003, Abstract H-875). Schering has advanced Sch-351125 (SCH-C) into Phase I/II clinical studies and reported the advance of a more potent follow-up compound, Vicroviroc (Sch-417690, SCH-D) into Phase I studies. (S. W. McCrombie et al., WO00066559; B. M. Baroudy et al. WO00066558; A. Palani et al., *J. Med. Chem.* 2001 44(21): 3339-3342; J. R. Tagat et al., *J. Med. Chem.* 2001 44(21): 3343-3346; J. A. Esté, *Cur. Opin. Invest. Drugs* 2002 3(3): 379-383; J. M. Struzki et al. *Proc. Nat. Acad Sci. USA* 2001 98:12718-12723). Merck has disclosed the preparation of (2S)-2-(3-chlorophenyl)-1-N-(methyl)-N-(phenylsulfonyl) amino]-4-[spiro(2,3-dihydrobenzothiophene-3,4'-piperidin-1'-yl)butane S-oxide (1) and related derivatives with good affinity for the CCR5 receptor and potent-HIV activity. (P. E. Finke et al., *Bioorg. Med. Chem. Lett.,* 2001 11:265-270; P. E. Finke et al., *Bioorg. Med. Chem. Lett.,* 2001 11:2469-2475; P. E. Finke et al., *Bioorg. Med. Chem. Lett.,* 2001 11:2475-2479; J. J. Hale et al., *Bioorg. Med. Chem. Lett.,* 2001 11:2741-22745; D. Kim et al., *Bioorg. Med. Chem. Lett.,* 2001 11:3099-3102) C. L. Lynch et al. *Org Lett.* 2003 5:2473-2475; R. S. Veazey et al. *J. Exp. Med.* 2003198:1551-1562. GSK-873140 (ONO-4128, E-913, AK-602) was identified in a program initiated at Kumamoto University (K. Maeda et al. *J. Biol. Chem.* 2001 276:35194-35200; H. Nakata et al. *J. Virol.* 2005 79(4):2087-2096) and has been advanced to clinical trials. In WO00/166525; WO00/187839; WO02/076948; WO02/076948; WO02/079156, WO2002070749, WO2003080574, WO2003042178, WO2004056773, WO2004018425 Astra Zeneca disclose 4-amino piperidine compounds which are CCR5 antagonists. In U.S. Publication No. 20050176703 published Aug. 11, 2005, S. D. Gabriel and D. M. Rotstein disclosed heterocyclic CCR5 antagonist capable of prevent HIV cell entry. In U.S. Publication No. 20060014767 published Jan. 19, 2006, E. K. Lee et al. disclosed heterocyclic CCR5 antagonist capable of prevent HIV cell entry.

Attachment Inhibitors effectively block interaction between viral envelope proteins and chemokine receptors or CD40 protein._TNX-355 is a humanized IgG4 monoclonal antibody that binds to a conformational epitope on domain 2 of CD4. (L. C. Burkly et al., *J. Immunol.* 1992 149:1779-87) TNX-355 can inhibit viral attachment of CCR5-, CXCR4- and dual/mixed tropic HIV-1 strains. (E. Godofsky et al., In Vitro Activity of the Humanized Anti-CD4 Monoclonal Antibody, TNX-355, against CCR5, CXCR4, and Dual-Tropic Isolates and Synergy with Enfuvirtide, 45*th Annual Interscience Conference on Antimicrobial Agents and Chemotherapy (ICAAC).* Dec. 16-19, 2005, Washington DC. Abstract # 3844; D. Norris et al. TNX-355 in Combination with Optimized Background Regime (OBR) Exhibits Greater Antiviral Activity than OBR Alone in HIV-Treatment Experienced Patients, 45*th Annual Interscience Conference on Antimicrobial Agents and Chemotherapy (ICAAC).* Dec. 16-19, 2005, Washington DC. Abstract # 4020.).

Macromolecular therapeutics including antibodies, soluble receptors and biologically active fragments thereof have become an increasingly important adjunct to conventional low molecular weight drugs. (O. H. Brekke and I. Sandlie *Nature Review Drug Discov.* 2003 2:52-62; A. M. Reichert *Nature Biotech.* 2001 19:819-821) Antibodies with high specificity and affinity can be targeted at extra-cellular proteins essential for viral cell fusion. CD4, CCR5 and CXCR4 have been targets for antibodies which inhibit viral fusion.

V. Roschke et al. (Characterization of a Panel of Novel Human Monoclonal Antibodies that Specifically Antagonize CCR5 and Block HIV-1 Entry, 44*th Annual Interscience Conference on Antimicrobial Agents and Chemotherapy (ICAAC).* Oct. 29, 2004, Washington DC. Abstract # 2871) have disclosed monoclonal antibodies which bind to the CCR5 receptor and inhibit HIV entry into cells expressing the CCR5 receptor. L. Wu and C. R MacKay disclose in U.S. Ser. No 09/870,932 filed May 30, 2001 disclose monoclonal antibodies 5C7 and 2D7 which bind to the CCR5 receptor in a manner capable of inhibiting HIV infection of a cell. W. C. Olsen et al. (*J. Virol.* 1999 73(5):4145-4155) disclose monoclonal antibodies capable of inhibiting (i) HIV-1 cell entry, (ii) HIV-1 envelope-mediated membrane fusion, (iii) gp120 binding to CCR5 and (iv) CC-chemokine activity. Synergism between the anti-CCR5 antibody Pro140 and a low molecular weight CCR5 antagonists have been disclosed by Murga et al. (3rd IAS Conference on HIV Pathogenesis and Treatment, Abstract TuOa.02.06. Jul. 24-27, 2005, Rio de Janeiro, Brazil) Anti-CCR5 antibodies have been isolated which inhibit HIV-1 cell entry also have been disclosed by M. Brandt et al. in U.S. Ser. No. 11/394,439 filed Mar. 31, 2006.

FUZEON® (T-20, DP-178, pentafuside) is disclosed in U.S. Pat. No. 5,464,933. T-20 and an analog, T-1249, are analogs of HIV gp41 fragment which are effectively inhibit a conformational change required for HIV fusion. T-20 has been approved and is available from Roche and Trimeris. FUZEON is administered as a continuous sc infusion or injection in combination therapy with other classes of anti HIV drugs.

Other antiviral agents which may be useful in HIV therapy include hydroxyurea, ribavirin, IL-2, IL-12, pentafuside. Hydroyurea (Droxia), a ribonucleoside triphosphate reductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN® (aldesleukin) from Chiron Corp. as a lyophilized powder for IV infusion or sc administration. IL-12 is disclosed in WO96/25171 and is available from Roche and Wyeth Pharmaceuticals. Ribavirin, 1-β-D-ribofuranosyl-1H-1,2,4-triazole-3-carboxamide, is described in U.S. Pat. No. 4,211,771 and is available from ICN Pharmaceuticals.

Commonly used abbreviations include: acetyl (Ac), azobis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N, N-dimethylaminopyridine (DMAP), N,N-dimethylformamide (DMF), dimethyl sulfoxide (DMSO), (diphenylphosphino)ethane (dppe), (diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), equivalents (eq. or equiv.), diethyl ether ($Et_2O$), acetic acid (HOAc), 1-N-hydroxybenzotriazole (HOBt), high pressure liquid chromatography (HPLC), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-$BuMe_2Si$ (TBDMS), triethylamine (TEA or $Et_3N$), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), 1,1'-bis-thin layer chromatography (TLC), tetrahydrofuran (THF), trimethylsilyl or $Me_3Si$ (TMS), p-toluenesulfonic acid monohydrate (TsOH or pTsOH), 4-Me—$C_6H_4SO_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, Nomenclature in Organic Chemistry, IUPAC 1979 Pergamon Press, Oxford.).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

Examples of representative compounds encompassed by, and within the scope of, the present invention are provided in the following Table. These examples and preparations which follow are provided to enable those skilled in the art to more clearly understand and to practice the present invention. They should not be considered as limiting the scope of the invention, but merely as being illustrative and representative thereof.

The symbols "*" at the end of a bond or "------" drawn through a bond each refer to the point of attachment of a functional group or other chemical moiety to the rest of the molecule of which it is a part. Thus, for example:

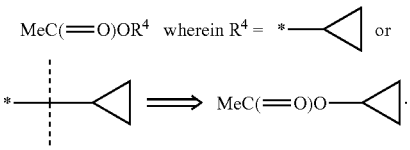

Compounds of formula I exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight.

TABLE 1

| Cpd # | NAME | mw | ms | mp |
|---|---|---|---|---|
| I-1 | 5-(4-Methyl-3-phenoxy-benzyl)-2H-pyrazol-3-ol | 280.3 | 281 | |
| I-2 | 3-[4-Chloro-3-(3-chloro-phenoxy)-benzyl]-1H-pyrazole | 319.2 | 318 | |
| I-3 | 3-Chloro-5-[6-chloro-2-fluoro-3-(1H-indazol-3-ylmethyl)-phenoxy]-benzonitrile | 412.3 | 411 | 163.3-163.7 |
| I-4 | 3-Chloro-5-[6-chloro-2-fluoro-3-(5-phenyl-1H-pyrazol-3-ylmethyl)-phenoxy]-benzonitrile | 438.3 | 437 | 148.0-150.1 |
| I-5 | 3-[6-Bromo-2-fluoro-3-(5-phenyl-1H-pyrazol-3-ylmethyl)-phenoxy]-5-difluoromethyl-benzonitrile | 498.3 | 497 | 78.3-90.1 |
| I-6 | 3-[6-Bromo-2-fluoro-3-(1H-indazol-3-ylmethyl)-phenoxy]-5-difluoromethyl-benzonitrile | 472.3 | 471 | |
| I-7 | 3-[6-Bromo-2-fluoro-3-(1H-pyrazolo[3,4-b]pyridin-3-ylmethyl)-phenoxy]-5-chloro-benzonitrile | 457.7 | 456 | 242-243 |
| I-8 | 3-[6-Bromo-2-fluoro-3-(7-oxy-1H-pyrazolo[3,4-b]pyridin-3-ylmethyl)-phenoxy]-5-chloro-benzonitrile | 473.7 | 474 | 215.7-219.3 |
| I-9 | 3-[6-Bromo-3-(6-chloro-1H-pyrazolo[3,4-b]pyridin-3-ylmethyl)-2-fluoro-phenoxy]-5-chloro-benzonitrile | 492.1 | 490 | 212.3-214 |
| I-10 | 3-[6-Bromo-2-fluoro-3-(6-hydrazino-1H-pyrazolo[3,4-d]pyrimidin-3-ylmethyl)-phenoxy]-5-chloro-benzonitrile; trifluoroacetic acid salt | 488.7 | 487 | |
| I-11 | 3-Chloro-5-[6-chloro-2-fluoro-3-(1H-pyrazolo[3,4-c]pyridazin-3-ylmethyl)-phenoxy]-benzonitrile | 414.2 | 413 | |
| I-12 | 3-[6-Bromo-2-fluoro-3-(6-oxo-6,7-dihydro-1H-pyrazolo[3,4-b]pyridin-3-ylmethyl)-phenoxy]-5-chloro-benzonitrile | 473.7 | 472 | |
| I-13 | 3-[6-Bromo-3-(6-chloro-1H-pyrazolo[3,4-d]pyrimidin-3-ylmethyl)-2-fluoro-phenoxy]-5-chloro-benzonitrile | 493.1 | 491 | 216.0-217.9 |
| I-14 | 3-[4-Bromo-3-(3-chloro-5-cyano-phenoxy)-2-fluoro-benzyl]-1H-pyrazolo[3,4-b]pyridine-6-carbonitrile | 482.7 | 481 | |
| I-15 | 3-[6-Bromo-2-fluoro-3-(1H-pyrazolo[3,4-c]pyridin-3-ylmethyl)-phenoxy]-5-chloro-benzonitrile | 457.7 | 456 | 182.0-186.9 |
| I-16 | 5-[6-Bromo-2-fluoro-3-(1H-pyrazolo[3,4-b]pyridin-3-ylmethyl)-phenoxy]-isophthalonitrile | 448.3 | 447 | 230.0-232.9 |
| I-17 | 3-[6-Bromo-2-fluoro-3-(1-methyl-1H-pyrazolo[3,4-b]pyridin-3-ylmethyl)-phenoxy]-5-chloro-benzonitrile | 471.7 | 470 | 138.6-142.6 |
| I-18 | 3-[6-Bromo-2-fluoro-3-(1H-pyrazolo[3,4-d]pyrimidin-3-ylmethyl)-phenoxy]-5-chloro-benzonitrile | 458.7 | 459 | 215.0-218.0 |
| I-19 | 5-[6-Bromo-2-fluoro-3-(1H-pyrazolo[3,4-c]pyridin-3-ylmethyl)-phenoxy]-isophthalonitrile | 448.3 | 447 | |
| I-20 | 3-[6-Bromo-2-fluoro-3-(7-nitro-1H-indazol-3-ylmethyl)-phenoxy]-5-chloro-benzonitrile | 501.7 | 500 | 214.2-216.0 |
| I-21 | 5-[6-Cyclopropyl-2-fluoro-3-(1H-pyrazolo[3,4-b]pyridin-3-ylmethyl)-phenoxy]-isophthalonitrile | 409.4 | 409 | 221.0-223.6 |
| I-22 | 3-[6-Bromo-2-fluoro-3-(6-methoxy-1H-pyrazolo[3,4-b]pyridin-3-ylmethyl)-phenoxy]-5-chloro-benzonitrile | 487.7 | 486 | 223.8-225.0 |
| I-23 | 3-[6-Bromo-2-fluoro-3-(5-fluoro-1H-pyrazolo[3,4-b]pyridin-3-ylmethyl)-phenoxy]-5-chloro-benzonitrile | 475.7 | 474 | 206.5-209.0 |
| I-24 | 3-Chloro-5-[2-fluoro-6-methyl-3-(1H-pyrazolo[3,4-b]pyridin-3-ylmethyl)-phenoxy]-benzonitrile | 392.8 | 392 | 215.0-218.8 |
| I-25 | 3-Chloro-5-[6-ethyl-2-fluoro-3-(1H-pyrazolo[3,4-b]pyridin-3-ylmethyl)-phenoxy]-benzonitrile | 406.9 | 406 | 205.0-206.9 |
| I-26 | 3-[6-Bromo-2-fluoro-3-(5-fluoro-7-oxy-1H-pyrazolo[3,4-b]pyridin-3-ylmethyl)-phenoxy]-5-chloro-benzonitrile | 491.7 | | 230.9-232.0 |
| I-27 | 3-Difluoromethyl-5-[2-fluoro-6-methoxy-3-(1H-pyrazolo[3,4-b]pyridin-3-ylmethyl)-phenoxy]-benzonitrile | 424.4 | 424 | 197.9-201.9 |
| I-28 | 3-[6-Chloro-2-fluoro-3-(1H-pyrazolo[3,4-b]pyridin-3-ylmethyl)-phenoxy]-5-difluoromethyl-benzonitrile | 428.8 | 428 | 198.0-199 |
| I-29 | 3-[6-Bromo-2-fluoro-3-(1H-pyrazolo[3,4-b]pyridin-3-ylmethyl)-phenoxy]-5-difluoromethyl-benzonitrile | 473.3 | 472 | 192.0-194.4 |
| I-30 | 3-[4-Bromo-3-(3-chloro-5-cyano-phenoxy)-2-fluoro-benzyl]-1H-indazole-7-carbonitrile | 481.7 | 480 | 250.0-251.1 |
| I-31 | 3-[6-Bromo-2-fluoro-3-(1H-pyrazolo[3,4-c]pyridin-3-ylmethyl)-phenoxy]-5-difluoromethyl-benzonitrile | 473.3 | 472 | 166.0-166.9 |
| I-32 | 3-[6-Chloro-2-fluoro-3-(1H-pyrazolo[3,4-c]pyridin-3-ylmethyl)-phenoxy]-5-difluoromethyl-benzonitrile | 428.8 | 427 | |

TABLE 1-continued

| Cpd # | NAME | mw | ms | mp |
|---|---|---|---|---|
| I-33 | 3-Chloro-5-[6-cyclopropyl-2-fluoro-3-(1H-pyrazolo[3,4-b]pyridin-3-ylmethyl)-phenoxy]-benzonitrile | 418.9 | 418 | 215.0-216.8 |
| I-34 | 3-[6-Bromo-2-fluoro-3-(5-fluoro-6-oxo-6,7-dihydro-1H-pyrazolo[3,4-b]pyridin-3-ylmethyl)-phenoxy]-5-chloro-benzonitrile | 491.7 | 492 | |
| I-35 | 3-[3-(7-Amino-1H-indazol-3-ylmethyl)-6-bromo-2-fluoro-phenoxy]-5-chloro-benzonitrile | 471.7 | 470 | 179.9-181.3 |
| I-36 | N-{3-[4-Bromo-3-(3-chloro-5-cyano-phenoxy)-2-fluoro-benzyl]-1H-indazol-7-yl}-acetamide | 513.8 | 512 | |
| I-37 | 3-[6-Bromo-2-fluoro-3-(1H-pyrazolo[4,3-c]pyridin-3-ylmethyl)-phenoxy]-5-chloro-benzonitrile | 457.7 | | 216.0-218.5 |
| I-38 | N-{3-[4-Bromo-3-(3-chloro-5-cyano-phenoxy)-2-fluoro-benzyl]-1H-indazol-7-yl}-methanesulfonamide | 549.8 | 548 | 234.0-236.0 |
| I-39 | 3-[6-Bromo-2-fluoro-3-(7-methoxy-1H-pyrazolo[3,4-c]pyridin-3-ylmethyl)-phenoxy]-5-chloro-benzonitrile | 487.7 | 486 | |
| I-40 | 3-Difluoromethyl-5-[2-fluoro-6-methyl-3-(1H-pyrazolo[3,4-b]pyridin-3-ylmethyl)-phenoxy]-benzonitrile | 408.4 | 408 | 212.5-214.4 |
| I-41 | 3-[3-(7-Amino-1H-pyrazolo[3,4-c]pyridin-3-ylmethyl)-6-bromo-2-fluoro-phenoxy]-5-chloro-benzonitrile | 472.7 | 471 | |
| I-42 | 3-Chloro-5-[6-chloro-3-(7-chloro-1H-pyrazolo[3,4-c]pyridin-3-ylmethyl)-2-fluoro-phenoxy]-benzonitrile | 447.7 | 447 | |
| I-43 | 3-[4-Chloro-3-(3-chloro-5-cyano-phenoxy)-2-fluoro-benzyl]-1H-pyrazolo[3,4-c]pyridine-7-carbonitrile | 438.3 | 437 | |
| I-44 | 5-[6-Chloro-3-(7-cyano-1H-pyrazolo[3,4-c]pyridin-3-ylmethyl)-2-fluoro-phenoxy]-isopthalonitrile | 428.8 | 428 | |
| I-45 | 5-[6-Ethyl-2-fluoro-3-(1H-pyrazolo[3,4-b]pyridin-3-ylmethyl)-phenoxy]-isophthalonitrile | 397.4 | 397 | |
| I-46 | 3-Chloro-5-[6-chloro-2-fluoro-3-(1H-pyrazolo[3,4-b]pyridin-3-ylmethyl)-phenoxy]-benzonitrile | 413.2 | 412 | 210.0-215.5 |
| I-48 | 3-[6-Bromo-2-fluoro-3-(7-methyl-6-oxo-6,7-dihydro-1H-pyrazolo[3,4-b]pyridin-3-ylmethyl)-phenoxy]-5-chloro-benzonitrile | 487.7 | 486 | 291.0-293.0 |
| I-48 | 3-[6-Bromo-2-fluoro-3-(7-methyl-6-oxo-6,7-dihydro-1H-pyrazolo[3,4-b]pyridin-3-ylmethyl)-phenoxy]-5-chloro-benzonitrile; TFA salt | 487.7 | 486 | |
| I-49 | 3-[6-Bromo-2-fluoro-3-(1H-pyrazolo[3,4-c]pyridazin-3-ylmethyl)-phenoxy]-5-chloro-benzonitrile | 458.7 | 457 | 237.6-240.8 |
| I-50 | 3-[6-Bromo-2-fluoro-3-(6-methyl-7-oxo-4,5,6,7-tetrahydro-1H-pyrazolo[3,4-c]pyridin-3-ylmethyl)-phenoxy]-5-chloro-benzonitrile | 489.7 | 488 | 235.5-237.1 |
| I-51 | 3-[6-Bromo-2-fluoro-3-(6-methyl-7-oxo-4,5,6,7-tetrahydro-1H-pyrazolo[3,4-c]pyridin-3-ylmethyl)-phenoxy]-5-chloro-benzonitrile; trifluoroacetate salt | 407.8 | | |
| I-52 | 5-[6-Bromo-2-fluoro-3-(1H-pyrazolo[3,4-c]pyridazin-3-ylmethyl)-phenoxy]-isophthalonitrile; trifluoroacetate salt | 449.9 | 449 | |
| I-53 | 3-[6-Bromo-2-fluoro-3-(1H-pyrazolo[3,4-b]pyrazin-3-ylmethyl)-phenoxy]-5-chloro-benzonitrile | 458.68 | 457 | 204.0-205.0 |
| I-54 | 5-[6-Ethyl-2-fluoro-3-(1H-pyrazolo[3,4-c]pyridazin-3-ylmethyl)-phenoxy]-isophthalonitrile | 398.4 | 398 | |
| I-55 | 3-Chloro-5-[6-ethyl-2-fluoro-3-(1H-pyrazolo[3,4-c]pyridazin-3-ylmethyl)-phenoxy]-benzonitrile | 407.83 | 407 | |
| I-56 | 3-Chloro-5-[6-cyclopropyl-2-fluoro-3-(1H-pyrazolo[3,4-c]pyridazin-3-ylmethyl)-phenoxy]-benzonitrile | 419.85 | 419 | |
| I-57 | 5-[6-Cyclopropyl-2-fluoro-3-(1H-pyrazolo[3,4-c]pyridazin-3-ylmethyl)-phenoxy]-isophthalonitrile | 410.4 | 410 | |
| I-58 | 3-Chloro-5-[2-fluoro-6-methoxy-3-(1H-pyrazolo[3,4-c]pyridazin-3-ylmethyl)-phenoxy]-benzonitrile | 409.8 | 410 | |
| I-59 | 5-[6-Chloro-2-fluoro-3-(1H-pyrazolo[3,4-c]pyridazin-3-ylmethyl)-phenoxy]-isophthalonitrile | 404.8 | | 222.8-224.7 |
| I-60 | 3-Chloro-5-[6-difluoromethyl-2-fluoro-3-(1H-pyrazolo[3,4-c]pyridazin-3-ylmethyl)-phenoxy]-benzonitrile | 429.8 | | 177.5-178.2 |
| I-61 | 3-[6-Chloro-2-fluoro-3-(1H-pyrazolo[3,4-c]pyridazin-3-ylmethyl)-phenoxy]-5-methyl-benzonitrile | 393.8 | | 200.0-202.9 |
| I-62 | 3-[6-Chloro-2-fluoro-3-(1H-pyrazolo[3,4-c]pyridazin-3-ylmethyl)-phenoxy]-5-difluoromethyl-benzonitrile | 429.8 | | |
| I-63 | 3-Chloro-5-[2-fluoro-6-methanesulfonyl-3-(1H-pyrazolo[3,4-c]pyridazin-3-ylmethyl)-phenoxy]-benzonitrile | 457.9 | | 239.5-240.7 |

[1.]HIV RT inhibition data for compounds I-1 to I-6 were measure by the procedure in example 28. The remaining compounds were measure by the procedure in example 27

SCHEME A

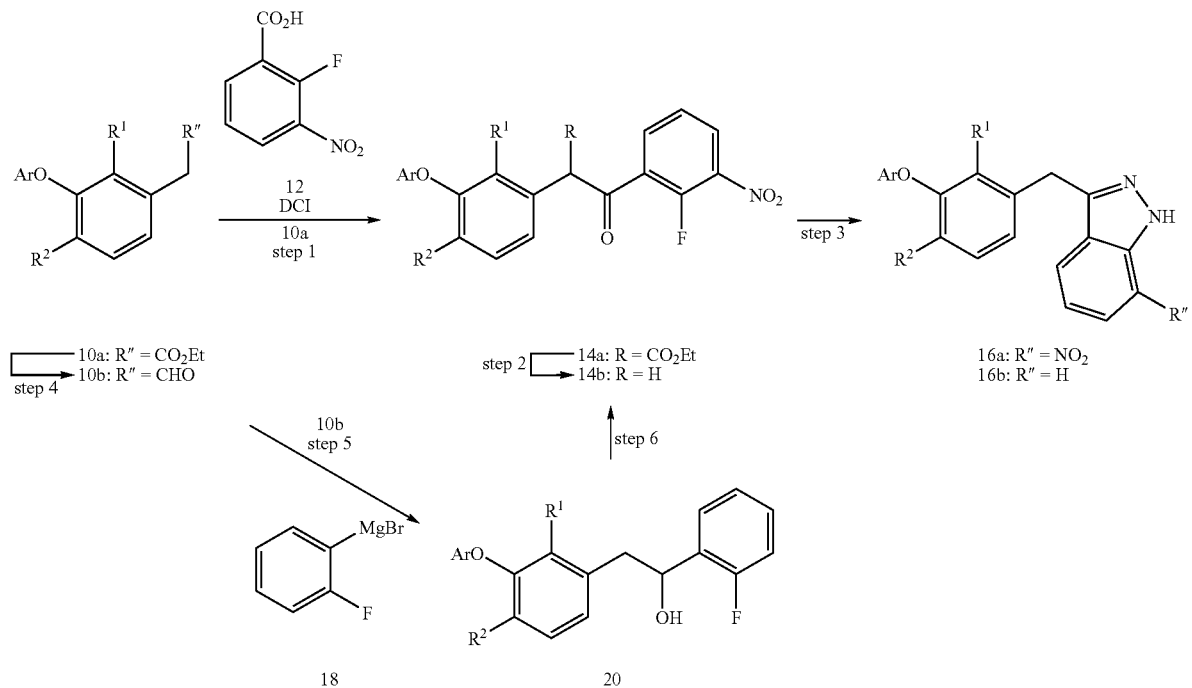

The starting materials for pyrazoles, indazoles, aza-indazoles and di-aza-indazoles of the present invention of are esters of 2,4-disubstituted-3-aryloxy-phenylacetic acids, e.g., 10a, which can be prepared as described in reference example A. Some embodiments of the present invention are non-fused pyrazoles that are readily prepared by cyclization of a β-keto-ester and hydrazine (see, e.g., example 1) or by alkylation of a metallated pyrazole (example 2). The fused pyrazoles disclosed herein can be conveniently prepared by intramolecular cyclization of hydrazine and an α-oxo aromatic ring bearing a displaceable residue ortho to the oxo substituent. The displaceable residue is typically a halogen; however, other leaving groups (such as a mesylate or substituted aryloxy ring) also undergo similar reactions. The requisite α-oxo-2-halo-(hetero)aryl fragment 14b were assembled by Claisen condensation of 10a and an optionally substituted 2-halo-benzoic acid ester (e.g., 12). A convenient protocol entails activating the 2-haloaryl carboxylic acid with CDI which produces an activated acid derivative in situ which, in turn, efficiently condenses with 10a in the presence of base to afford the β-ketoester 14a which is saponified and decarboxylated to afford 14b. Alternatively ester 10a can be converted to the corresponding aldehyde 10b by direct reduction to 10b or by reduction to the corresponding primary alcohol and re-oxidation of the alcohol to 10b. Briefly, carboxylic acid derivatives can sometimes be reduced directly to carboxaldehydes with metal hydride reagents such as DIBAL-H or LiAlH(O-tert-Bu)$_3$ in an inert solvent such as an ether or hydrocarbon solvent typically at reduced temperatures. More vigorous conditions typically afford the corresponding primary alcohol which is readily re-oxidized to the aldehyde with a variety of oxidizing agents well known in the art (see, e.g., J. March, *Advanced Organic Chemistry*. John Wiley & Sons, New York, 1992, pp. 1167-1172). Addition of a metallated (hetero)aromatic compound to the carbonyl and subsequent oxidation of the resulting secondary also affords 14b. Cyclization of ortho-substituted acetophenones with hydrazines has been utilized to produce indazoles (X. Li et al., *J. Med Chem.* 2003 46(26): 5663-5673; B. R. Henke et al., *J. Med. Chem.* 1997 40(17): 2706-2725; S. Caron and E. Vazquez, *Org. Proc. Res. Develop.* 2001 5(6):587-592). The reaction can be run in any inert solvent which boils at a temperature sufficiently high to result in formation of the imine and displacement of the leaving group.

SCHEME B

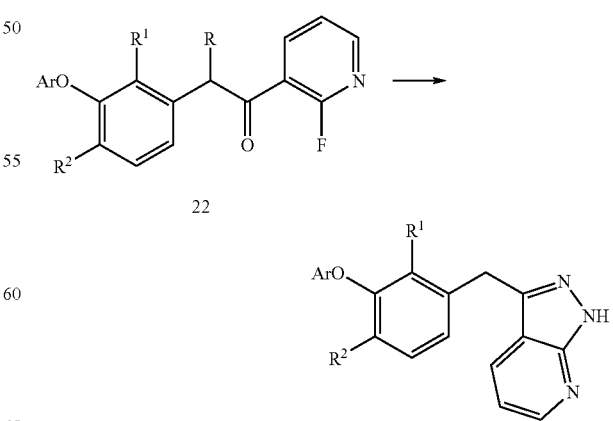

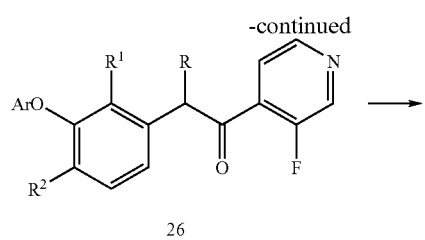

26

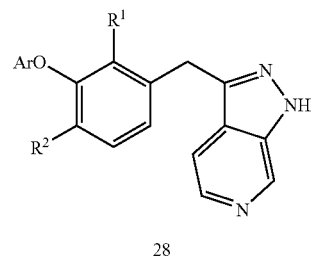

28

The present invention also includes fused aza- and di-aza-indazoles compounds. 1H-pyrazolo[3,4-b]pyridin-3-ylmethyl compounds can be prepared from a 3-acyl-2-halopyridine precursor 22 by cyclization with hydrazine (B. M. Lynch et al., *Can. J. Chem.* 1988 66(3):420-428). The requisite compounds are available by utilizing the Claisen condensation (affording 22 wherein R=alkoxycarbonyl)/decarboxylation (affording 22 wherein R=H) starting from 2-halo-nicotinic acid compounds (e.g., example 6). Thus treatment of 3-{6-bromo-2-fluoro-3-[2-(2-fluoro-pyridin-3-yl)-2-oxo-ethyl]-phenoxy}-5-chloro-benzonitrile (22, R=H, R¹=F, R²=Br, Ar=3-chloro-5-cyano-phenyl) with hydrazine results in formation of the imine and displacement of the labile fluorine on the pyridine ring to afford I-7. A 2-chloro substituted nicotinic acid also can be used to introduce the pyrazole ring. Alternatively pyridine derivatives which can be selectively metallated at the 3-position can be condensed with the aldehyde and re-oxidized to the ketone (e.g., example 7). The optimal process will depend upon the availability of a suitable reactant. 1H-pyrazolo[3,4-c]pyridin-3-ylmethyl derivatives were prepared analogously from 3-halo-isonicotinic acid derivatives (e.g., example 16) or from 3-halo-4-metallated pyridines (e.g., example 12). 1H-Pyrazolo[3,4-d]pyrimidin-3-yl analogs were prepared from 4-chloro-pyrimidine-5-carboxylic acid utilizing the Claisen condensation/intramolecular hydrazine cyclization sequence which afforded I-18. 6-Chloro-1H-pyrazolo[3,4-d]pyrimidinyl compounds were prepared similarly staring from 2,4-dichloro-pyrimidine-5-carboxylic acid. Displacement of the 2-chloro substituent by hydrazine during the cyclization resulting in the isolation of 3-[6-bromo-2-fluoro-3-(6-hydrazino-1H-pyrazolo[3,4-d]pyrimidin-3-ylmethyl)-phenoxy]-5-chloro-benzonitrile trifluoroacetic acid salt (I-10) as byproduct of the reaction. Compounds of formula I wherein A is 1H-pyrazolo[3,4-c]pyridazin-3-ylmethyl (A=A2, X¹=X²=N, X³=CH) were prepared analogously except the Claisen condensation was carried out with 3-(2,4-difluoro-phenoxy)-pyridazine-4-carboxylic acid (see example 21) rather than 2-fluoro-nicotinic acid.

SCHEME C

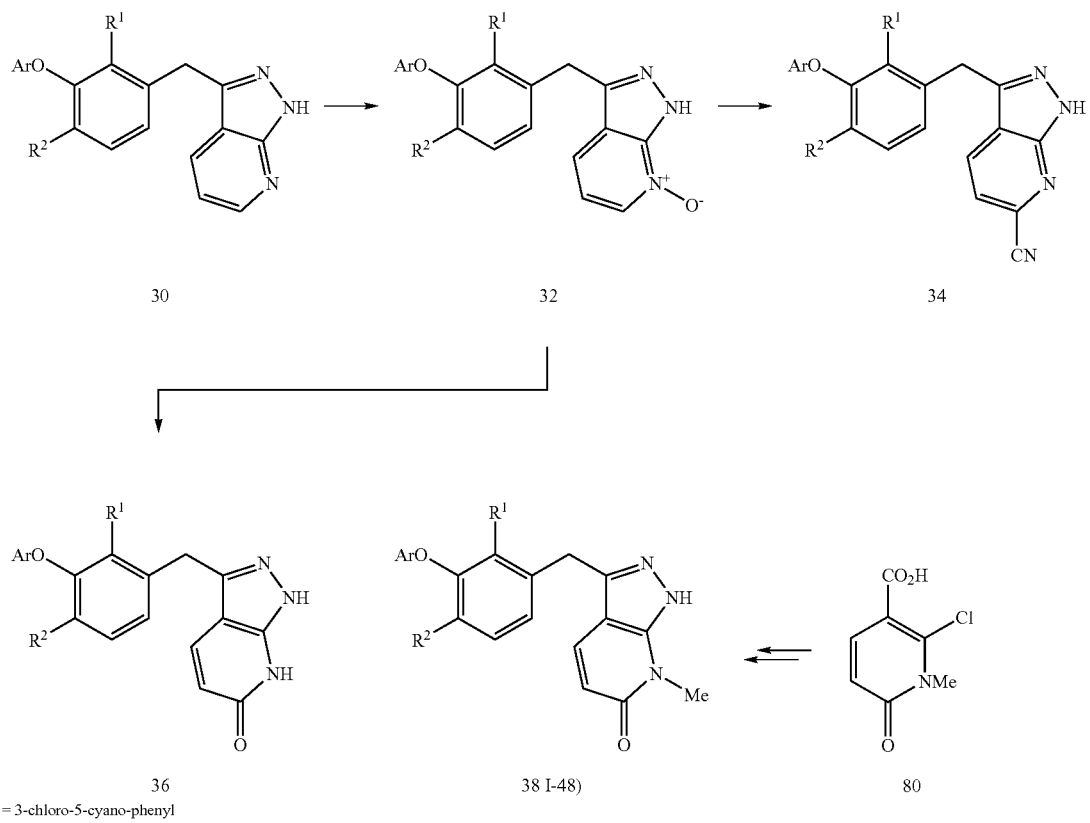

Additional substitution on the 2-halo-nicotinic acid precursor affords a route to pyrazolo[3,4-b]pyridine-3-yl derivatives. (e.g., I-22 and I-23). Alternatively, the pyrazolo[3,4-b]pyridine ring can be further substituted after elaboration of the fused ring. Oxidation of the pyridine nitrogen to the corresponding N-oxide was accomplished with MCBPA. Other conventional oxidants, e.g., $H_2O_2$ and peracids, are known to useful for the same transformation. The N-oxide was converted to the corresponding nitrile (I-14) with sodium cyanide and TMSCI (H. Vorbrüggen and K. Krolikiewicz, *Synthesis* 1983 316-18) or to the corresponding 6-oxo-6,7-dihydro-1H-pyrazolo[3,4-b]pyridine-3-yl derivative (I-12) with trifluoroacetic anhydride (TFAA) (K. Konno et al., *Heterocycles* 1986 24(8):2169-2172). 6-Oxo-6,7-dihydro-1H-pyrazolo[3,4-b]pyridine-3-yl derivatives with an N-alkyl substituent on the pyridone nitrogen were prepared by an analogous two-step Clasien condensation/intramolecular hydrazine cyclization sequence starting from the N-alkylated pyridone 80. Activation of 40 with CDI results in displacement of the chloride by liberated imidazole which is subsequently displaced by hydrazine during the cyclization (see example 9).

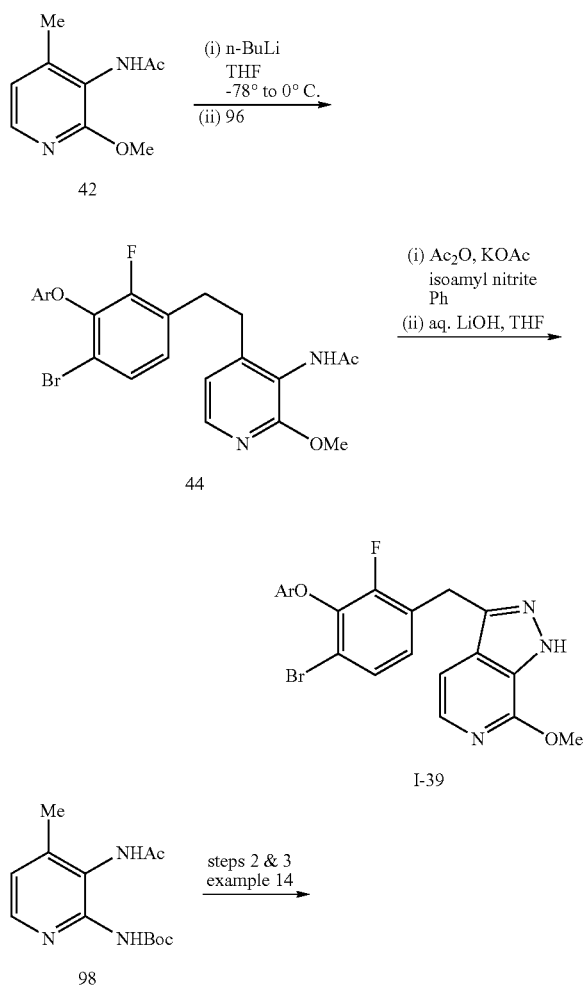

SCHEME D

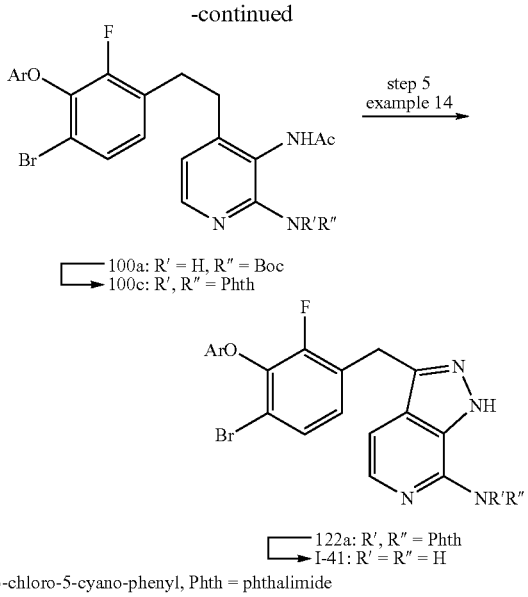

Ar = 3-chloro-5-cyano-phenyl, Phth = phthalimide

Certain substituted pyrazolo[3,4-b]pyridine-3-ylmethyl compounds were prepared utilizing the Jacobson-Huber synthesis (P. Marakos et al., *SynLett* 1997 561; C. Ruechardt and V. Hassmann, *Annalen* 1980 908-927; C. Ruechardt and V. Hassmann, *Synthesis* 1972 375; P. Jacobson and L. Huber, *Chem. Ber.* 1908 41:667). Utilizing these conditions the aryl amine is converted to a diazonium salt which undergoes intramolecular cyclization to the aza-indazole. The required picoline derivatives, 42 and 98, can be prepared by literature procedures. Deprotonation of the heteroaryl methyl group was accomplished with n-BuLi and the resulting heteroarylmethyl lithium intermediate was alkylated with 96 to afford 44 which was subjected to the Jacobson procedure to afford I-39.

Dosage and Administration

The compounds of the present invention may be formulated in a wide variety of oral administration dosage forms and carriers. Oral administration can be in the form of tablets, coated tablets, dragëes, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in neither preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. N-acylsulfonamides have an acidic proton which can be abstracted to form a salt with an organic or inorganic cation.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The status of an HIV infection can be monitored by measuring viral load (RNA) or monitoring T-cell levels. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another non-nucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other animals. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

These examples and preparations which follow are provided to enable those skilled in the art to more clearly understand and to practice the present invention. They should not be considered as limiting the scope of the invention, but merely as being illustrative and representative thereof.

REFERENTIAL EXAMPLE A

3-Aryloxyphenylacetic Acids

[4-Chloro-3-(3-chloro-5-cyano-phenoxy)-2-fluoro-phenyl]-acetic acid (R-1) and [4-chloro-3-(3-chloro-5-cyano-phenoxy)-2-fluoro-phenyl]-acetyl chloride (R-2)

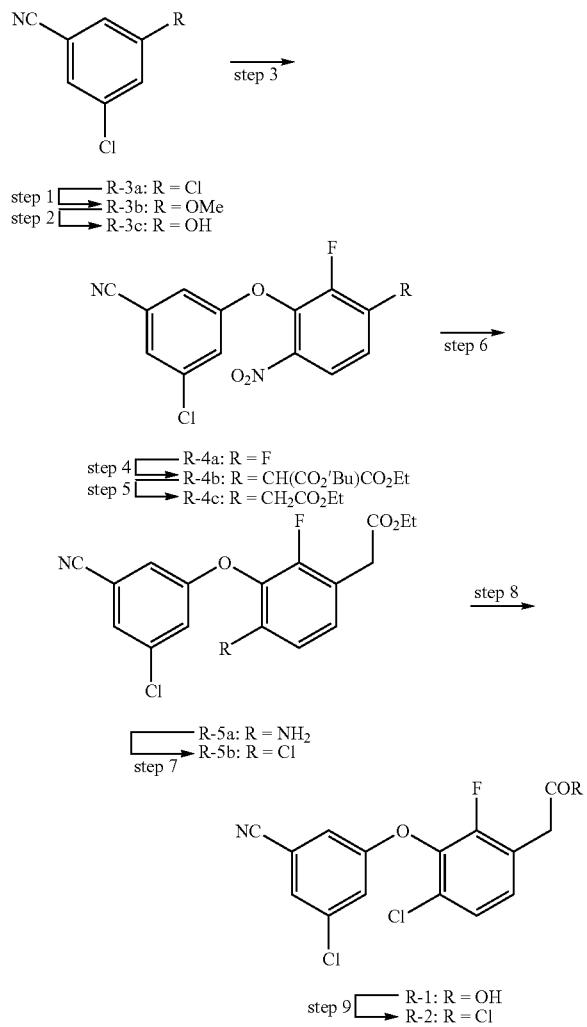

step 1—A 100 ml round bottom flask was charged under a stream of nitrogen with 3,5-dichlorobenzonitrile (R-3a, 7.0 g, 40.69 mmol) and anhydrous DMF (75 mL). To the solution was added sodium methoxide (2.26 g, 44.76 mmol) and resulting solution was stirred further at RT for 24 h. When the reaction was complete, aqueous 10% HCl added dropwise to the reaction vessel. The crude mixture was extracted with EtOAc and sequentially washed with aqueous acid, water and brine. The EtOAc extracts were dried (Na$_2$SO$_4$), filtered and the solvent was removed in vacuo to afford a crude solid which was recrystallized from hexane/acetone to afford 5.9 g (86%) of R-3b.

step 2—A 250 mL flask was charged with R-3b (7.0 g, 41.766 mmol) and 2,4,6-collidine (100 mL). The mixture was heated to 170° C., LiI (16.76 g, 125.298 mmol) was added and the reaction mixture was heated for 4 h. When R-3b was consumed the reaction was cooled to RT and quenched with 10% aqueous HCl. The resulting mixture was extracted with EtOAc and washed with water and brine. The EtOAc extract was dried over (Na$_2$SO$_4$) and filtered. The solvent was removed in vacuo to afford a yellow oil which was purified by silica gel chromatography eluting with EtOAc/hexane (10:90) to afford 6.0 g (94%) of R-3c.

step 3—A 250 mL round-bottom flask was charged with R-3c (6.0 g, 39.070 mmol) and anhydrous THF (100 mL) and the solution was cooled to 0° C. To the cooled solution was added sodium tert-butoxide (46.89 g, 4.51 mmol) and the resulting solution stirred for 1 h. 2,3,4-Trifluoro-nitro-benzene (6.92 g, 39.070 mmol) was added dropwise while maintaining the reaction at 0° C. until phenol was completely consumed. The mixture was quenched by addition of 10% aqueous HCl and the resulting mixture was stirred for an additional hour. The mixture was extracted with EtOAc and washed with water and brine. The EtOAc was dried (Na$_2$SO$_4$) and filtered. The solvent was removed in vacuo to yield a yellow oil which was purified by SiO$_2$ column chromatography eluting with hexane/EtOAc (92:8) to afford 10 g (82%) of R-4a.

step 4—To a solution of tert-butyl ethyl malonate (10.31 g, 54.80 mmol) and anhydrous NMP (200 mL) cooled to 0° C. and stirred under a nitrogen atmosphere. To this solution was added NaH 40% in mineral oil (1.84 g, 76.70 mmol). The mixture was allowed to stir at 0° C. for an additional 1 h. The bis-aryl ether R-4a (15.00 g, 49.80 mmol) was then added to the reaction vessel and stirred under nitrogen at RT until the reaction was complete. The mixture was quenched by addition of aqueous 10% HCl at RT. The mixture was extracted with EtOAc and washed with water and brine. The EtOAc was dried (Na$_2$SO$_4$) and filtered. The solvent was removed in vacuo to afford R-4b as a light yellow oil which was used in the next step without any further purification.

step 5—The diester R-4b (24.0 g, 50.117 mmol) was dissolved in dichloroethane (300 mL) and TFA (6.29 g, 55.13 mmol) and heated to 75° C. for 24 h. The mixture was cooled to RT and solvent and excess TFA were removed in vacuo. The crude oil was re-dissolved in DCM and cooled to 0° C. and aqueous NaHCO$_3$ was added. The mixture was extracted with DCM and washed with water and brine. The DCM was dried (Na$_2$SO$_4$), filtered and the solvent was removed in vacuo to afford a yellow oil. The crude oil was purified by SiO$_2$ chromatography eluting with hexane/EtOAc (90:10) to afford 15.0 g (80%) of R-4c.

step 6—A 250 mL round bottom flask was charged with R-4c (8.0, 21.12 mmol) and absolute EtOH. To the reaction vessel was added NH$_4$Cl (2.26 g, 42.244 mmol), water (30 mL) and iron (1.17 g, 21.12 mmol). The reaction was stirred and heated to 80° C. for 4 h. When R-4c was consumed, the heterogeneous mixture was filtered through a pad of CELITE® and the filter cake was washed with EtOAc. The aqueous filtrate was extracted with EtOAc and washed with water and brine. The combined EtOAc extracts were dried over (Na$_2$SO$_4$) and filtered. The solvent was removed in vacuo to afford a pale oil which was purified by SiO$_2$ chromatography eluting with hexane/EtOAc (85:15) to afford 6.0 g (87%) of R-5a.

step 7—A 100 mL round bottom flask was charged with anhydrous MeCN (15 mL) under a continuous stream of nitrogen. To this mixture was added Cu(II)Cl$_2$ (0.083 g, 0.624 mmol) and tert-butyl nitrite (0.064 g, 0.624 mmol). The mixture was heated to 70° C. 30 min. To this mixture was added R-5a (0.100 g, 0.624 mmol) in a single portion and stirring continued for an additional 2 h. Upon consumption of starting materials the mixture was cooled to RT and reaction mixture quenched with aqueous 10% HCl. The mixture was extracted with EtOAc and the combined extracts were washed with water and brine. The EtOAc extract was dried ($Na_2SO_4$) and filtered. The solvent was removed in vacuo to afford a light brown oil which was purified by $SiO_2$ chromatography eluting with hexane/EtOAc (96:4) to afford 0.080 g (76%) of R-5b.

step 8—A oven-dried 100 mL round bottom flask purged with nitrogen and was charged with R-5b (2.0 g; 5.43 mmol) and THF (20 mL) and stirred under a stream of nitrogen. To the reaction vessel was added LiOH (0.46 g; 10.86 mmol) followed by 5 mL deionized water. The reaction was stirred for 1 h under a continuous stream of nitrogen. The homogeneous mixture was cooled to 0° C. and quenched with 10% aqueous HCl. The reaction mixture was stirred for an additional 15 min. The crude mixture was extracted with EtOAc and washed with water and brine. The organic extracts were dried ($Na_2SO_4$) and filtered. The solvent was removed in vacuo and the crude acid R-1 was used without any further purification.

step 9—A 100 mL round bottom was charged with R-1 (0.200 g, 0.520 mmol) and DCM (5 mL) and the solution was stirred under nitrogen at RT. To the solution was added thionyl chloride (0.061 g, 0.520 mmol) dropwise followed by a single drop of DMF. The reaction was stirred for 1 h at RT. Excess solvent and thionyl chloride were removed in vacuo to afford the carboxylic acid R-2 as a crude yellow oil which was used in the next reaction without any further purification.

General Procedure for the Preparation of Tert-Butyl Phenylacetates

To an ice-cold solution of the ethyl or methyl ester of a substituted phenyl acetic acid in THF is added an aqueous solution of $LiOH.H_2O$ (1.5 equivalents). The reaction mixture is stirred at RT and the progress of the hydrolysis is followed by tlc or hplc. When the reaction is complete 1M HCl and EtOAc are added and the organic phase is washed with brine, dried, filtered and evaporated to afford the corresponding carboxylic acid.

To a solution of the carboxylic acid in tert-butanol maintained under an inert atmosphere was added DMAP (0.3 equivalents and di-tert-butyl dicarbonate (Boc anhydride, 2 equivalents). The reaction is stirred at RT until gas evolution ceases and the reaction is complete. The solvent is removed in vacuo and the product purified by $SiO_2$ chromatography.

4-Chloro-3-(3,5-dicyano-phenoxy)-2-fluoro-phenyl]-acetic acid (R-7) and 4-chloro-3-(3,5-dicyano-phenoxy)-2-fluoro-phenyl]-acetyl chloride (R-8)

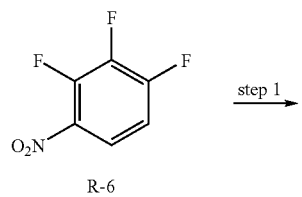

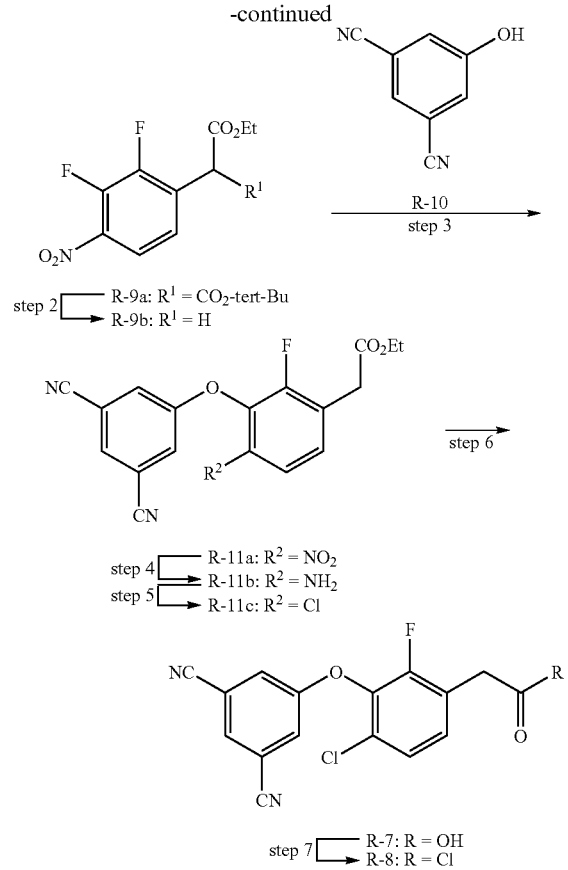

Steps 1 & 2-ethyl 2,3-difluoro-4-nitrophenylacetate (R-9b)

To an ice-cold solution of tert-butyl ethylmalonate (Alfa Aesar) (31.2 g, 166 mmole) in NMP (300 mL) cooled to 0° C. under a nitrogen atmosphere was added NaH (60% oil dispersion, 13.1 g, 218 mmole) while maintaining the temperature below 20° C. After addition complete, the solution was aged for 20 min. To this solution was added dropwise 2,3,4-trifluoronitrobenzene (R-6, Oakwood Products Inc.) (26.6 g, 163 mmole) in NMP (50 mL) while maintaining the temperature below 20° (highly exothermic). Upon completion of the addition the reaction was aged at RT for 2 h. The solution was added to an aqueous solution of $NH_4Cl$ (1.5 L), extracted with EtOAc (3×200 mL), washed 5 times with water (400 mL), dried ($MgSO_4$) and evaporated. The crude substituted malonic ester R-9a was used without further purification.

Ester R-9a was dissolved in DCM (400 mL) and TFA (100 mL) was added, this solution heated at 40° C. for 16 h. The reaction mixture was cooled to RT and the solvents evaporated. The crude product dissolved in EtOAc (400 mL), washed sequentially with aqueous $NaHCO_3$, water, and brine, dried ($MgSO_4$) and evaporated. The residual oil was purified by $SiO_2$ chromatography eluting with 5% EtOAc/hexanes to afford R-9b as a golden oil (11.9 g) (30%) which crystallizes upon sitting.

step 3—A solution of anhydrous THF (100 mL) and R-10 (10.00 g, 69.38 mmole) cooled to 0° C. was treated with sodium tert-butoxide (7.34 g, 76.32 mmol). The mixture was stirred for 30 min at 0° C. then R-9b (17.01, 69.38 mmole) was added and stirred for 3 h. The reaction was quenched with 10% aqueous HCl. The crude mixture was extracted with EtOAc and the combined extracts washed with water and brine. The organic phase was dried ($Na_2SO_4$) and filtered. The solvent was removed in vacuo to afford a crude oil which was purified by $SiO_2$ chromatography eluting with hexanes/EtOAc (90:10) to afford 20 g (78%) of R-11a.

Introduction of the chloro substituent (steps 4 & 5) were carried out as described in steps 6 & 7 of the preparation of R-1 (supra). Hydrolysis of the ester and formation of the acid chloride (steps 7 & 8) were carried out by the procedures described in steps 8 & 9 of the preparation of R-2 which afforded R-7 and R-8.

[4-Chloro-3-(3-cyano-5-difluoromethoxy-phenoxy)-2-fluoro-phenyl]-acetic acid ethyl ester (R-12)

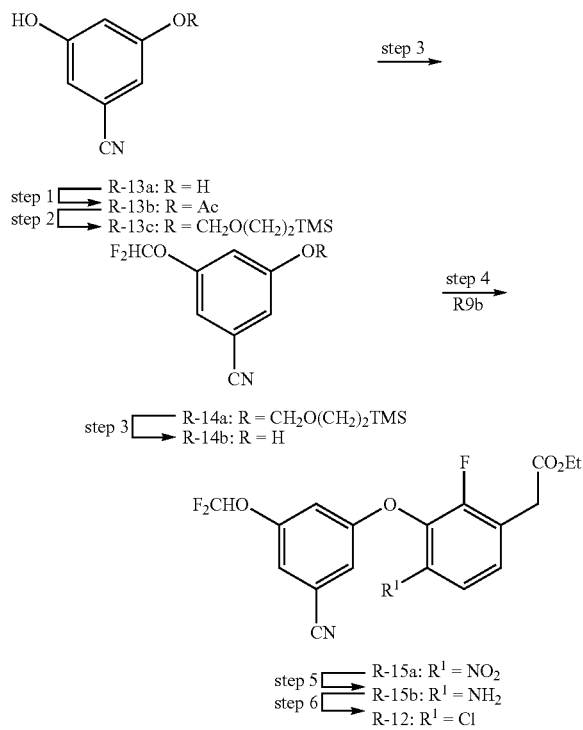

step 1—Acetic anhydride (30 mL, 4 equiv) was added to a solution of R-13a (10.36 g, 77 mmol) in anhydrous pyridine (60 mL) cooled to 0° C. and blanketed with nitrogen. The reaction was warmed to RT and stirred for 16 h. The volatile materials were removed in vacuo, and the remaining oil was dissolved in EtOAc, washed with water, 5% HCl solution, brine and dried ($MgSO_4$). The volatile materials were removed to afford 14.5 g (86%) of the diacetate. The diacetate (14 g, 64 mmol) was dissolved in a mixture of EtOH (100 mL) and benzene (100 mL) and cooled to 0° C. A solution of KOH (3.6 g, 1 equiv) in EtOH was added dropwise. After 1 h, the solution was added to an ice-cold solution of saturated $NH_4Cl$, extracted with ether, and washed with brine. The $Et_2O$ extracts were concentrated and purified by $SiO_2$ chromatography eluting with a hexane/EtOAc gradient (0% to 25% EtOAc) which afforded 10 g of R-13b (88%).

step 2—(2-Trimethylsilyl-ethoxy)-methyl-chloride (2.2 mL, 1.1 equiv) was added to a solution of the R-13b (2.0 g, 11.3 mmol) and DIPEA (2.4 mL, 1.2 equiv) in DCM (50 mL) cooled to 0° C. The solution was warmed to RT, stirred for 16 h, and poured into a saturated $NaHCO_3$ solution. The aqueous solution was extracted with DCM, and the combined organic extracts washed with water and brine and dried ($MgSO_4$). The solvents were removed in vacuo and the acetylated product was dissolved in a mixture of water (8 mL) and THF (32 mL). $LiOH.H_2O$ (0.71 g, 1.5 equiv) was added. The mixture was stirred for 2 h, acidified to pH 5 and extracted with ether. The organic layer was dried ($MgSO_4$) and evaporated to provide 2.5 g (80%) of the R-13c.

step 3—$F_2ClCCO_2Na$ (2.84 g, 2.3 equiv) was added to a solution of $Cs_2CO_3$ (3.69 g, 1.4 equiv), R-13c (2.26 g, 8.09 mmol), DMF (32 mL) and water (2 mL). The solution was heated to 100° C. for 2 h, cooled to RT, and poured into a saturated solution of $NH_4Cl$. The solution was extracted with a mixture of EtOAc and hexanes, and the organic layer was washed with brine and dried ($MgSO_4$). The crude product was purified by $SiO_2$ chromatography eluting with a EtOAc/hexane gradient (0 to 10% EtOAc) which afforded 1.83 g (70%) of R-14a. The difluoromethyl ether R-14a was dissolved in MeOH (30 mL), and 5.6 mL of a 1.0 M solution of HCl was added. The solution was heated to 50° C. for 5 h, and stirred at RT for 16 h. The volatile materials were evaporated, and the aqueous residue was partitioned between DCM and water. The aqueous layer was extracted with DCM, and the combined extracts were washed with water and brine. The volatile materials were removed in vacuo to afford 780 mg (73%) of R-14b.

Condensation of R-14b and R-9b was carried out by the procedure described in step 3 of the preparation of R-7. Reduction of the nitro group (step 5), diazotization of the amine and displacement by chloride (step 6), hydrolysis of the ester and conversion of the acid to the acid chloride were carried out by the procedure described in steps 6-9 of the preparation of R-2.

[4-Chloro-3-(3-cyano-5-methoxy-phenoxy)-2-fluoro-phenyl]-acetic acid ethyl ester was prepared in similar fashion except in step 4, 3-cyano-5-methoxy-phenol (CAS Reg. No. 124993-53-9) was used in place of R-14b.

[4-Chloro-3-(3-cyano-5-difluoromethyl-phenoxy)-2-fluoro-phenyl]-acetic acid ethyl ester (R-16a)

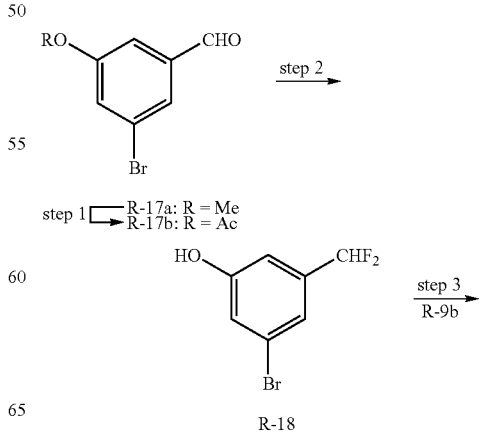

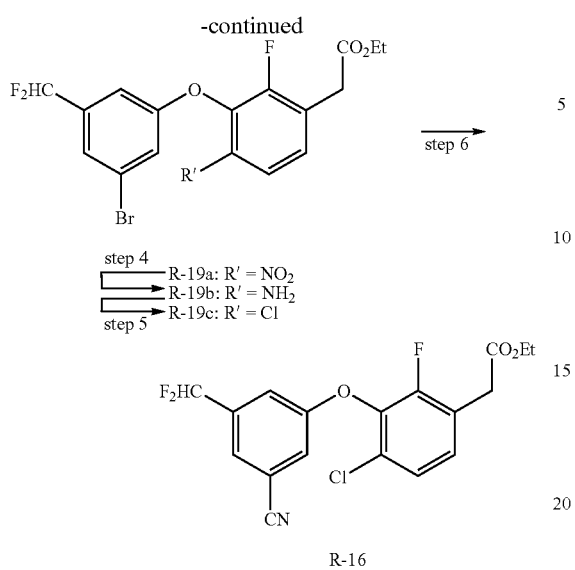

step 4 ⎡→ R-19a: R' = NO$_2$
         → R-19b: R' = NH$_2$
step 5 ⎣→ R-19c: R' = Cl

R-16 step 1—A solution of BBr$_3$ (29.1 mL of a 1.0 M solution in DCM, 29.1 mmol) was added slowly to a solution of R-17a (2.5 g, 11.62 mmol, CAS Reg. No. 262450-65-7) in anhydrous DCM (25 mL) maintained under N$_2$ at −78° C. The orange solution was warmed to RT, stirred for 2 h, and poured onto ice. The mixture was extracted with DCM (100 mL), and the organic layer was washed with H$_2$O (50 mL) and brine (50 mL). The solvents were evaporated, and the remaining oil was purified by SiO$_2$ chromatography eluting with a EtOAc/hexanes gradient (0% to 20% EtOAc) to provide the desired phenol. To a solution of this phenol in pyridine (10 mL) under argon was slowly added acetic anhydride (0.6 mL, 6.33 mmol). After 2 h, the volatile materials were removed to provide 3-bromo-5-formyl-phenyl acetate (R-17b, 1.02 g, 40%).

step 2—DAST (1.02 mL, 7.69 mmol) was added to a solution of the 3-bromo-5-formyl-phenyl acetate (R-17b, 1.1 g, 4.52 mmol) in DCM (5 mL) under nitrogen contained in a NALGENE® bottle. EtOH (0.013 mL, 0.23 mmol) was added, and the mixture was stirred for 16 h. The reaction mixture was then added slowly to an aqueous solution of saturated NaHCO$_3$. After the bubbling ceased, DCM (50 mL) was added and the layers were separated. The organic layer was washed with brine (30 mL) and dried (MgSO$_4$). The solvent was removed to provide a yellow oil that was dissolved of THF (15 mL) and H$_2$O (4 mL). LiOH.H$_2$O (474 mg, 11.3 mmol) was added and the reaction mixture was stirred at RT for 2 h. The solution was then added dropwise to 5% aqueous HCl (50 mL), and the mixture was extracted with EtOAc (3×30 mL). The combined organic fractions were washed with brine (30 mL), and dried (MgSO$_4$). Evaporation of the volatile materials afforded an oil that was purified by SiO$_2$ chromatography eluting with an EtOAc/hexanes gradient (0% to 25% EtOAc) to provide 800 mg (79%) of R-18.

Condensation of the phenol R-18 with R-9b (step 3) was carried out by the procedure described in step 3 of the preparation of R-7. Reduction of the nitro group (step 4), diazotization of the amine and displacement by chloride (step 5) to afford R-19c were carried out by the procedure described in steps 6 and 7 of the preparation of R-2.

step 6—A solution of R-19c (757 mg, 1.73 mmol), Pd[P(Ph)$_3$]$_4$(0) (300 mg, 0.26 mmol), and zinc cyanide (122 mg, 1.04 mmol) in DMF (8 mL) under nitrogen was heated to 80° C. for 4 h. The reaction mixture was cooled to RT and added to 2 M aqueous NH$_4$OH. The solution was extracted with 1:1 EtOAc/hexanes (3×30 mL), and the combined organic fractions were washed with H$_2$O (3×20 mL) and dried (MgSO$_4$). The solvent was evaporated, and the remaining oil was purified by SiO$_2$ chromatography eluting with an EtOAc/hexanes gradient (0% to 25% EtOAc) to provide 580 mg (87%) of R-16.

Hydrolysis of the ethyl ester and conversion to the acid chloride can be carried out as described in steps 8-9 of the preparation of R-2.

[3-(3-Bromo-5-cyano-phenoxy)-4-chloro-2-fluoro-phenyl]-acetic acid ethyl ester (R-20c)

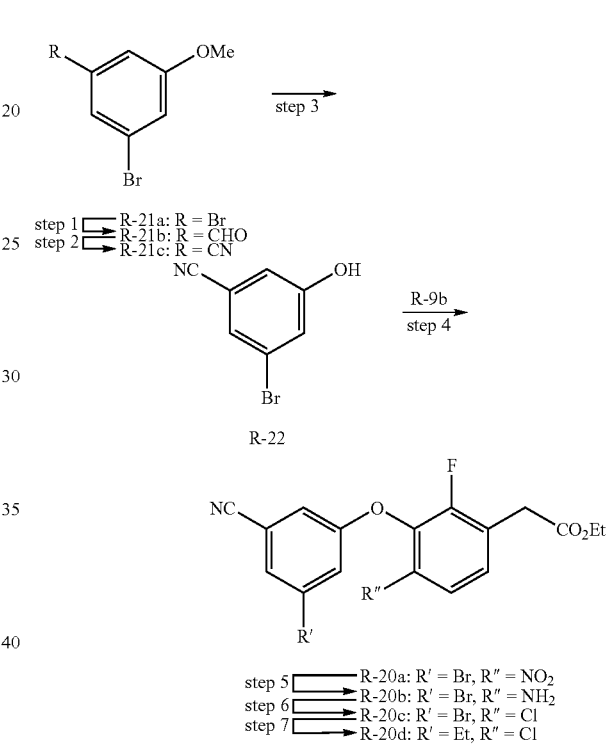

step 1 ⎡→ R-21a: R = Br
step 2 ⎣→ R-21b: R = CHO
         → R-21c: R = CN

R-22 step 5 ⎡→ R-20a: R' = Br, R'' = NO$_2$
step 6 │→ R-20b: R' = Br, R'' = NH$_2$
step 7 │→ R-20c: R' = Br, R'' = Cl
       ⎣→ R-20d: R' = Et, R'' = Cl step 1—n-BuLi (2.6 mL of a 1.6 M solution, 1.1 equiv) was added slowly to a solution of the R-21a (1.0 g, 3.8 mmol, CAS Reg. No. 74137-36-3) in Et$_2$O (20 mL) cooled to −78° C. under an N$_2$ atmosphere. The solution was stirred for 45 min, and DMF was added via syringe. The solution was warmed slowly to RT, added to saturated NH$_4$Cl, and extracted with ether. The organic phase was washed with brine and dried (MgSO$_4$), filtered and evaporated to afford 0.80 g (98%) of R-21b.

step 2—A solution of the aldehyde R-21b (12.0 g, 56 mmol), NH$_2$OH.HCl (19.4 g, 5 equiv), EtOH (100 mL) and pyridine (10 mL) was heated to 65° C. for 16 h. The mixture was cooled to RT, and partitioned between 50% EtOAc/hexanes and water. The organic layer was washed with brine and dried (MgSO$_4$). The volatile materials were evaporated to afford 12.4 g (97%) of the oxime. This material was dissolved in anhydrous dioxane (100 mL) and pyridine (26 mL, 6 equiv). The solution was cooled to 0° C., TFAA (15 mL, 2 equiv) was added, and the mixture was allowed to warm to RT. The solution was stirred for 2 d, and warmed to 60 C for 1 h. The mixture was cooled to RT and added carefully to ice water. The mixture was extracted with DCM, and the combined organic layers were washed with water, 1 M HCl, and brine. The organic layer was dried (MgSO$_4$) and evaporated to afford 10.4 g (90%) of R-21c.

step 3—Anhydrous collidine (100 mL) was added to a dry flask containing R-21c (10.4 g, 49 mmol) and LiI (19.6 g, 3 equiv). The solution was heated under nitrogen to 150° C. overnight, cooled to RT, and poured into an ice cold 1 M HCl solution. The mixture was extracted with a 1:1 EtOAc/hexanes solution, washed with water, and dried (MgSO$_4$). Concentration in vacuo afforded 8.7 g (89%) of R-22.

Condensation of the phenol R-22 with R-9b (step 4) was carried out by the procedure described in step 3 of the preparation of R-7. Reduction of the nitro group (step 5), diazotization of the amine and displacement by chloride (step 6) to afford R-20c were carried out by the procedure described in steps 6 and 7 of the preparation of R-2.

[4-Chloro-3-(3-cyano-5-ethyl-phenoxy)-2-fluoro-phenyl]-acetic acid ethyl ester (R-20d) was prepared from by treating a THF solution of R-20c with, Pd(dppf)Cl$_2$, DIBAL-H (1M in toluene), diethylzinc utilizing the procedure described in the preparation of R-31 (infra).

[4-Bromo-3-(3-chloro-5-cyano-phenoxy)-2-fluoro-phenyl]-acetic acid ethyl ester (R-23a) and [4-Bromo-3-(3-chloro-5-cyano-phenoxy)-2-fluoro-phenyl]-acetic acid (R-23b)

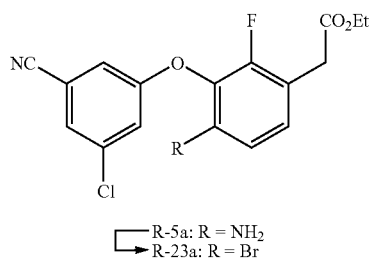

A 150 mL three-neck round bottom flask was charged with MeCN (50 mL), CuBr$_2$ (2.8 g, 12.61 mmol) and t-butyl nitrite (1.4 g, 13.76 mmol), degassed and maintained under an Ar atmosphere and heated to 70° C. To the mixture was added dropwise a solution of R-5a (4.0 g, 11.47 mmol) dissolved MeCN (20 mL). The reaction mixture was stirred at 70° C. for 4 h and then cooled to 0° C. The reaction was quenched by addition of 10% HCl (30 mL) and extracted with EtOAc. The combined extracts were sequentially washed with 10% HCl and brine. The organic extract was dried (Na$_2$SO$_4$), filtered and the volatile solvents removed in vacuo to yield a black oil which was purified by SiO$_2$ chromatography eluting with hexanes/EtOAc (95:5) to afford 2.5 g (52.8%) of R-23a. Hydrolysis of the ethyl ester by the procedure described in step 8 of example 1 afforded the carboxylic acid R-23b.

[4-Bromo-3-(3,5-dicyano-phenoxy)-2-fluoro-phenyl]-acetic acid ethyl ester (R-24) was prepared from R-11b by reduction of the nitro as described in step 6 of the preparation of R-5a and diazotization of the amine and displacement with bromine as described for R-23a.

[4-Bromo-3-(3-cyano-5-difluoromethyl-phenoxy)-2-fluoro-phenyl]-acetic acid ethyl ester (R-25)

step 1—A solution of R-27a (CAS Reg. No. 1435-51-4), MeONa (1 equivalent) and DMF were stirred overnight under an N$_2$ atmosphere at RT. The volatile solvents were removed in vacuo and the residue partitioned between Et$_2$O and water. The organic phase was washed with 5% NaOH, water and brine, dried (MgSO$_4$), filtered and evaporated to afford R-27b.

step 2—To a solution of R-27b (60 g, 0.2256 mol) and anhydrous Et$_2$O (1 L) cooled to –78° C. and maintained under an Ar atmosphere was added dropwise over 30 min n-BuLi (100 mL, 0.2482 mol, 2.5M in hexane). The yellow solution was stirred at –78° C. for 20 min. To the reaction mixture was added dropwise dry DMF (19 mL, 248.2 mmol) over 15 min and the reaction stirred at –78° C. for 10 min before the cooling bath was removed and the reaction allowed to warm to –30° C. over 30 min. The reaction vessel was placed in an ice-water bath and warmed to –10° C. The mixture was slowly added to an ice cold saturated aqueous NH$_4$Cl solution (400 mL). The organic layer was separated and the aqueous phase thrice extracted with Et$_2$O. The combined extracts were washed with water, dried (MgSO$_4$), filtered and evaporated to afford an oil which solidified on standing. The crude product was purified by SiO$_2$ chromatography eluting with a hexane/EtOAc gradient (3 to 5% EtOAc) to afford R-28.

step 3—Cyanation of R-28 to afford R-29a was carried out with Zn(CN)$_2$, Pd(PPh$_3$)$_4$(0) and DMF as described in step 6 of the preparation of R-16 (supra)

step 4—DAST (21.04 mL, 519 mmol) was added to a solution of R-29a (15.1 g, 94 mmol) and DCM (100 mL) contained in a NALGENE® bottle under nitrogen. EtOH (0.013 mL, 0.23 mmol) was added and the mixture was stirred for 16 h. The reaction mixture was then added slowly to an aqueous solution of saturated NaHCO$_3$. After the bubbling was ceased, DCM (50 mL) was added and the layers were separated. The organic layer was washed with brine (30 mL) and dried (MgSO$_4$). The solvent was removed and the crude product was purified by two flash SiO$_2$ chromatographies eluting with an EtOAc/hexanes gradient (0% to 10% EtOAc) to afford R-29b as a white solid.

step 5—The methyl ether R-29b was demethylated in a solution of 48% aqueous HBr and glacial HOAc heated to 120° C. until demethylation was complete. Removal of volatile and partitioning between water and DCM afforded R-26.

Condensation of R-26 and R-9b was carried out by the procedure described in step 3 of the preparation of R-7. Reduction of the nitro group was carried out as described in step 6 of the preparation of R-2. Diazotization and displacement of the diazo with bromine was carried out as described for R-23a to afford R-25.

[3-(3-Chloro-5-cyano-phenoxy)-2-fluoro-4-methyl-phenyl]-acetic acid ethyl ester (R-31)

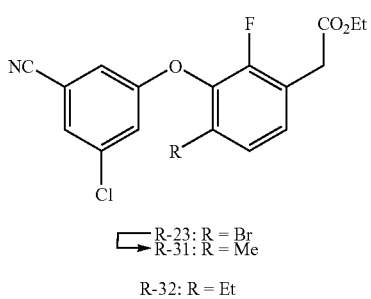

R-32: R = Et

To a degassed ice-cold solution of THF (15 mL), Pd(dppf)Cl$_2$ (0.09 g, 0.121 mmol) was added DIBAL-H (0.012 mmol, 1M solution in toluene). The reaction mixture was allowed to warm to RT. A solution of R-23a (1.0 g, 2.42 mmol) was added followed by dimethyl zinc (1M in THF, 4.240 mmol). The reaction was heated to 65° C. for 4 h, cooled to RT and quenched with aqueous NH$_4$Cl. The resulting mixture was extracted with EtOAc and washed sequentially with NH$_4$Cl and brine. The EtOAc extract was dried (Na$_2$SO$_4$), filtered and the volatile solvent removed in vacuo to yield a dark brown oil that was purified by SiO$_2$ chromatography eluting with hexane/EtOAc (95:5) to afford 0.50 g (59%) of R-31.

[3-(3-Cyano-5-difluoromethyl-phenoxy)-2-fluoro-4-methyl-phenyl]-acetic acid ethyl ester (R-33) was prepared from R-25 using the procedure described above for R-31.

[3-(3,5-Dicyano-phenoxy)-2-fluoro-4-methyl-phenyl]-acetic acid ethyl ester (R-34) was prepared from R-24 using the procedure described above for R-31.

[3-(3-Chloro-5-cyano-phenoxy)-4-ethyl-2-fluoro-phenyl]-acetic acid ethyl ester (R-32) was prepared from R-23 using the procedure described for R-31 except diethylzinc was used in place of dimethylzinc.

[3-(3,5-Dicyano-phenoxy)-4-ethyl-2-fluoro-phenyl]-acetic acid ethyl ester (R-36) was prepared from R-24 using the procedure described for R-31 except diethylzinc was used in place of dimethylzinc

[3-(3-cyano-5-difluoromethyl-phenoxy)-4-ethyl-2-fluoro-phenyl]-acetic acid ethyl ester (R-37) was prepared from R-25 using the procedure described for R-31 except diethylzinc was used in place of dimethylzinc.

[3-(3-Chloro-5-cyano-phenoxy)-4-cyclopropyl-2-fluoro-phenyl]-acetic acid ethyl ester (R-38)

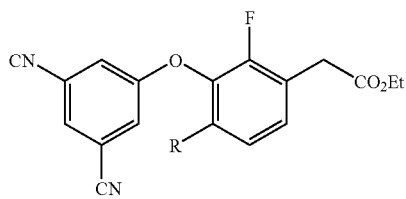

step 1—To a solution of R-24 (0.80 g, 1.99 mmol), Pd(PPh$_3$)$_4$ (0.23 g, 0.10 equiv) and toluene (10 mL) was added tributylvinyltin (0.635 mL, 1.1 equiv) via syringe and the solution was refluxed for 5 h. The reaction was cooled to RT and poured into saturated aqueous NH$_4$Cl and extracted with EtOAc. The organic layer was washed with H$_2$O and brine, dried (MgSO$_4$) and evaporated. The resulting grayish brown solid was purified by SiO$_2$ chromatography eluting with a EtOAc/hexane gradient (0 to 25% EtOAc) to afford 0.60 g (85%) of R-40.

step 2—Diethyl ether (18 mL), H$_2$O (10 mL) and solid KOH (3 g) were combined in an Erlenmeyer flask and cooled to 0° C. Nitrosourea (1.17 g, 10 equiv) was added in portions and stirred for 1 h. The ether layer was decanted onto a bed of KOH and maintained at 0° C. In a separate flask, ester R-40 (0.4 g, 1.14 mmol) and Pd(OAc)2 (0.01 g, 0.05 equiv) were dissolved in Et$_2$O (10 mL) and DCM (5 mL) and cooled to 0° C. The decanted ethereal solution of diazomethane was added to this mixture and stirred for 3 h. The solution was filtered through CELITE® and SiO$_2$ and concentrated to afford 0.40 g (95%) of R-41.

[3-(3-Chloro-5-cyano-phenoxy)-4-cyclopropyl-2-fluoro-phenyl]-acetic acid ethyl ester (R-41a) was prepared analogously except in [4-bromo-3-(3-chloro-5-cyano-phenoxy)-2-fluoro-phenyl]-acetic acid ethyl ester (R-23a) was used in place of R-24.

[3-(3-Chloro-5-cyano-phenoxy)-2-fluoro-4-methoxy-phenyl]-acetic acid (R-42b)

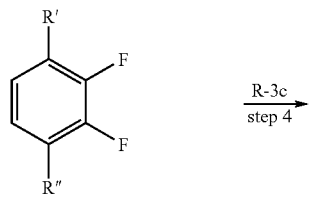

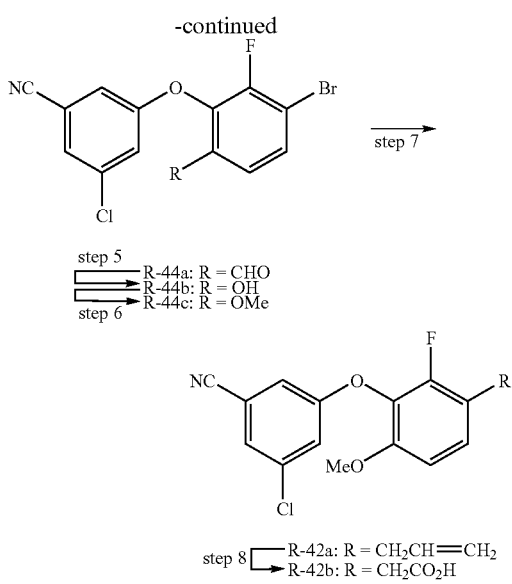

step 1—To a solution of di-iso-propylamine (150 mL, 108.3 g, 1.07 mol) in THF (500 mL) cooled to −78° C. and maintained under a N₂ atmosphere was added over a 15 min period, n-BuLi (100 mL, 1.00 mol, 10M in hexanes). The resulting mixture was stirred for 30 min at −78° C. A mixture of R-43a (45 mL, 52.110 g, 0.457 mol) and chlorotrimethylsilane (130.0 mL, 111.28 g, 1.024 mol) was added at a rate which maintained the internal reaction temperature below −50° C. The solution was stirred at −78° C. for 1 h. The reaction was quenched at −78° C. by addition of 1M $H_2SO_4$, diluted with MTBE and the mixture was saturated with solid NaCl. The phases were separated and the aqueous phase was extracted with MTBE (300 mL). The combined organic extracts were dried ($MgSO_4$), filtered and the solvents evaporated to afford 118 g (100%) of R-43b as a white solid.

step 2—To neat $Br_2$ (76.9 mL, 1.50 mol) cooled to 0° C. in an ice bath was added portion wise solid R-43b (126.23 g, 0.500 mol) while maintaining the internal temperature between 20-45° C. (caution:exothermic!). The reaction mixture was stirred at 58° C. for 2 h. After 1 h of this period had elapsed additional bromine (45.48 g) was added and the addition funnel was rinse with cyclohexane (10 mL). The reaction mixture was cooled to 0° C. and slowly poured into ice-cold saturated $NaHSO_3$ solution. After the addition the resulting mixture was saturated with solid NaCl, extracted with MTBE (500 mL and 200 mL), dried ($MgSO_4$) and concentrated in vacuo to afford 191 g of R-43c. The reaction mixture was distilled at ca. 60 mbar which afforded 161.53 g of colorless liquid which boiled at 110° C. and contained about 11% of the monobromo derivative. The product was redistilled through a bubble ball column at ca. 50 mbar which afforded 141.3 (78.5%) of R-43c with a boiling point of 93-94° C. which was >99.6 pure.

step 3—Preparation of iso-PrMgCl.LiCl—A sample of LiCl (4.56 g, 107.6 mmol) was dried under high vacuum with a heat gun for 10 min. To the dry solid under a N₂ atmosphere at 23° C. was added iso-PrMgCl (53.8 mL, 107.6 mmol, 2M solution in THF) and the resulting mixture was stirred at 23° C. for 3 days.

To a solution of R-43c (1.29 mL, 10 mmol) in THF (5 mL) at −40° C. was added the iso-PrMgCl.LiCl solution (5.5 mL, 11 mmol, 2.0M in THF) at a rate that maintained the reaction temperature below −30° C. Stirring was continued at −35 to −30° C. for 1 h then warmed to −7° C. for an additional 1 h. The reaction mixture was cooled to −30° C. and DMF (1.00 mL, 13 mmol) was added in one portion (temperature rose to −23° C.) and stirring continued for 3.5 h at −25 to +15° C. The reaction mixture was poured into 1M $H_2SO_4$ and ice and the resulting mixture was saturated with solid NaCl and twice extracted with MTBE. The combined extracts were dried ($MgSO_4$), filtered and concentrated in vacuo to afford 2.17 g (98%) of R-43d as a white solid.

step 4—To a solution of R-3c (3.84 g), $K_2CO_3$ powder (4.2 g) and n-butyl nitrile was added R-43d (5.57 g). The reaction mixture was heated to reflux for 4.5 h when the reaction appeared complete by gc/ms. The reaction mixture was cooled and poured into water and then EtOAc was added. The resulting mixture was allowed to stand until the layers separated. Some crystals were present at the interface and along the walls of the upper layer which were filtered and washed with water and hexanes. The filtrate was evaporated in vacuo, the residue taken up in IPA and re-evaporated. The solid was triturated with hexane and filtered. The mother liquor was evaporated and the residue purified by $SiO_2$ chromatography eluting with hexane/EtOAc (80:20). The product was triturated with IPA, filtered and washed with hexanes and the product fractions combined to afford 1.45 g (83%) of R-44a.

step 5—TFAA (8.88, 4.231 mmol) was added to a 100 mL round bottom and stirred at 0° C. Hydrogen peroxide (0.290, 8.46 mmol, 30%) was then added dropwise to the reaction vessel and stirred for 2 h at 0° C. to produce trifluoroperacetic acid (TFPA).

To a solution of R-44a (2.0, 5.64 mmol) in DCM (20 mL) stirred at 0° C. was added $KH_2PO_4$ (15.35 g, 112.82 mmol). To this suspension was added dropwise at 0° C. the TFPA. The reaction was stirred for 48 h. Upon consumption of starting material reaction mixture was cooled to 0° C., and diluted with brine, and quenched with aqueous 10% sodium bisulfite. The resulting mixture was extracted with DCM and washed with brine, dried ($Na_2SO_4$), filtered and the solvent removed in vacuo to yield a yellow solid which was purified by $SiO_2$ chromatography eluting with hexane/EtOAc (92:8) to afford 1.8 g (94%) of R-44b.

step 6—To a solution of R-44b (1.8 g, 5.26 mmol) in DMF (15 mL) was added $Cs_2CO_3$ (3.43 g, 10.52 mmol) and MeI (0.74 g, 5.26 mmol). The reaction mixture was stirred at 85° C. for 12 h. When R-44b was consumed, the reaction mixture was cooled to RT and the cured mixture extracted with EtOAc and the combined extracts washed with water and brine. The EtOAc was dried ($Na_2SO_4$), filtered and concentrated in vacuo to afford R-44c as a yellow oil which was used in the next step without additional purification.

step 7—A dry 100 mL round bottom was purged with nitrogen and charged with R-44c (1.6 g, 4.50 mmol) and anhydrous THF (20 mL). The mixture was cooled to −20° C. and a solution of iso-PrMgCl.LiCl (5.40 ml, 5.40 mol, 2M in THF, see step 3) was added dropwise. The reaction was stirred for 2 h at −20° C. and a solution of CuCN LiCl (0.100 mL, 0.100 mol 1 M in THF) was added and stirred continued at −20° C. To this mixture was added allyl bromide (1.08 g, 9.0 mmol) and the mixture stirred for an additional 2 h. The reaction was quenched by addition of aqueous $NH_4Cl$. The mixture extracted with EtOAc and washed with water and brine. The extracts were dried ($Na_2SO_4$), filtered and the solvent was removed in vacuo to yield a yellow oil. The crude product was purified by $SiO_2$ chromatography eluting with hexane/EtOAc (95:5) to afford 1 g (70%) of R-42a.

step 8—To a solution of R-42a (0.100 g, 0.315 mmol), EtOAc (2 mL), MeCN (2 mL) and water (3 mL) was added NaIO$_4$ (0.437 g, 2.050 mmol) and RuCl$_3$ (0.001 g, 0.006 mmol). When R-42a was consumed, the crude mixture was filtered through a pad of CELITE®, washed with EtOAc and the combined EtOAc washes were washed with brine, dried (Na$_2$SO$_4$) filtered and evaporated in vacuo to afford 0.090 g (85%) of R-42b as a yellow solid which was taken up in EtOAc and washed with brine. The EtOAc was dried (Na$_2$SO$_4$) and filtered. The solvent was removed in vacuo to yield R-42b as a yellow solid (0.090 g, 85%).

[3-(3,5-Dicyano-phenoxy)-2-fluoro-4-methoxy-phenyl]-acetic acid (R-45) and [3-(3-cyano-5-difluoromethyl-phenoxy)-2-fluoro-4-methoxy-phenyl]-acetic acid (R-46) can be prepared similarly except R-10 and R-26 respectively are used in place of 3-chloro-5-hydroxy-benzonitrile.

Example 1

3-Chloro-5-[6-chloro-2-fluoro-3-(5-phenyl-1H-pyrazol-3-ylmethyl)-phenoxy]-benzonitrile (I-4)

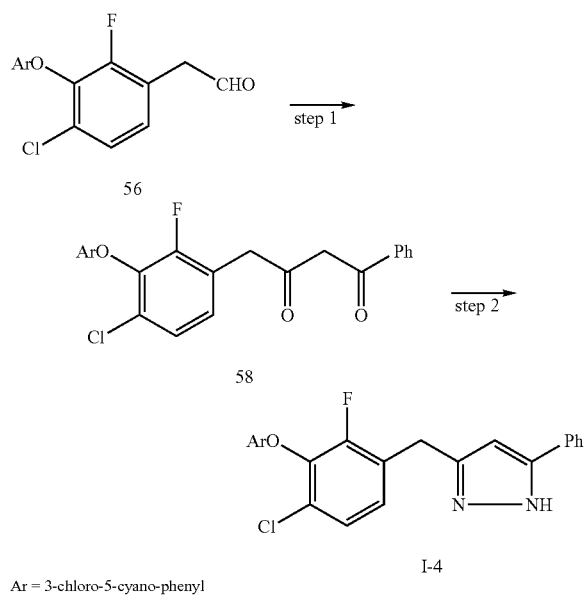

Ar = 3-chloro-5-cyano-phenyl

3-Chloro-5-[6-chloro-2-fluoro-3-(2-oxo-ethyl)-phenoxy]-benzonitrile (56) can be prepared by reduction of R-5b with diborane and resulting alcohol can be re-oxidized to the alcohol with CrO$_3$-pyridine.

step 1—To a solution of 56 (0.40 g, 1.2 mmol) in DCM (2 mL) was added a solution prepared by addition of SnCl$_2$ (0.035 g, 0.15 equiv) to a solution of phenyldiazoacetate (0.16 g, 0.9 equiv) in DCM (3 mL). The suspension was stirred at RT overnight, and more SnCl$_2$ (35 mg, 0.15 equiv) was added to the reaction mixture. After 1 h, the solution was poured into water and extracted with EtOAc and the combined organics were washed, dried (Na$_2$SO$_4$), filtered and concentrated. The product was purified by SiO$_2$ chromatography eluting with an EtOAc/hexane gradient (5% to 20% EtOAc) to afford 0.27 g (50%) of 58.

step 2—Hydrazine monohydrate (0.15 mL, 5 equiv) was added to a solution of 58 (0.27 g, 0.6 mmol) in EtOH (6 mL). The solution was heated to reflux for 1 h, and the reaction mixture was concentrated. The crude product was purified by SiO$_2$ chromatography eluting with an EtOAc/hexane gradient (10% to 40% EtOAc) to afford 0.24 g (90%) of I-4.

3-[6-Bromo-2-fluoro-3-(5-phenyl-1H-pyrazol-3-ylm-ethyl)-phenoxy]-5-difluoromethyl-benzontrile (I-5) can be prepared analogously from 3-chloro-5-[6-bromo-2-fluoro-3-(2-oxo-ethyl)-phenoxy]-benzonitrile Example 2

3-[4-Chloro-3-(3-chloro-phenoxy)-benzyl]-1H-pyrazole (I-2)

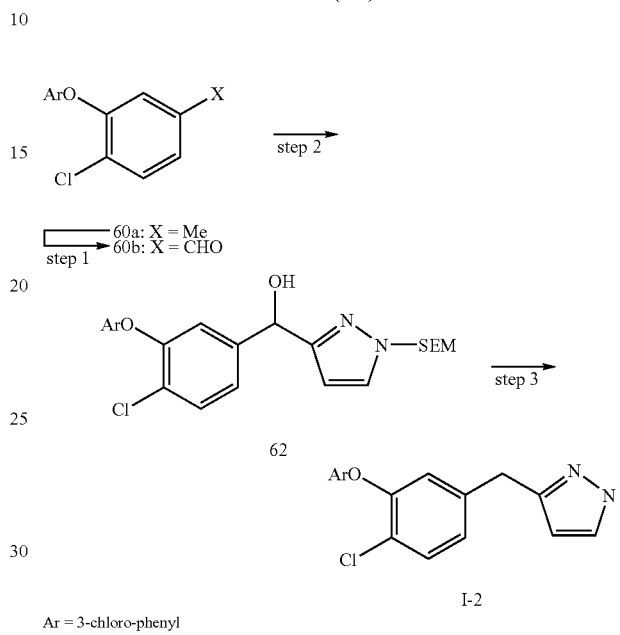

Ar = 3-chloro-phenyl step 1—A mixture of the 60a (1.37 g, 4.13 mmol), NBS (1.16 g, 6.5 mmol), and AIBN (39 mgs) in CCl$_4$ (20 mL) was refluxed under N$_2$ for 12 h. The mixture was cooled, filtered and the volatile materials were evaporated. The residue was purified by SiO$_2$ column chromatography eluting with hexanes to provide 1.26 g (74%) of the desired dibromide. The dibromide was dissolved in EtOH (40 mL), and a solution of AgNO$_3$ (2.5 g) in H$_2$O (10 mL) was added. A white precipitate formed immediately, and the mixture was heated to 100° C. for 45 min. The solution was cooled to RT, filtered through CELITE®, and concentrated. The residue was partitioned between EtOAc and water, and the organic layer was dried (Na$_2$SO$_4$), filtered, and concentrated to afford 0.91 g (100%) of 60b.

step 2—n-BuLi (2 mL of a 1.6 M solution in THF) was added dropwise to a solution of 1-(2-trimethylsilanyl-ethoxymethyl)-1H-imidazole (0.40 g, 2 mmol) in THF (2 mL) at −78° C. The solution was stirred for 5 min, and a solution of 60b (0.43 g, 1.6 mmol) in THF (2 mL) was added dropwise. The solution was warmed to 0° C., poured into ice-cold aqueous NH$_4$Cl, and extracted with EtOAc (50 mL). The organic layer was washed with brine, dried (Na$_2$SO$_4$), filtered and concentrated. The crude product was purified by SiO$_2$ chromatography eluting with an EtOAc/hexane gradient (20% to 30% EtOAc) to afford 0.37 g (51%) of 62.

step 3—A solution of con HCl (4 mL) in H$_2$O (4 mL) was added to a solution of 62 (0.37 g, 0.82 mmol) in MeOH (5 mL). The solution was heated to 65° C. for 1.5 h, cooled, and poured into ice. The mixture was neutralized with NaHCO$_3$, extracted with EtOAc, dried and concentrated. The residue was purified by a SiO$_2$ column eluting with 5% MeOH/DCM to afford 0.21 g (77%) of the deprotected pyrazole. This product (0.17 g, 0.5 mmol) was dissolved in DCM (2 mL) and Et₃SiH (2 mL) and TFA (1 mL) were added, and the mixture was stirred at 60° C. for 3 h and then at RT overnight. An additional 2 mL of EtSiH and 1 mL of TFA were added, and the mixture was heated to reflux for an additional 5 h. The solution was cooled to RT, poured onto a slurry of ice and NaHCO₃, and extracted with EtOAc. The organic layer was washed with water, dried (Na₂SO₄), and concentrated. The residue was purified by SiO₂ column chromatography eluting with 50% EtOAc/hexanes to afford 0.14 g (85%) of I-2.

Example 3

3-Chloro-5-[6-chloro-2-fluoro-3-(1H-indazol-3-ylmethyl)-phenoxy]-benzonitrile (I-3)

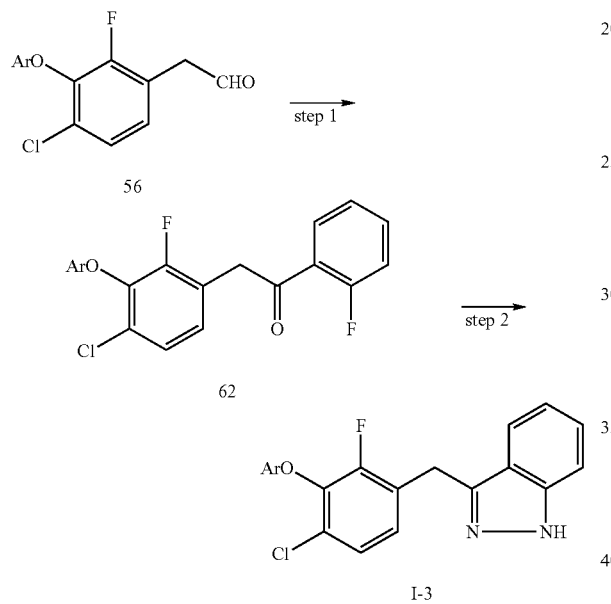

Ar = 3-chloro-5-cyano-phenyl step 1—i-PrMgCl (1.7 mL of a 2 M solution, 1.1 equiv) was added to a solution of 2-fluoro-bromobenzene (0.33 mL, 1 equiv) in THF (2 mL) cooled to 0° C. The solution was stirred at 0° C. for 1.25 h, then cooled to −78° C., and a solution of the 56 (0.99 g, 3 mmol) in THF (2 mL) was added dropwise. The reaction mixture was warmed slowly to 0° C., and added to a cold aqueous solution of NH₄Cl. The solution was extracted with ether, and the combined organics were washed, dried, filtered and concentrated in vacuo. The crude residue was purified by SiO₂ chromatography eluting with an EtOAc/hexane gradient (0% to 25% EtOAc) to afford 0.57 g (44%) of the o-fluoro-phenyl adduct. A portion of the adduct (0.26 g, 0.62 mmol) was dissolved in DCM (3 mL), and Dess-Martin periodinane (0.32 g, 1.2 equiv) was added in one portion. After 4 h, the reaction was added to a saturated aqueous solution of Na₂S₂O₄. The mixture was extracted with DCM, washed, dried, and concentrated. The crude product was purified by SiO₂ chromatography eluting with an EtOAc/hexane gradient (0% to 20% EtOAc) to afford 0.23 g (87%) of 62.

step 2—Hydrazine (0.24 mL, 10 equiv) was added to a solution of 62 (0.32 g, 0.77 mmol) in a mixture of dioxane (3.6 mL) and EtOH (0.4 mL). After 2 h, the volatile materials were removed and purification of the residue by HPLC afforded 0.04 g (13%) of I-3.

3-[6-Bromo-2-fluoro-3-(1H-indazol-3-ylmethyl)-phenoxy]-5-difluoromethyl-benzonitrile (I-6) was prepared analogously from R-25 and 2-fluorobenzoic acid utilizing the Claisen condensation/hydrazine cyclization sequence.

Example 4

3-[6-Bromo-2-fluoro-3-(7-nitro-1H-indazol-3-ylmethyl)-phenoxy]-5-chloro-benzonitrile (I-20), 3-[3-(7-Amino-1H-indazol-3-ylmethyl)-6-bromo-2-fluoro-phenoxy]-5-chloro-benzonitrile (I-35), N-{3-[4-Bromo-3-(3-chloro-5-cyano-phenoxy)-2-fluoro-benzyl]-1H-indazol-7-yl}-acetamide (I-36), N-{3-[4-Bromo-3-(3-chloro-5-cyano-phenoxy)-2-fluoro-benzyl]-1H-indazol-7-yl}-methanesulfonamide (I-38)

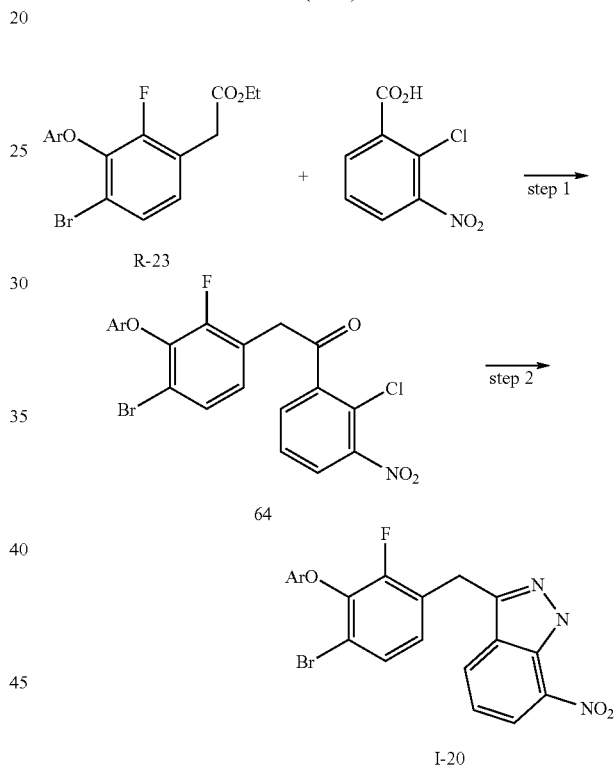

Ar = 3-chloro-5-cyano-phenyl step 1—CDI (0.16 g, 1 equiv) was added to a solution of 2-chloro-3-nitro-benzoic acid (CAS Reg No. 3970-35-2, 0.19 g, 0.92 mmol) in DMF (3 mL). The solution was heated to 50° C. for 45 min, cooled to −10° C., and a solution of the R-23a (0.40 g, 1 equiv) in DMF (2 mL) followed by NaH (0.13 g, 55% suspension in mineral oil, 3.2 equiv) was added and the reaction was warmed to RT. The reaction mixture was poured into saturated aqueous NH₄Cl and extracted with EtOAc. The organics were dried (MgSO₄), filtered and evaporated. The residue was dissolved in a mixture of DMSO (5 mL) and brine (0.3 mL), and heated at 150° C. for 20 min. The solution was poured into a saturated LiCl solution and the aqueous mixture was extracted with EtOAc, dried (MgSO₄), filtered and evaporated. The crude product was purified by SiO₂ chromatography eluting with an EtOAc/hexane gradient (5% to 50% EtOAc) to afford 0.42 g (92%) of 64.

step 2—Hydrazine (0.040 mL, 3 equiv) was added to a solution of 64 (0.22 g, 0.42 mmol) in dioxane (3 mL). After 2 h, the reaction mixture was partitioned between water and EtOAc. Evaporation of the organic layer afford an oil that was purified by SiO₂ chromatography eluting with an EtOAc/hexane gradient (50% to 100% EtOAc) to afford 0.120 g (58%) of I-20.

To a solution of I-20 (0.70 g, 0.139 mmol) in EtOH (400 µL) and H₂O (100 µL) were added NH₄Cl (0.031, 4.2 equiv) and Fe powder (0.032 g, 4.2 equiv). After heating for 30 min at 90° C. the reaction mixture was cooled to RT, filtered through CELITE®, and concentrated in vacuo. The crude product was purified by SiO₂ chromatography eluting with an EtOAc/hexane gradient (33% to 70% EtOAc) to afford 0.068 g (91%) of I-35.

To a solution of I-35 (0.017 g, 0.036 mmol) in HOAc (180 µL) was added slowly Ac₂O (0.0042 g, 1.15 equiv) in HOAc (180 µL). The resulting solution was heated to 80° C. for 30 min, then cooled to RT and concentrated in vacuo. The crude product was purified by preparative thin layer chromatography developing with (5% MeOH/DCM) to afford 0.015 g (81%) of I-36. N-{3-[4-Bromo-3-(3-chloro-5-cyano-phenoxy)-2-fluoro-benzyl]-1H-indazol-7-yl}-methanesulfonamide (I-38) was prepared similarly utilizing methanesulfonyl chloride/TEA in place of Ac₂O/HOAc.

Example 5

3-[4-Bromo-3-(3-chloro-5-cyano-phenoxy)-2-fluoro-benzyl]-1H-indazole-7-carbonitrile (I-30)

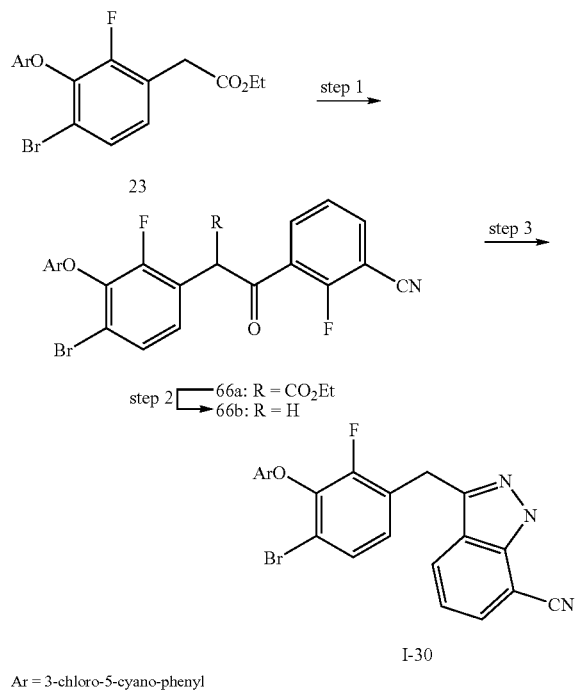

Ar = 3-chloro-5-cyano-phenyl step 1—A mixture of CDI (0.556 g, 1.1 eq.), 3-cyano-2-fluoro phenylacetic acid (0.567 g, 1.1 eq.), 23 (1.24 g, 3.12 mmol), NaH (0.240 g, 3.20 equiv.) in DMF (31 mL) were reacted as described in example 1. The crude product was purified by SiO₂ chromatography eluting with 25% EtOAc/hexane to afford 0.700 g (41%) of 66a.

step 2—A mixture of 66a (0.70 g, 1.28 mmol), DMSO (7.8 mL) and H₂O (0.4 mL) was processed as described in step 2 of example 1 to afford 0.626 g (100%) of 66b.

step 3—A mixture of 66b (0.20 g, 0.41 mmol), hydrazine (0.039 mL, 3 equiv.), EtOH (0.052 mL) and dioxane (3.5 mL) was reacted as described in step 3 of example 1 to afford 0.119 g (60%) of I-30.

Example 6

3-[6-bromo-2-fluoro-3-(1H-pyrazolo[3,4-b]pyridin-3-ylmethyl)-phenoxy]-5-chloro-benzonitrile (I-7)

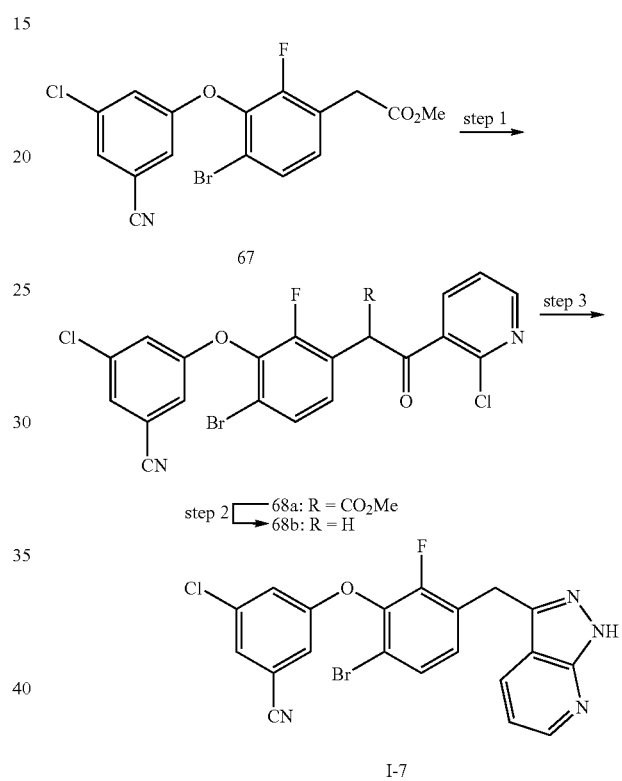

step 1—To a solution of 2-chloronicotinic acid (1.96 g, 12.5 mmol) in DMF (63 mL) was added CDI (2.02 g, 12.5 mmol) and the solution was heated to 50° C. After 2 h, the reaction mixture was cooled to −10° C., and to this was added sequentially a solution of 67 (4.51 g, 11.3 mmol) in DMF (46 mL) and solid NaH (1.45 g, 36.2 mmol). (The methyl ester 67 was prepared by the procedure described for R-23a except methyl t-butyl malonate was used in place of ethyl t-butyl malonate.) The reaction mixture was stirred at −10° C. for 15 min, then warmed to RT and stirred for 14 h. The reaction mixture was partitioned between NH₄Cl and EtOAc. The aqueous layer was extracted with EtOAc and the combined organic extracts were washed with 1N HCl, brine, dried (MgSO₄), filtered and concentrated in vacuo. The crude product was purified by column chromatography on SiO₂ eluting with an EtOAc/hexane gradient (25 to 30% EtOAc) to afford 3.25 g (53%) of 68a.

step 2—A solution of 68a (3.25 g, 6.04 mmol) in DMSO (35 mL) and H₂O (1.7 mL) was stirred in a preheated 150° C. oil bath for 30 min. The reaction mixture was partitioned between EtOAc and saturated aqueous NaHCO₃. The aqueous phase was extracted with EtOAc (3×50 mL) and the combined organic extracts were dried (MgSO₄), filtered and concentrated in vacuo to afford 2.45 g (85%) of 68b as a yellow oil.

step 3—To a solution of 68b (2.3 g, 4.8 mmol) in dioxane (41 mL) and EtOH (6 mL) was added hydrazine (1.50 mL, 10 equiv.) and the reaction mixture was heated to 100° C. After 2 h., the reaction mixture was cooled to RT and the solvent was removed. The residue was partitioned between 10% MeOH/DCM and saturated aqueous NaHCO₃. The aqueous layer was back-extracted with 10% MeOH/DCM and the combined organic extracts were dried (MgSO₄) filtered and concentrated in vacuo to afford a yellow solid that was triturated with 30% EtOAc/hexanes to afford 1.91 g (87%) of I-7 as a white solid.

3-Chloro-5-[6-chloro-2-fluoro-3-(1H-pyrazolo[3,4-b]pyridin-3-ylmethyl)-phenoxy]-benzonitrile (I-46) was prepared similarly from [4-chloro-3-(3-chloro-5-cyano-phenoxy)-2-fluoro-phenoxy]-acetic acid ethyl ester (R-5b).

5-[6-Bromo-2-fluoro-3-(1H-pyrazolo[3,4-b]pyridin-3-ylmethyl)-phenoxy]-isophthalonitrile (I-16) was prepared similarly from [4-bromo-3-(3,5-dicyano-phenoxy)-2-fluoro-phenyl]-acetic acid ethyl ester (R-39).

3-Chloro-5-[2-fluoro-6-methyl-3-(1H-pyrazolo[3,4-b]pyridin-3-ylmethyl)-phenoxy]-benzonitrile (I-24) was prepared similarly from [3-(3-chloro-5-cyano-phenoxy)-2-fluoro-4-methyl-phenyl]-acetic acid ethyl ester (R-31).

5-[6-Cyclopropyl-2-fluoro-3-(1H-pyrazolo[3,4-b]pyridin-3-ylmethyl)-phenoxy]-isophthalonitrile (I-21) was prepared similarly from [4-cyclopropyl-3-(3,5-dicyano-phenoxy)-2-fluoro-phenyl]-acetic acid ethyl ester (R-41).

-Chloro-5-[6-ethyl-2-fluoro-3-(1H-pyrazolo[3,4-b]pyridin-3-ylmethyl)-phenoxy]-benzonitrile (I-25) was prepared similarly from [3-(3,5-dicyano-phenoxy)-4-ethyl-2-fluoro-phenyl]-acetic acid ethyl ester (R-32).

3-Chloro-5-[6-cyclopropyl-2-fluoro-3-(1H-pyrazolo[3,4-b]pyridin-3-ylmethyl)-phenoxy]-benzonitrile (I-33) was prepared similarly from 3-(3-chloro-5-cyano-phenoxy)-4-cyclopropyl-2-fluoro-phenyl]-acetic acid ethyl ester (R-41).

3-[6-Chloro-2-fluoro-3-(1H-pyrazolo[3,4-b]pyridin-3-ylmethyl)-phenoxy]-5-difluoromethyl-benzonitrile (I-28) was prepared similarly from [4-chloro-3-(3-cyano-5-difluoromethyl-phenoxy)-2-fluoro-phenyl]-acetic acid ethyl ester (R-16).

3-[6-Bromo-2-fluoro-3-(1H-pyrazolo[3,4-b]pyridin-3-ylmethyl)-phenoxy]-5-difluromethyl-benzonitrile (I-29) was prepared similarly from [4-bromo-3-(3-cyano-5-difluoromethyl-phenoxy)-2-fluoro-phenyl]-acetic acid ethyl ester (R-25).

3-Difluoromethyl-5-[2-fluoro-6-methyl-3-(1H-pyrazolo[3,4-b]pyridin-3-ylmethyl)-phenoxy]-benzonitrile (I-40) was prepared similarly from [3-(3-cyano-5-difluoromethyl-phenoxy)-2-fluoro-4-methyl-phenyl]-acetic acid ethyl ester (R-33).

5-[6-Ethyl-2-fluoro-3-(1H-pyrazolo[3,4-b]pyridin-3-ylmethyl)-phenoxy]-isophthalonitrile (I-45) was prepared similarly from [3-(3,5-dicyano-phenoxy)-4-ethyl-2-fluoro-phenyl]-acetic acid ethyl ester (R-36).

3-[6-Bromo-2-fluoro-3-(6-methoxy-1H-pyrazolo[3,4-b]pyridin-3-ylmethyl)-phenoxy]-5-chloro-benzonitrile (I-22) was prepared similarly except in step 1, 2-chloronicotinic acid was replaced with 2-chloro-6-methoxynicotinic acid.

3-[6-Bromo-2-fluoro-3-(5-fluoro-1H-pyrazolo[3,4-b]pyridin-3-ylmethyl)-phenoxy]-5-chloro-benzonitrile (I-23) was prepared similarly except in step 1, 2-chloronicotinic acid was replaced with 2-chloro-5-fluoro-nicotinic acid.

3-Difluoromethyl-5-[2-fluoro-6-methoxy-3-(1H-pyrazolo[3,4-b]pyridin-3-ylmethyl)-phenoxy]-benzonitrile (I-27) was prepared similarly from the methyl ester of [3-(3-3hloro-5-cyano-phenoxy)-2-fluoro-4-methoxy-phenyl]-acetic acid (R-42b).

Example 7

3-[6-Bromo-2-fluoro-3-(1H-pyrazolo[3,4-b]pyridin-3-ylmethyl)-phenoxy]-5-chloro-benzonitrile (I-7) via Grignard Route

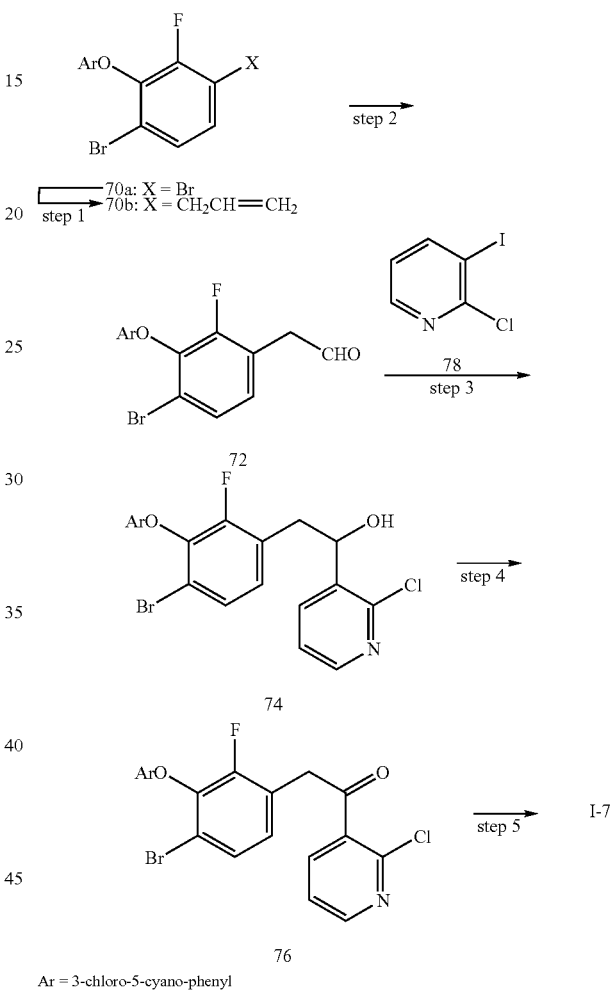

Ar = 3-chloro-5-cyano-phenyl step 1—To a solution of 70a (8.0 g, 19.7 mmol) in toluene at −78 C was added slowly i-PrMgCl (1.23 mL of a 2M solution a solution in THF). The mixture was aged for 4.5 h, and a solution of CuCN.2LiCl (4 mL of a 1 M solution in THF) was added and the reaction mixture was warmed to −30° C. for 15 min. The solution was cooled to −50° C. and allyl bromide (3.41 mL, 2 equiv) was added quickly. The mixture was warmed to RT, poured into NH₄Cl solution, and extracted with Et₂O. The organic extracts were washed with brine and dried (MgSO₄) and evaporated. The crude product was purified by SiO₂ chromatography eluting with 5% EtOAc/hexane to afford 5.5 g (76%) of 70b.

step 2—Ozone was bubbled slowly through a solution of 70b (5.8 g, 15.8 mmol), DCM (105 mL) and MeOH (55 mL) cooled to −78 C. After 40 min, the solution turned blue, bubbling of the ozone was stopped and nitrogen was bubbled through the reaction mixture for 15 min. Me₂S (11.6 mL, 10 equiv) was added via syringe, and the solution was warmed to 0° C. and aged for 2 h. The solution was evaporated and loaded directly onto SiO₂ which was applied to an SiO₂ column and eluted with an EtOAc/hexane gradient (10% to 35% EtOAc) to afford 4.2 g (72%) of 72.

step 3—A THF solution of i-PrMgCl (1 equiv of a 2M solution) was added dropwise to a solution of 78 (0.23 g, 0.96 mmol) in THF (3 mL) cooled to −40° C. and maintained under N₂. The solution was stirred for 30 min, and a solution of the 72 (0.35 g, 1 equiv) in THF (3 mL) was added dropwise. The reaction mixture was warmed to 0° C., aged for 1 h, and added dropwise to a pH 7 buffered aqueous solution. The aqueous mixture was extracted with EtOAc, the combined extracts were washed with brine, dried (MgSO₄) and concentrated in vacuo. The crude product was purified by SiO₂ chromatography eluting with an EtOAc/hexane gradient (0% to 35% EtOAc) to afford 0.21 g (45%) of 74.

step 4—To a solution of the 74 (0.77 g, 0.1.9 mmol) in DCM (9 mL) cooled to 0° C. was added the Dess-Martin periodinane (0.81 g, 1.2 equiv). The mixture was stirred for 4 h, quenched with NaHCO₃ (1 g) and the organic phase was separated and evaporated. The remaining solid was purified by SiO₂ chromatography eluting with a EtOAc/hexane gradient (0% to 35% EtOAc) to afford 0.48 g (62%) of I-7 identical to that obtained by the route depicted in example 6.

Example 8

3-[6-Bromo-2-fluoro-3-(6-oxo-6,7-dihydro-1H-pyrazolo[3,4-b]pyridin-3-ylmethyl)-phenoxy]-5-chlorobenzonitrile (I-12)

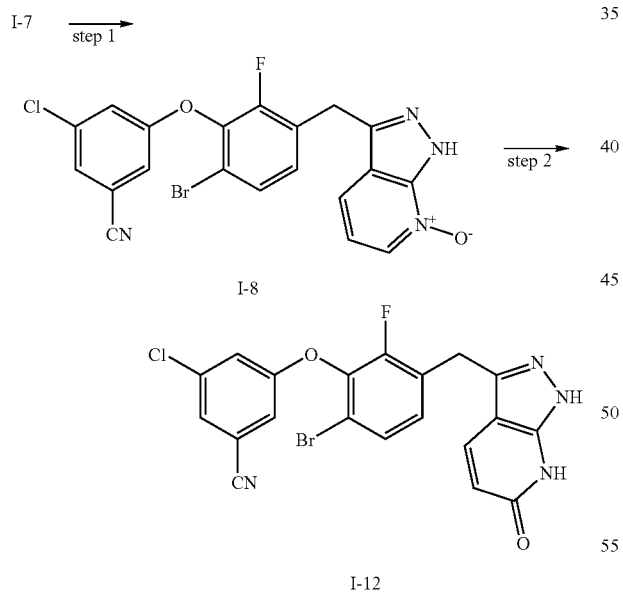

step 1—The pyrazolopyridine I-7 (0.10 g, 0.22 mmol) was suspended in DCM (4 mL). MCPBA (0.055 g, 1.1 equiv) was added and the suspension was stirred overnight. Additional MCPBA (30 mg) in DCM (4 mL) was added to the reaction mixture. After 2 h, the solvent was removed, and the remaining solid was triturated with Et₂O, collected by filtration, and washed with 10 mL of Et₂O to afford 0.90 g of I-8.

step 2—To a solution of I-8 (0.100 g, 0.212 mmol) in DCM (1 mL) cooled to 0° C. was added TFAA (0.562 mL). After 1 h, the solvent was removed to afford a foamy brown solid which was purified by reverse phase chromatography to afford 0.010 g (10%) of I-12 as a white solid.

3-[6-Bromo-2-fluoro-3-(5-fluoro-7-oxy-1H-pyrazolo[3,4-b]pyridin-3-ylmethyl)-phenoxy]-5-chloro-benzonitrile (I-26) and 3-[6-bromo-2-fluoro-3-(5-fluoro-6-oxo-6,7-dihydro-1H-pyrazolo[3,4-b]pyridin-3-ylmethyl)-phenoxy]-5-chloro-benzonitrile (I-34) were prepared analogously from I-23.

Example 9

3-[6-Bromo-2-fluoro-3-(7-methyl-6-oxo-6,7-dihydro-1H-pyrazolo[3,4-b]pyridin-3-ylmethyl)-phenoxy]-5-chloro-benzonitrile (I-48)

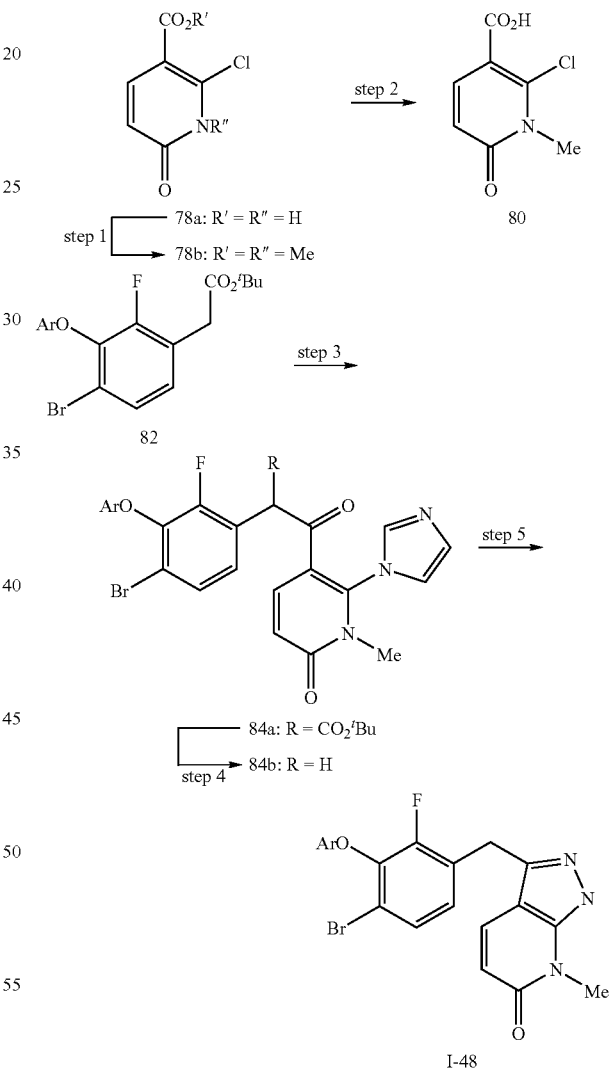

Ar = 3-chloro-5-cyano-phenyl

2-Chloro-6-oxo-1,6-dihydro-pyridine-3-carboxylic acid was prepared as described by A. G. Beaman and O. N. Miller in U.S. Pat. No. 3,682,932.

step 1—Trimethylsilyl diazomethane (27.6 mL, 2M hexanes, 6 equiv) was carefully added over 10 min to an ice-cold solution of 78a (1.60 g, 9.20 mmol) in DCM (45 mL) and MeOH (45 mL). The reaction mixture was quenched with HOAc, and concentrated in vacuo. The product was purified by SiO$_2$ chromatography eluting with an EtOAc/DCM gradient (5 to 10% EtOAc) to afford 1.25 g (68%) of 78b.

step 2—A solution of LiOH.H$_2$O (54 mg, 1.2 equiv) in H$_2$O (3.3 mL) was added slowly of 78b (0.200 g, 1.1 mmol) in THF (10 mL) at RT. After stirring 15 h the reaction mixture was acidified to pH 1 with 2M HCl, diluted with water and extracted with EtOAc. The combined extracts were washed with brine, dried (MgSO$_4$) and concentrated in vacuo to provide 0.180 g slightly impure 80.

steps 3 & 4—To a solution of 80 (0.120 g, 0.691 mmol) in DMF (1.2 mL) was added CDI (0.123 g, 1.1 equiv) in one portion. After heating for 30 min at 50° C. the solution was cooled to 0° C. and a solution 82 (0.335 g, 1.1 equiv) in DMF (2.3 mL) was introduced. NaH (0.094 g, 60% in oil, 3.4 equiv) was added slowly in one portion and the reaction mixture was allowed to warm to RT over 2 h. The mixture was re-cooled to 0° C., quenched with saturated NH$_4$Cl, diluted with water, and extracted with EtOAc. The combined extracts were washed with brine, dried (MgSO$_4$) and concentrated in vacuo. The residue was re-dissolved in DCM (6.9 mL) and TFA (3.5 mL) and stirred for 15 h and concentrated in vacuo. The crude product was purified by SiO$_2$ chromatography eluting with a MeOH/DCM gradient (1% to 5% MeOH) to afford 0.225 g (60%) of 84b.

step 5—Hydrazine (40 µL, 3 equiv) was slowly added to a solution of 84b (0.225 g, 0.420 mmol) in 1,4-dioxane (4.2 mL) at RT. After 1 h, the reaction mixture was concentrated and purified by SiO$_2$ chromatography eluting with a MeOH/DCM gradient (1 to 5% MeOH) to afford 0.087 g (43%) of I-48.

Example 10

3-[4-Bromo-3-(3-chloro-5-cyano-phenoxy)-2-fluoro-benzyl]-1H-pyrazolo[3,4-b]pyridine-6-carbonitrile (I-14)

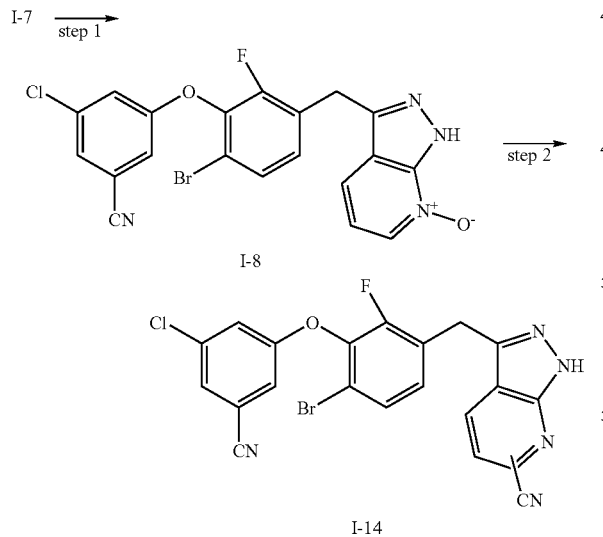

step 1—I-7 was converted to I-8 in 85% yield as described in step 1 of example 8 (85%).

step 2—To a solution of I-8 (0.120 g, 0.253 mmol) in DMF (6 mL) was added sequentially NaCN (0.050 g, 1.01 mmol), TEA (0.17 5mL, 5 equiv.) and TMSCl (0.128 mL, 4 equiv.). The resulting brown reaction mixture was heated to 110° C. for 5 h. The reaction mixture was partitioned between H$_2$O and EtOAc and the organic layer was dried (MgSO$_4$), filtered and concentrated in vacuo. The crude product was purified by column chromatography on SiO$_2$ eluting with a MeOH/DCM (both containing 1% concentrated NH$_4$OH) gradient to afford 0.018 g (15%) of I-14.

Example 11

3-[6-bromo-2-fluoro-3-(1-methyl-1H-pyrazolo[3,4-b]pyridin-3-ylmethyl)-phenoxy]-5-chloro-benzonitrile (I-17)

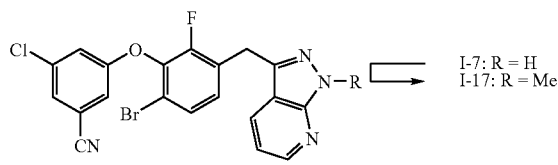

To a solution of I-7 (0.100 g, 0.218 mmol) in DMF (2 mL) cooled to 0° C. was added sequentially NaH (0.010 g, 1.2 equiv.) and MeI (0.016 mL, 1.2 equiv, dropwise). After 1 h, the reaction mixture was gradually warmed to RT and stirred for 16 h. The reaction mixture was partitioned between aqueous NH$_4$Cl and EtOAc. The organic layer was washed with 1N HCl, the aqueous layer was back-extracted with EtOAc, the combined organic extracts were dried (MgSO$_4$), filtered and evaporated. The crude product was purified by SiO$_2$ chromatography eluting with EtOAc/hexanes (20% EtOAc) to afford 0.055 g (53%) of I-17.

Example 12

3-[6-Bromo-2-fluoro-3-(1H-pyrazolo[3,4-c]pyridin-3-ylmethyl)-phenoxy]-5-chloro-benzonitrile (I-15)

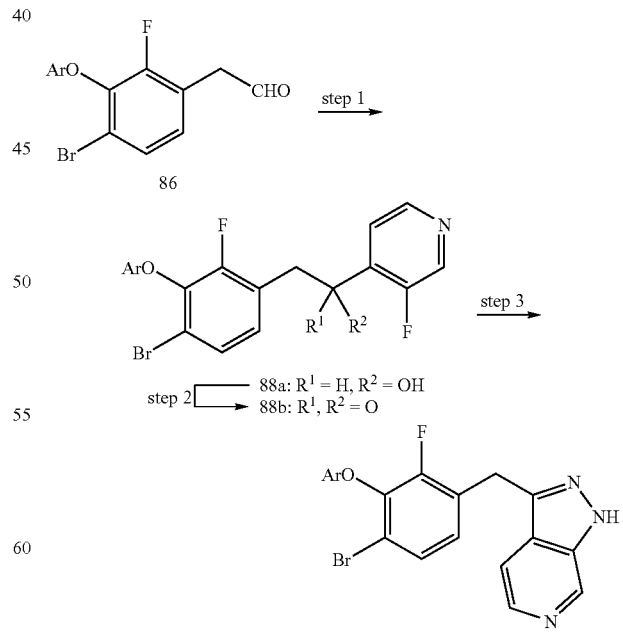

Ar = 3-chloro-5-cyano-phenyl step 1 & 2—were carried out as described in steps 3 & 4 of example 7 except in step 3, 3-fluoro-4-iodopyridine was used in place of 2-chloro-3-iodo-pyridine.

step 3—Hydrazine (0.288 mL, 5 equiv) was added to a solution of 88b (0.85 g, 1.8 mmol) in dioxane (9 mL) and EtOH (0.5 mL). The solution was heated to 80° C. for 3 h. The solution was partitioned between EtOAc and water. Separation of the organic layer and evaporation of the residue afforded an oil that was purified by SiO$_2$ chromatography eluting with a MeOH/DCM gradient (0% to 5% MeOH) to afford 0.24 g (29%) of I-15.

5-[6-Bromo-2-fluoro-3-(1H-pyrazolo[3,4-c]pyridin-3-yl-methyl)-phenoxy]-isophthalonitrile (I-19) was prepared similarly starting from [4-bromo-3-(3,5-dicyano-phenoxy)-2-fluoro-phenyl]-acetic acid ethyl ester (R-39).

3-[6-Bromo-2-fluoro-3-(1H-pyrazolo[3,4-c]pyridin-3-yl-methyl)-phenoxy]-5-difluoromethyl-benzonitrile (I-31) was prepared similarly starting from [4-bromo-3-(3-cyano-5-difluoromethyl-phenoxy)-2-fluoro-phenyl]-acetic acid ethyl ester (R-25).

3-[6-Chloro-2-fluoro-3-(1H-pyrazolo[3,4-c]pyridin-3-yl-methyl)-phenoxy]-5-difluoromethyl-benzonitrile (I-32) was prepared similarly from [4-chloro-3-(3-cyano-5-difluoromethyl-phenoxy)-2-fluoro-phenyl]-acetic acid ethyl ester (R-16).

Example 13

3-[6-Bromo-2-fluoro-3-(1H-pyrazolo[3,4-d]pyrimidin-3-ylmethyl)-phenoxy]-5-chloro-benzonitrile (I-18)

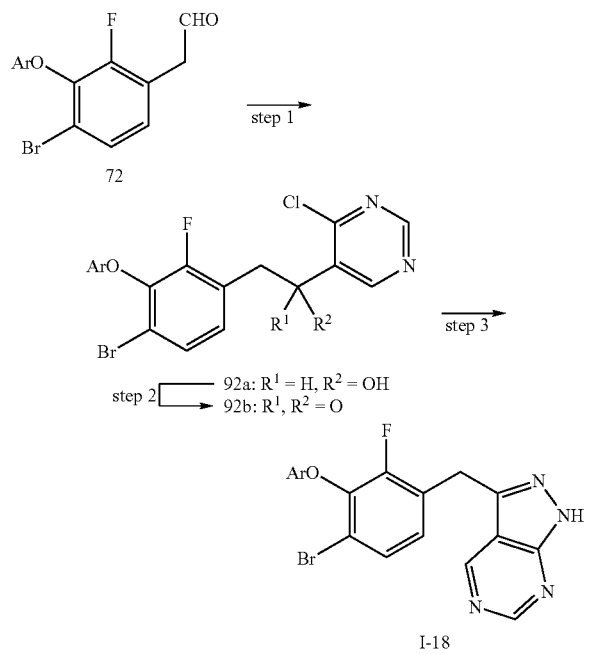

Ar = 3-chloro-5-cyano-phenyl step 1—5-bromo-4-chloro-pyrimidine (0.890 g, 1.0 equiv) was dissolved in toluene (40 mL) and cooled to −40° C. Isopropylmagnesium chloride (2.5 mL, 1.1 equiv) was added dropwise and the solution stirred at −20° C. for 1 h. A solution of 72 (1.7 g, 4.6 mmol) and toluene (8 mL) was added to the reaction mixture. The solution was stirred at 0° C. for 3 h, poured into NH$_4$Cl and extracted with EtOAc. The organic layer was washed with brine, dried (Na$_2$SO$_4$), and concentrated in vacuo. The product was purified by SiO$_2$ chromatography eluting with an EtOAc/hexane gradient (0-40%) to afford 0.35 g (16%) of 92a as a white solid.

step 2—To a solution of 92a (0.35 g, 0.73 mmol) and DCM (5 mL) and cooled to 0° C. was added Dess-Martin periodinane (0.374 g, 1.2 equiv). The resulting brown solution was stirred at 0° C. for 4 h and evaporated. The product was purified by SiO$_2$ chromatography eluting with an EtOAc/hexane gradient (0 to 30% EtOAc) to afford 0.220 g (63%) of 92b as a yellow oil.

step 3—To a solution of 92b (0.22 g, 0.456 mmol), dioxane (5 mL) and EtOH (0.7 mL) was added hydrazine (0.075 mL, 5 equiv) via syringe. The reaction was stirred for 3 h, poured into NH$_4$Cl, and extracted with 10% MeOH/DCM. The organic layer was washed with brine, and dried (Na$_2$SO$_4$) and evaporated to afford an off-white solid that was triturated with 70% EtOAc/hexanes to yield 0.035 g (15%) of I-18 as a white powder.

3-[6-Bromo-3-(6-chloro-1H-pyrazolo[3,4-d]pyrimidin-3-ylmethyl)-2-fluoro-phenoxy]-5-chloro-benzonitrile (I-13) was prepared similarly except in step 1, 5-bromo-2,4-dichloro-pyrimidine was used in place of 5-bromo-4-chloro-pyrimidine The final cyclization with hydrazine was carried out as follows:

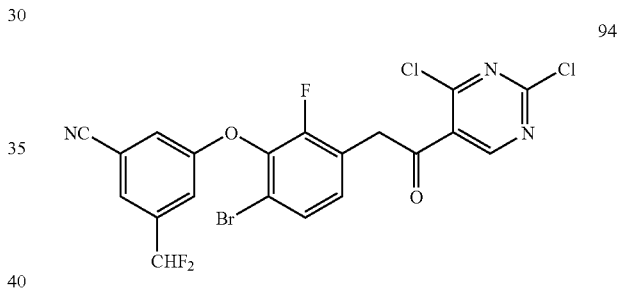

step 3—DIPEA (15 µL) was added to a solution of 94 (0.25 g, 0.5 mmol) in dioxane (3 mL). Hydrazine (15 µL, 1 equiv) was slowly added to the solution, followed by additional DIPEA (200 µL). After 2 h, the solution was poured into water, and the aqueous mixture was extracted with EtOAc. The organics were dried (MgSO$_4$), filtered and evaporated to provide a residue that was purified by SiO$_2$ chromatography eluting with an EtOAc/hexane gradient (20% to 70%) to afford 0.18 g (76%) of I-13.

Example 14

3-[3-(7-Amino-1H-pyrazolo[3,4-c]pyridin-3-ymethyl)-6-bromo-2-fluoro-phenoxy]-5-chloro-benzonitrile (I-41, Scheme D)

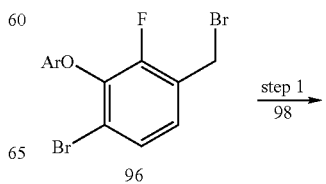

-continued

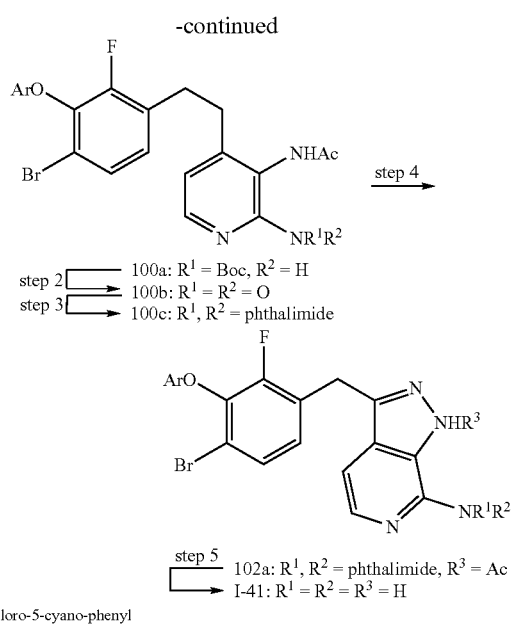

Ar = 3-chloro-5-cyano-phenyl (3-Acetylamino-4-methyl-pyridin-2-yl)-carbamic acid tert-butyl ester (98) was prepared in three steps from 2-amino-4-methyl-3-nitropyridine by the procedure of Townsend (*Heterocycles* 2002 57:2335-2343).

3-(6-Bromo-3-bromomethyl-2-fluoro-phenoxy)-5-chloro-benzonitrile (96) was prepared in four steps as described below:

Sodium hydride (42 mg, 60 wt % suspension, 1.05 equiv) was added to a solution of the R-3c (153 mg, 1 mmol) in dimethylacetamide (1 mL). The solution was aged at 50° C. for 30 min, and R-43c (2.7 g, 10 equiv) was added. The solution was warmed to 125° C. for 2 h, and then cooled to RT. The reaction mixture was diluted with EtOAc and washed with 10% $H_2SO_4$. Concentration of the organic layer and purification by $SiO_2$ chromatography eluting with 10% EtOAc/hexane afforded 0.331 g (82%) of 3-chloro-5-(3,6-dibromo-2-fluoro-phenoxy)-benzonitrile (103).

A solution of i-PrMgCl (17.3 mL of a 2 M solution in THF, 1.75 equiv) was added slowly to a solution of the 103 (8.0 g, 19.7 mmol) in toluene (160 mL) at −78 C. The solution was aged for 1.5 h then transferred by cannula to a flask containing DMF (2.3 mL, 1.5 equiv) in toluene (30 mL). The solution was quenched with aqueous $NH_4Cl$, and diluted with EtOAc. The organic layer was separated, washed with brine, dried, and evaporated. The crude product was purified by $SiO_2$ by chromatography eluting with 20% EtOAc/hexanes to afford 6.5 g (98%) of 3-(6-bromo-2-fluoro-3-formyl-phenoxy)-5-chloro-benzonitrile (105) as a yellow solid.

$NaBH_4$ (0.64 g, 1.5 equiv) was added portionwise to a stirred solution of 105 (4.0 g, 11.3 mmol) in a mixture of THF (20 mL) and MeOH (10 mL) at RT. The reaction mixture was stirred for 12 h, and quenched by the addition of saturated aqueous $NH_4Cl$. The aqueous mixture was extracted with EtOAc, and the organic solution was washed with water and evaporated. The crude product was purified by $SiO_2$ chromatography eluting with an EtOAc/hexane gradient (20% to 50% EtOAc) to afford 1.9 g (47%) of 3-(6-bromo-2-fluoro-3-hydroxymethyl-phenoxy)-5-chloro-benzonitrile (107) as a yellow oil.

A solution of $PBr_3$ (0.74 mL of a 1 M solution in DCM, 1.1 equiv) was added to a solution of 107 (0.24 g, 0.67 mmol) in DCM (5 mL). The mixture was stirred at RT for 1 h and then concentrated in vacuo. The residue was dissolved in EtOAc, washed with saturated aqueous $NaHCO_3$, and dried ($MgSO_4$). Evaporation of the volatile materials afforded 0.17 g (60%) of 96.

steps 1 & 2—BuLi (6.35 mL, 2.5M hexanes, 4 equiv) was added slowly to a solution of 98 (1.05 g, 3.97 mmol) in THF (100 mL) cooled to −78° C. After 15 min the solution was warmed to 0° C. for 15 min then re-cooled to −78° C. The bromide 96 (2.5 g, 1.5 equiv) in THF (15 mL) was slowly added to the reaction mixture and stirred to RT over 2 h. The mixture was then re-cooled to 0° C., quenched with saturated $NH_4Cl$, diluted with water, and extracted with EtOAc. The organic extracts were washed with brine, dried ($MgSO_4$), and concentrated in vacuo. The crude product was purified by $SiO_2$ chromatography eluting with a EtOAc/hexane gradient (20% to 75% EtOAc) which afforded 0.700 g of partially purified 100a. The residue obtained was re-dissolved in DCM (21.5 mL) and treated with TFA (830 μL) for 15 h. The reaction mixture was concentrated in vacuo and purified by $SiO_2$ chromatography eluting with a MeOH/DCM gradient (3% to 9% MeOH) to afford 0.220 g of partially purified 100b.

step 3—To a solution of 100b (0.200 g, ca 0.397 mmol) from step 3 and DCM (4 mL) cooled to 0° C. was added TEA (330 μL, 6 equiv) followed by phthaloyl dichloride (100 μL, 1.7 equiv) and the reaction mixture was warmed to RT. After 1 hr, saturated $NH_4Cl$ was added, the mixture was diluted with $H_2O$ and then extracted with EtOAc. The organic layers were washed with brine, dried ($MgSO_4$), and concentrated in vacuo. The product was purified by $SiO_2$ chromatography eluting with an EtOAc/hexane gradient to afford 0.110 g (44%, 4% over 3 steps) of 100c.

step 4—Potassium acetate (26 mg, 1.5 equiv) and $Ac_2O$ (50 μL, 3 equiv) were added to a solution of 100c (0.110 g, 0.174 mmol) in benzene (2.3 mL). The solution was heated to 80° C. and iso-amylnitrite (32 μL, 1.4 equiv) was added slowly. The temperature was increased to 95° C. and after 4 h another portion of KOAc, $Ac_2O$, and iso-amylnitrite was added. After 14 h the solution was cooled to RT, filtered through CELITE®, and concentrated in vacuo. The product was purified by $SiO_2$ chromatography eluting with an EtOAc/hexane gradient (33% to 66% EtOAc) to afford 0.100 g (89%) of 102a as a 2:1 mixture of acetamide regioisomers.

step 5—Hydrazine (7.9 μL, 2.2 equiv) was slowly added to a solution of 102a (0.074 g, 0.114 mmol) in EtOH (2.3 mL). At 1 h the reaction mixture was diluted EtOH (500 μL). After 2 h the solution diluted with EtOAc, filtered through CELITE®, and concentrated in vacuo. The crude product was purified by preparative HPLC to afford 0.019 g (19%) of I-41.

Example 15

3-[6-Bromo-2-fluoro-3-(7-methoxy-1H-pyrazolo[3,4-c]pyridin-3-ylmethyl)-phenoxy]-5-chloro-benzonitrile (I-39, Scheme D)

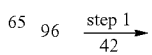

61

-continued

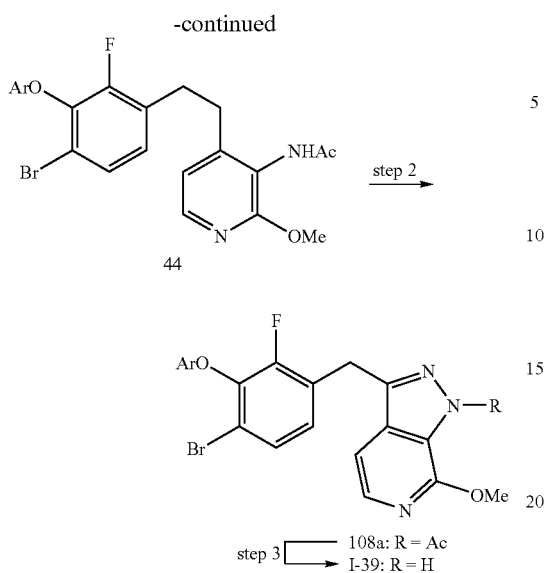

Ar = 3-chloro-5-cyano-phenyl

3-Acetamido-2-methoxy-4-methyl-pyridine (42) was prepared in 3 steps from 2-chloro-4-methyl-3-nitropyridine by the procedure of Townsend et al. (*SynLett*. 2002, 9:1479-1482).

step 1—n-Butyl lithium (3.1 mL, 2.5M hexanes, 2.1 equiv) was slowly added to a solution of 42 (0.665 g, 3.69 mmol) in THF (37 mL) at −78° C. After 15 min the solution was warmed to −50° C. for 2 h. A solution of 96 (2.32 g, 1.5 equiv) in THF (17 mL) was added slowly and the reaction mixture was stirred to 0° C. for 2 h. The mixture was quenched with saturated $NH_4Cl$, diluted with water, and then extracted with EtOAc. The combined organic layers were washed with brine, dried ($MgSO_4$), and concentrated in vacuo. The product was purified by $SiO_2$ chromatography eluting with a MeOH/DCM gradient (1% to 5% MeOH) to afford 0.077 g (4%) of 44.

step 2—Potassium acetate (10.2 mg, 1.2 equiv) and $Ac_2O$ (27.4 mg, 3.1 equiv) were added to a solution of 44 (4.5 mg, 0.0.087 mmol) in benzene (1.7 mL). The solution was heated at 80° C. and then iso-amylnitrite (32 µL, 1.6 equiv) was added slowly. The reaction mixture was then heated to 95° C. for 6 h, cooled to RT, filtered through CELITE®, and concentrated in vacuo. The crude product was purified by preparative $SiO_2$ TLC and developed with (50% EtOAc/hexanes) to afford 0.021 g (50%) 108a as a 2:1 mixture of acetamide regioisomers.

step 3—A solution of $LiOH.H_2O$ (1.3 mg, 1.1 equiv) in $H_2O$ (300 µL) was slowly added to a solution of 108 (0.015 g, 0.028 mmol) in THF (300 µL) at 0° C. After 30 min saturated $NH_4Cl$ was added, the mixture was diluted with water and extracted with EtOAc. The combined extracts were washed with brine, dried ($MgSO_4$), and concentrated in vacuo. The crude product was purified by preparative $SiO_2$ TLC and developed with 33% EtOAc/hexanes to afford 0.002 g (13%) of I-39.

62

Example 16

3-Chloro-5-[6-chloro-3-(7-chloro-1H-pyrazolo[3,4-c]pyridin-3-ylmethyl)-2-fluoro-phenoxy]-benzonitrile (I-42) and 3-[4-Chloro-3-(3-chloro-5-cyano-phenoxy)-2-fluoro-benzyl]-1H-pyrazolo[3,4-c]pyridine-7-carbonitrile (I-43)

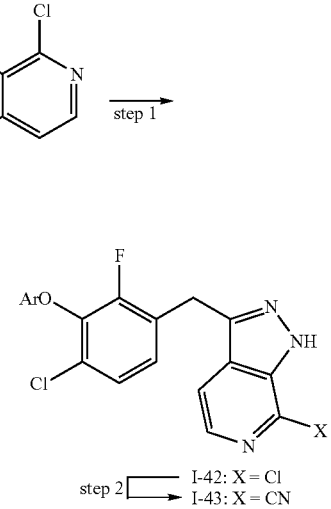

Ar = 3-chloro-5-cyano-phenyl

The ketone 110 was prepared from 2-chloro-3-fluoro-isonicotinic acid and R-5b by the procedure described in step 1 of example 4.

step 1—The ketone 110 (0.50 g, 1.10 mmol) was dissolved in dioxane (10 mL) and EtOH (1.4 mL) and hydrazine (0.042 g, 1.1 equiv) was added by syringe. The reaction was stirred at 70° C. for 4 h. The solution was cooled to RT and poured into aqueous $NaHCO_3$, and extracted with 10% MeOH/DCM. The organic layer was washed with brine, dried ($MgSO_4$) and evaporated to afford 0.340 g (70%) of I-42.

step 2—A flask containing I-42 (0.033 g, 0.074 mmol), $Zn(CN)_2$ (0.0052 g, 0.6 equiv), Zn metal (0.0029 g, 0.6 equiv), Pd(dba)3 (0.007 g, 0.1 equiv), dppf (0.0082 g, 0.2 equiv) and DMA was heated to 105° C. for 3 h. The mixture was filtered and evaporated and the crude material purified by preparatory $SiO_2$ TLC (0-15% MeOH/DCM) to afford 0.005 g (15%) of I-43.

5-[6-Chloro-3-(7-cyano-1H-pyrazolo[3,4-c]pyridin-3-ylmethyl)-2-fluoro-phenoxy]-isophthalonitrile (I-44) was prepared analogously starting from [4-chloro-3-(3,5-dicyano-phenoxy)-2-fluoro-phenyl]-acetic acid ethyl ester (R-11c).

Example 17

3-[6-Bromo-3-(6-chloro-1H-pyrazolo[3,4-b]pyridin-3-ylmethyl)-2-fluoro-phenoxy]-5-chloro-benzonitrile (I-9)

To a solution of 3-[6-bromo-2-fluoro-3-(2-oxo-ethyl)-phenoxy]-5-chloro-benzonitrile (72, 0.35 g, 0.96 mmol) in THF was added a solution of the Grignard reagent formed from i-PrMgCl (0.52 mL of a 2 M solution, 1.1 equiv) and 3-iodo-2,6-dichloropyridine (0.28 g, 1.05 equiv) as described in example 2. The reaction afford 0.28 (57%) of product after chromatographic purification. Oxidation of the resulting alcohol with Dess-Martin periodinane (47%) was carried out as described in step 4 of example 7 and cyclization with hydrazine (39%) as described in step 3 of example 6 afforded I-9.

Example 18

3-[6-Bromo-2-fluoro-3-(6-methoxy-1H-pyrazolo[3,4-b]pyridin-3-ylmethyl)-phenoxy]-5-chloro-benzonitrile (I-22)

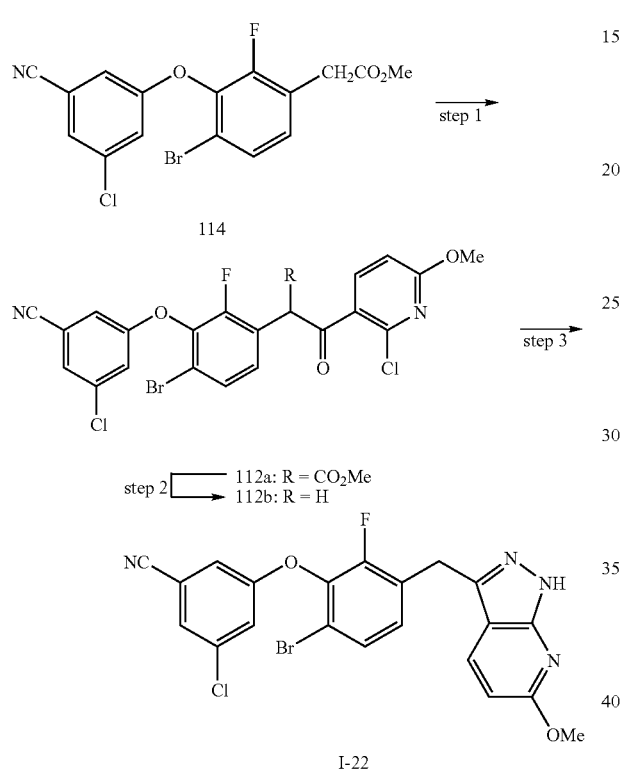

step 1—2-Chloro-6-methoxy nicotinic acid (0.23 g, 1.1 eq) was combined with CDI (0.20 g, 1.1 eq) in DMF (5 mL) and heated at 50° C. for 1 h. The reaction was cooled to −10° C. and a solution of 114 (0.45 g, 1.13 mmol) and DMF (5mL) and was added followed by NaH (0.14 g, 3.2 eq). After addition the reaction stirred at RT for 3 h. The reaction mixture was poured into saturated aqueous NH$_4$Cl, extracted with EtOAc/hexanes (1:1, 50 mL), washed with H$_2$O and brine, dried (MgSO$_4$) and concentrated in vacuo. The crude product was purified by SiO$_2$ chromatography eluting with an EtOAc/hexane gradient (0-15% EtOAc) to afford 0.35 g (54%) of 112a as a white solid.

step 2—A solution of 112a, DMSO (3 mL) and H$_2$O (0.15 mL) was heated at 150° C. for 2 h. The reaction was cooled to RT, poured into saturated LiCl solution, and extracted with EtOAc. The combined extracts were washed with water and brine, dried (Na$_2$SO$_4$) and concentrated in vacuo. The crude product was purified by SiO$_2$ chromatography eluting with an EtOAc/hexane gradient (0-12% EtOAc) to afford 0.200 g (35% overall for steps 1 and 2) of 112b as a white solid.

step 3—To a solution of 112b (0.2 g, 0.392 mmol) in dioxane (5 mL) and EtOH (0.7 mL) was added hydrazine (0.086 mL, 7.0 eq.) via syringe. The reaction was stirred at 80° C. for 2.5 h. The solution was cooled to RT and poured into aqueous NH$_4$Cl and extracted with 10% MeOH/DCM. The combined extracts were washed with brine, dried (Na$_2$SO$_4$), and evaporated to afford 0.087 g (46%) of I-22.

Example 19

3-[6-Bromo-2-fluoro-3-(5-fluoro-7-oxy-1H-pyrazolo[3,4-b]pyridin-3-ylmethyl)-phenoxy]-5-chloro-benzonitrile (I-34)

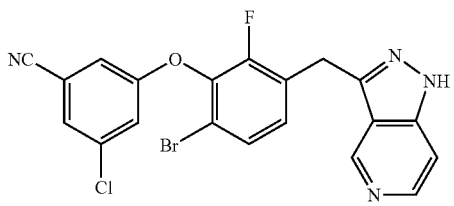

The title compound was prepared in steps 1-3 of example 6 except in step 1 2-chloro-nicotinic acid was replaced with 4-chloro-nicotinic acid (CAS Reg. No. 10177-29-4)

Example 20

3-[6-Bromo-2-fluoro-3-(1H-pyrazolo[3,4-b]pyrazin-3-ylmethyl)-phenoxy]-5-chloro-benzonitrile (I-53)

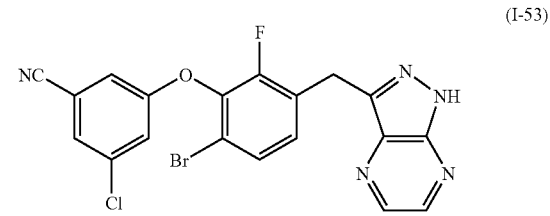

3-[6-Bromo-2-fluoro-3-(1H-pyrazolo[3,4-b]pyrazin-3-ylmethyl)-phenoxy]-5-chloro-benzonitrile (I-53) can be prepared by utilizing the procedures in steps 1-3 of example 6 except in step 1, 2-chloronicotinic acid is replaced by 3-chloro-pyrazinecarboxylic acid (CAS Reg No. 27398-39-6).

Example 21

3-[6-Bromo-2-fluoro-3-(1H-pyrazolo[3,4-c]pyridazin-3-ylmethyl)-phenoxy]-5-chloro-benzonitrile (I-49)

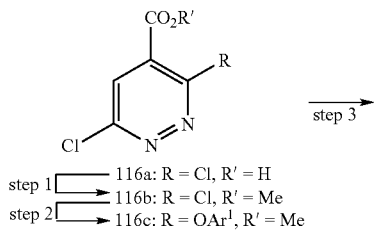

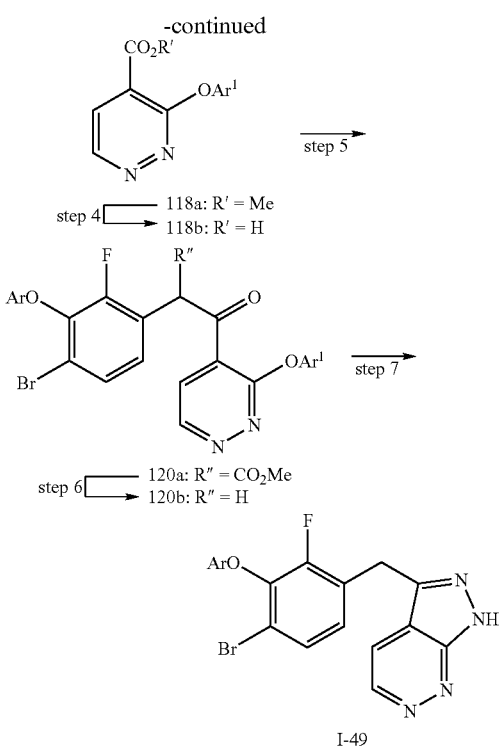

Ar = 3-chloro-5-cyano-phenyl
Ar¹ = 2,4-difluoro-phenyl step 1—To a solution of 3,6-dichloro-4-carboxy-pyridazine (7.5 g, 38.9 mmol, Aldrich) in DCM (30 mL) and MeOH (10 mL) cooled to 0° C. was added a solution of (trimethylsilyl)diazomethane (2.0 M in hexane), slowly via pipette, until a persistent yellow color is observed. After addition was complete, the solvents were removed in vacuo. The crude product was purified by SiO$_2$ chromatography eluting with an EtOAc/hexane gradient (10 to 25% EtOAc) to afford 3.89 g (86%) of 116b as a brown oil that solidifies on standing.

step 2—Sodium hydride (1.53 g, 38.27 mmol) was suspended in dry THF (70 mL) under a N$_2$ atmosphere, cooled to 0° C. and 2,4-difluorophenol (3.31 mL, 34.94 mmol) was added dropwise, via syringe. After the addition was complete the mixture was stirred for 15 min, then the cooling bath was removed for 30 min and finally the solution was again cooled to 0° C. A solution of 116b (6.89 g, 33.28 mmol) in dry THF (20 mL) was added through a cannula. The resulting mixture was stirred at RT overnight and then heated to 50° C. for 3 h. The reaction was cooled to RT and saturated NH$_4$Cl (40 mL) was added followed by water (60 mL). The mixture was thrice extracted with EtOAc, dried (MgSO$_4$), filtered and evaporated. The crude product was purified by SiO$_2$ chromatography eluting with an EtOAc/hexane gradient (10 to 20% EtOAc) to afford 8.15 g (82%) of 116c as a light yellow oil.

step 3—To a solution of 116c (8.15 g, 127.11 mmol) in MeOH (40 mL) was added ammonium formate (8.55 g, 1.1 eq) followed by 10% Pd—C (500 mg). The mixture was heated to 50° C. for 20 min and then to 60° C. for 35 min. The mixture was cooled to RT and filtered through a 2 cm plug of CELITE® which was rinsed well with MeOH. The volatile solvents were evaporated and the residual material partitioned between DCM (80 mL) and H$_2$O. The DCM layer was separated and the aqueous layer extracted twice with DCM and water (80 mL). The combined extracts were dried (MgSO$_4$), filtered and evaporated. The crude product was purified by SiO$_2$ chromatography eluting with an EtOAc/hexane gradient (10 to 50% EtOAc) to afford 5.5 g (76%) of 118a as a semi-viscous yellow oil.

step 4—To a solution of 118a (5 g, 18.78 mmol) in THF (40 mL) and MeOH (10 mL) was added an aqueous solution of LiOH (21.6 mL, 1 M solution). The mixture was stirred for 15 min when the reaction was complete as determined by TLC analysis. The mixture was concentrated and the residue was diluted with H$_2$O (25 mL) and THF (20 mL) and then adjusted to pH 2-3 with 10% HCl. The resulting solid was collected by filtration, washed with water (50 mL) and EtOAc (30 mL) to obtain 4.08 g (86%) of 118b as a white powder.

step 5—To a solution of 118b (605 mg, 2.4 mmol) in DMF (10 mL) was added CDI (410 mg, 2.5 mmol). The mixture was heated to 50° C. under an Ar atmosphere for 1.5 h. The solution was cooled to −10° C. and a solution of 67 (1 g, 2.5 mmol) in DMF (5 mL) was added via syringe. While stirring vigorously, NaH (336 mg, 8.4 mmol) was added in 3 portions over 20 min. The orange solution was stirred for another 10 min and then the cooling bath was removed. The mixture was stirred for 1 h at RT. The reaction mixture was diluted with saturated NH$_4$Cl solution (20 mL), water (30 mL) and EtOAc (50 mL) and agitated. The EtOAc phase was washed brine (50 mL) and the brine solution was extracted with EtOAc (2×30 mL). The combined extracts were dried (MgSO$_4$), filtered and evaporated. The crude product was purified by SiO$_2$ chromatography eluting with an EtOAc/hexane gradient (40 to 100% EtOAc) to afford 685 mg (45%) of 120a as a orange foam.

step 6—To a solution of 120a (670 mg, 1.06 mmol) in DMSO (8 mL) was added water (0.4 mL) and brine (10 drops). The mixture was heated to 145° C. (oil bath temperature) under Ar atmosphere for 10 min. The solution was cooled to RT and water (60 mL), EtOAc (30 mL) and Et$_2$O (30 mL) were added. The mixture was agitated and NaCl (2 gm) was added. The mixture was again agitated and the organic phase was collected, washed with brine solution (50%) and the brine solution back-extracted with EtOAc/Et$_2$O (1:1, 2×50 mL). The combined organic phases were dried (MgSO$_4$), filtered and evaporated. The crude product was purified by preparative TLC developing with 40% EtOAc/hexanes to afford 380 mg (62%) of 120b as a light yellow foam.

step 7—To a solution of 120b (100 mg, 0.17 mmol) in MeOH (2 mL) was added tert-butyl carbazate (45 mg, 2 eq) followed by glacial HOAc (0.03 mL). The mixture was heated at 60° C. for 5 h and then stirred at RT overnight. The mixture was partitioned between DCM (20 mL) and 5% NaHCO$_3$ (20 mL). The aqueous phase was back-extracted with DCM (2×20 mL) and the combined organic extracts dried (MgSO$_4$), filtered and evaporated. This residue was dissolved in THF (4 mL) in a microwave vial, DBU (0.04 mL, 1.5 equivalents) was added the resulting solution was heated for 10-12 min at 150° C. in microwave. The mixture was partitioned among EtOAc (40 mL), water (30 mL) and saturated aqueous NH$_4$Cl (5 mL). The organic phase was separated and the aqueous phase was back-extracted with EtOAc (2×30 mL). The combined extracts were dried (MgSO$_4$), filtered and evaporated. The crude product was purified by preparative TLC developing with 6% MeOH/DCM to provide 45 mg (58%) of I-49 the product as an off-white powder.

5-[6-Bromo-2-fluoro-3-(1H-pyrazolo[3,4-c]pyridazin-3-ylmethyl)-phenoxy]-isophthalonitrile; trifluoroacetate salt (I-52) was prepared analogously except in step 5, 67 was replaced by R-24.

5-[6-Ethyl-2-fluoro-3-(1H-pyrazolo[3,4-c]pyridazin-3-ylmethyl)-phenoxy]-isophthalonitrile (I-54) was prepared analogously except in step 5, 67 was replaced by R-36.

3-Chloro-5-[6-ethyl-2-fluoro-3-(1H-pyrazolo[3,4-c]pyridazin-3-ylmethyl)-phenoxy]-benzonitrile (I-55) was prepared analogously except in step 5, 67 was replaced by R-32.

3-Chloro-5-[6-cyclopropyl-2-fluoro-3-(1H-pyrazolo[3,4-c]pyridazin-3-ylmethyl)-phenoxy]-benzonitrile (I-56) was prepared analogously except in step 5, 67 was replaced by R-42a.

5-[6-Cyclopropyl-2-fluoro-3-(1H-pyrazolo[3,4-c]pyridazin-3-ylmethyl)-phenoxy]-isophthalonitrile (I-57) was prepared analogously except in step 5, 67 was replaced by R-41.

Example 22

3-[6-Bromo-2-fluoro-3-(6-methyl-7-oxo-4,5,6,7-tetrahydro-1H-pyrazolo[3,4-c]pyridin-3-ylmethyl)-phenoxy]-5-chloro-benzonitrile (I-51)

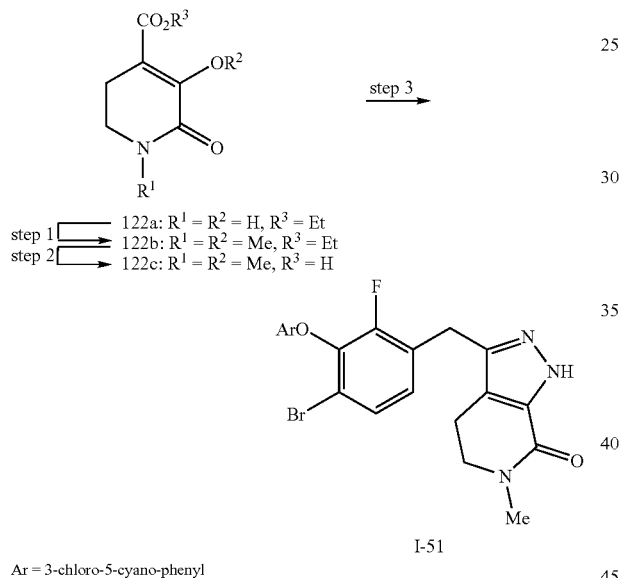

Ar = 3-chloro-5-cyano-phenyl

The starting material 122a was prepared by the method disclosed by S. D. Barrett et al., Org. Prep Proc. Int. 1997 29(3):330-334.

steps 1 & 2—Iodomethane (0.75 mL, 2 equiv) was slowly added to solution of 122a (1.10 g, 5.94 mmol) and KOtBu (1.34 g, 2 equiv) in toluene (30 mL). After stirring overnight (18 h) the thick mixture was quenched with 6M HCl (30 mL), diluted with water and extracted with EtOAc. The organic layers were washed with brine, dried (MgSO$_4$) and concentrated. The residue obtained was re-dissolved in DCM (13 mL) and MeOH (13 mL) at 0° C. To this solution was carefully added trimethylsilyl diazomethane (5 mL, 2M hexanes, 4 equiv) over 10 min. The reaction mixture was quenched with HOAc and concentrated in vacuo. The enol ester 122b was purified by SiO$_2$ chromatography eluting with an EtOAc/DCM gradient (25 to 50% EtOAc) to afford 0.250 g (20%) of 122b. A portion of this material (200 mg, 0.94 mmol) was dissolved in THF (9 mL) and a solution LiOH.H$_2$O (47 mg, 1.2 equiv) in H$_2$O (3 mL) was added. After stirring overnight the solution was adjusted to pH1 with 10% HCl and extracted with EtOAc. The combined organic layers were washed with brine, dried (MgSO$_4$), and concentrated to afford 120 mg (69%) of 122c.

5-Methoxy-1-methyl-6-oxo-1,2,3,6-tetrahydro-pyridine-4-carboxylic acid (122c) was converted to I-51 using the procedure described in steps 3-5 of example 9. In this case no displacement of the methoxy substituent by imidazole was observed.

Example 23

3-[6-Bromo-2-fluoro-3-(6-methyl-7-oxo-4,5,6,7-tetrahydro-1H-pyrazolo[3,4-c]pyridin-3-ylmethyl)-phenoxy]-5-chloro-benzonitrile (I-50)

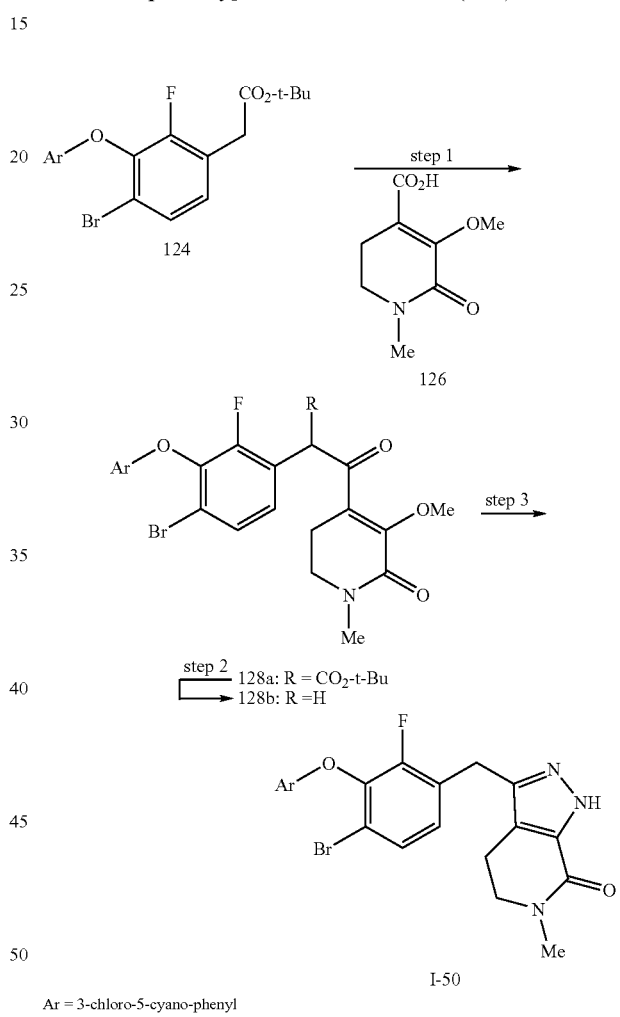

Ar = 3-chloro-5-cyano-phenyl steps 1 & 2—CDI (0.116 g, 1.1 equiv) was added in one portion to a solution of acid 126 (0.12 g, 0.65 mmol) in DMF (1.1 mL). After heating for 30 min at 50° C. the solution was cooled to 0° C. and a solution of 124 (0.315 g, 1.1 equiv) in DMF (2.3 mL) was added. Sodium hydride (0.088 g, 60% in oil, 3.4 equiv) was slowly added in one portion and the reaction mixture was allowed to warm to RT over 2 h. The mixture was then re-cooled to 0° C., quenched with saturated NH$_4$Cl, diluted with water and extracted with EtOAc. The combined organic extracts were washed with brine, dried (MgSO$_4$), and concentrated. The residue obtained was re-dissolved in DCM (6.5 mL) and treated with TFA (3.25 mL) for 3 h. The reaction mixture was concentrated and the residue purified by SiO$_2$ chromatography eluting with a MeOH/DCM gradient (1 to 5% MeOH) to afford 0.180 g (37%) of 128b.

step 3—Hydrazine (53 µL, 5 equiv) was slowly added to a solution of 128b (0.170 g, 0.335 mmol) in 1,4-dioxane (3.4 mL) at RT. The reaction was then heated to 50° C. for 3 h, cooled to RT and concentrated. The crude product was purified by SiO$_2$ chromatography eluting with an EtOAc/hexane gradient (40 to 100% EtOAc) to afford 0.060 g (37%) of I-50.

Example 24

3-Chloro-5-[6-difluoromethyl-2-fluoro-3-(1H-pyrazolo[3,4-c]pyridazin-3-ylmethyl)-phenoxy]-benzonitrile (I-60)

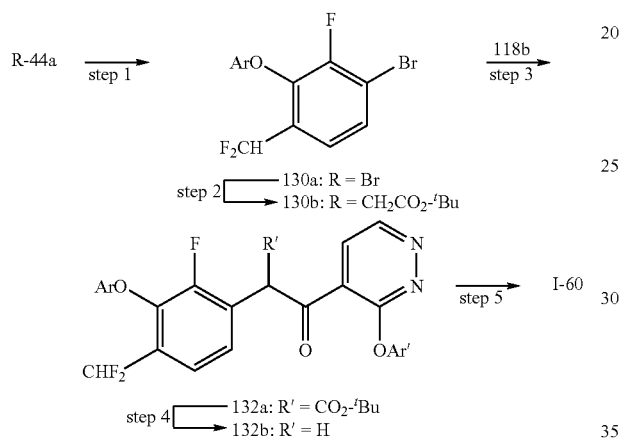

Ar = 3-chloro-5-cyano-phenyl; Ar' = 2,4-fluoro-phenyl step 1—To a solution of R-44a (3.2 g, 9.04 mmol) in DCM (12 mL) was added sequentially DAST (3.2 g, 2.2 eq) and EtOH (0.02 g, 0.05 eq) and the reaction mixture was stirred for 16 h. The reaction mixture was partitioned between aqueous NaHCO$_3$ and DCM. The organic layer was washed sequentially with water and brine, dried (Na$_2$SO$_4$), filtered and evaporated to afford 1.9 g (56%) of 130a.

step 2—To a solution of 130a (1.9 g, 5.045 mmol) and Pd(0)[P(tert-Bu)$_3$]$_2$ (0.39 g, 0.15 eq) in dioxane (30 mL) at RT was added 2-tert-butoxy-2-oxoethylzinc chloride (25 mL; 0.5M solution in ether) and the resulting solution was stirred at RT for 6 h. The reaction was partitioned between aqueous HCl and EtOAc. The organic layer was washed sequentially with water and brine, dried (Na$_2$SO$_4$), filtered and evaporated. The crude product was purified by SiO2 chromatography eluting with an EtOAc/hexane gradient (2-12% EtOAc) to afford 0.65 g (30%) of 130b.

step 3—To a solution of 118b (0.088 g, 1.1 eq) and DMF (1 mL) was added CDI (0.06 g, 1.15 eq) and the solution was heated to 50° C. for 1 h. The reaction mixture was cooled to −25° C. and a solution of 130b (0.13 g, 0.316 mmol) and DMF (1 mL) and NaH (0.04 g, 3.2 eq) were added. The reaction mixture was slowly warmed to RT and stirred for 6 h. The reaction mixture was partitioned between sat'd aqueous NaHCO$_3$ and EtOAc/hexanes (1:1). The organic layer was washed sequentially with H$_2$O and brine, dried (Na$_2$SO$_4$), filtered and evaporated to afford 0.200 g (98%) of 132a.

step 4—A solution of 132a (0.2 g, 0.31 mmol) and p-TsOH (0.015 g, 0.25 eq) in toluene (2.5 mL) was heated at 130° C. for 2 h. The reaction was cooled, and poured into sodium bicarbonate and extracted with EtOAc. The organic layer was washed sequentially with water and brine, dried (Na$_2$SO$_4$), filtered and evaporated. The crude product was purified by SiO$_2$ chromatography eluting with an EtOAc/hexane gradient (15-50% EtOAc) to afford 0.15 g (89%) of 132b.

step 5—A solution of 132b (0.15 g, 0.274 mmol), p-TsOH (0.10 g, 2 eq) and hydrazine (0.03 mL, 2 eq) in IPA (2 mL) was heated to 80° C. for 16 h. The reaction was cooled to 0° C. and H$_2$O (2.6 mL) was added. The pH of the resulting solution was adjusted to ca 9 with 20% Na$_2$CO$_3$. then further diluted with H$_2$O (5 mL) and warmed up to RT for 1 h. The cloudy mixture was poured into EtOAc and the organic layer washed sequentially with water and brine, dried (Na$_2$SO$_4$), filtered and evaporated. The crude product was purified by SiO$_2$ chromatography eluting with a MeOH/DCM gradient (2.5-10% MeOH). The recovered material was triturated with EtOAc/hexanes to afford 0.040 g (34%) of I-60.

Example 25

3-Chloro-5-[2-fluoro-6-methanesulfonyl-3-(1H-pyrazolo[3,4-c]pyridazin-3-ylmethyl)-phenoxy]-benzonitrile (I-63)

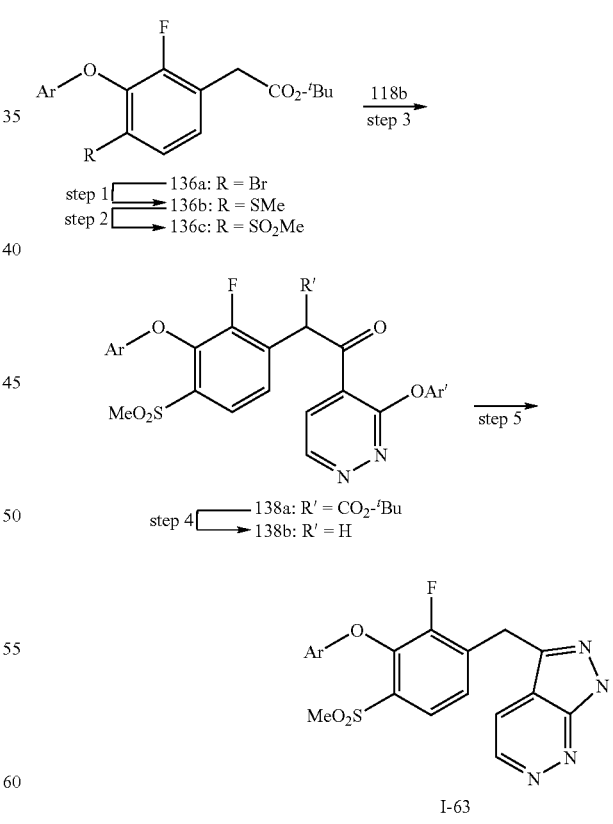

Ar = 3-chloro-5-cyano-phenyl; Ar' - 2,4-difluoro-phenyl step 1—To a solution of 136a (4.03 g, 9.15 mmol) in m-xylene (60 mL) was added K$_2$CO$_3$ (846 mg, 6.12 mmol), Pd$_2$(dba)$_3$ (840 mg, 0.92 mmol), Xantphos (600 mg, 1.04 mmol, CASRN 161265-03-8) and NaSMe (810 mg, 11.56 mmol). The mixture was degassed and then heated to 135° C., under an argon balloon for 20 h. The reaction was cooled to RT and brine (80 mL) was added. The mixture was extracted with EtOAc (80 mL). The aqueous phase was back-extracted with EtOAc (2×70 mL) and dried (MgSO₄), filtered and concentrated in vacuo. The crude product was purified by SiO₂ chromatography eluting with an EtOAc/hexane gradient (5-20% EtOAc) to afford 2.3 of 136b as a yellow oil.

step 2—To a solution of 136b (2.4 g, 5.88 mmol) in MeOH (60 mL) and THF (8 mL) cooled to 0° C. (ice bath) was added dropwise a solution of OXONE® (7.35 g, 11.96 mmol) dissolved in water (22 mL). After the addition was complete the mixture was stirred for 15 min and then the cooling bath was removed. The resulting mixture was stirred overnight and then heated to 50° C. for 4 h. The reaction was cooled to RT and an aqueous solution of sat'd. NaHCO₃ was added dropwise until no further frothing observed. Water (20 mL) was added and the mixture was extracted with EtOAc (40 mL). The extracts were washed with brine (40 mL) and the brine was back-extracted with EtOAc (2×30 mL). The combined the EtOAc extracts were dried (MgSO₄), filtered and concentrated in vacuo to afford 2.5 g of 136c as a light white-yellow solid.

step 3—To a solution of 118b (274 mg, 1.1 mmol) in dry DMF (8 mL) was added CDI (188 mg, 1.2 mmol). The mixture was heated to 50° C. for 2 h then cooled to −10° C. A solution of 136c (500 mg, 1.14 mmol) in DMF (5 mL) was added via syringe. To the cooled mixture was added NaH (152 mg, 3.81 mmol, 60% in mineral oil) over 20 min in three equal portions. After the addition was complete the mixture was stirred for 15 min and then the cooling bath was removed and stirring continued for 1 h. To the solution was carefully added sat'd aqueous NH₄Cl (5 mL), followed by water (30 mL) and EtOAc (40 mL). The mixture was agitated and the EtOAc phase separated. The aqueous phase was back-extracted with EtOAc (2×30 mL). The combined extracts were dried (MgSO₄), filtered and evaporated. The crude product was purified by SiO₂ chromatography eluting with an EtOAc/hexane gradient (50 to 100% EtOAc) to afford 0.256 g of 138a as a yellow foamy solid.

step 4—To a solution of 138a (256 mg, 0.38 mmol) in anisole (5 mL) was added powdered boric anhydride (133 mg). The mixture was heated to 140° C. for 1 h and then cooled to RT. The mixture was concentrated in vacuo. The residue was cooled (ice bath) and partitioned between water (25 mL) and EtOAc (25 mL). The mixture was stirred at RT for 1 h then agitated. The EtOAc phase was washed with brine (25 mL) and the aqueous solution back-extracted with EtOAc (2×20 mL). The combined organic extracts were dried (MgSO₄), filtered, and concentrated to afford 0.215 g of 138b as a light orange-yellow solid.

step 5—To a solution of 138b (215 mg, 0.38 mmol) in IPA (2 mL) was added p-TsOH (144 mg) and hydrazine hydrate (0.04 mL, 85%). The mixture was heated to 80° C. under a N₂ atmosphere for 18 h. The reaction mixture was cooled to RT and water (3.5 mL), 20% aqueous Na₂CO₃ (0.5 mL) then additional water (1.5 mL) were added sequentially. The mixture was stirred for 5 min and then allowed to stand for 1.5 h. The resulting precipitate (65 mg) was collected by filtration. A second crop (130 mg) was recovered from the filtrate. These semi-pure crops were combined and adsorbed on a SiO₂ preparative TLC plate and developed with EtOAc to afford 0.055 g of I-63 as a light white-orange solid.

Example 26

3-[6-Chloro-2-fluoro-3-(1H-pyrazolo[3,4-c]pyridazin-3-ylmethyl)-phenoxy]-5-difluoromethyl-benzonitrile

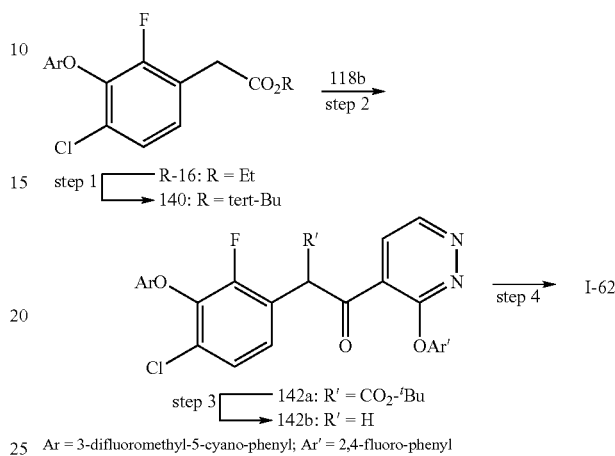

step 1 ┌── R-16: R = Et
       └── 140: R = tert-Bu step 3 ┌── 142a: R' = CO₂-ᵗBu
       └── 142b: R' = H Ar = 3-difluoromethyl-5-cyano-phenyl; Ar' = 2,4-fluoro-phenyl step 1—R-16 was hydrolyzed to the corresponding carboxylic acid with LiOH in aqueous THF by stirring at RT for 3 h. Routine workup afforded the acid which was converted to the tert-butyl ester by stirring a tert-BuOH solution of the acid, Boc-anhydride and DMAP for 2 h. The crude product was purified by SiO₂ chromatography eluting with 5% EtOAc/hexane to afford 140.

step 2—To a solution of 118b (0.485 g, 1.92 mmol) and DMF (9 mL) in a flame-dried flask was added CDI (0.326 g, 2.01 mmol) and the solution was warmed to 50° C. for 65 min then cooled to 0° C. A solution of 140 (0.720 g, 1.75 mmol) in a small amount of DMF was added followed by NaH (0.189 g 4.72 mmol, 50% mineral oil dispersion). The reaction was stirred for 1 h then added to cold sat'd. aqueous NH₄Cl. The solid precipitate was collected, washed with water and dried in vacuo to afford 0.978 g of 142a as a brown solid.

step 3—To a solution of 142a (0.978 g, 1.51 mmol) in anisole (7.5 mL) was added boric anhydride (0.527 g, 7.57 mmol) and the resulting solution was heated to 140° C. for 2 h. The reaction mixture was cooled in an ice bath and the solution partitioned between EtOAc and H₂O. The organic phase was separated, washed with brine, dried, filtered and concentrated in vacuo. The crude product was purified by SiO₂ chromatography eluting with 1% MeOH/DCM to afford 0.580 g of 142b.

step 4—A suspension of 142b (0.580 g, 1.06 mmol) and tosic acid (0.404 g, 2.13 mmol) in IPA (5 mL) was stirred at RT for 20 min. The solution was stirred at 80° C. until the reaction was complete. The reaction mixture was cooled in an ice-bath then H₂O (10.6 mL), 20% aqueous Na₂CO₃ (2 mL) and H₂O (5.3 mL) were added sequentially and the resulting mixture stirred at RT for 1 h. The resulting precipitate was collected, washed with H₂O and dried in vacuo to afford 89 mg of I-62.

3-[6-Chloro-2-fluoro-3-(1H-pyrazolo[3,4-c]pyridazin-3-ylmethyl)-phenoxy]-5-methyl-benzonitrile (I-61) was prepared by procedure in steps 2-4 of the present example from tert-butyl[4-chloro-3-(3-cyano-5-methyl-phenoxy)-2-fluoro-phenyl]-acetate (144). The starting material 144 for the synthesis is prepared by the procedure described for R-1 in the referential example except in step 3, R-3c was replaced by 3-hydroxy-5-methyl-benzonitrile (CASRN 95658-81-4).

Example 27

Heteropolymer HIV Reverse Transcriptase Assay: Inhibitor $IC_{50}$ Determination HIV-1 RT assay was carried out in 96-well Millipore MultiScreen MADVNOB50 plates using purified recombinant enzyme and a poly(rA)/oligo(dT)$_{16}$ template-primer in a total volume of 50 μL. The assay constituents were 50 mM Tris/HCl, 50 mM NaCl, 1 mM EDTA, 6 mM MgCl$_2$, 5 μM dTTP, 0.15 μCi [$^3$H] dTTP, 5 μg/ml poly (rA) pre annealed to 2.5 μg/ml oligo (dT)$_{16}$ and a range of inhibitor concentration in a final concentration of 10% DMSO. Reactions were initiated by adding 4 nM HIV-1 RT and after incubation at 37° C. for 30 min, they were stopped by the addition of 50 μl ice cold 20% TCA and allowed to precipitate at 4° C. for 30 min. The precipitates were collected by applying vacuum to the plate and sequentially washing with 3×200 μl of 10% TCA and 2×200 μl 70% ethanol. Finally, the plates were dried and radioactivity counted in a Packard TopCounter after the addition of 25 μl scintillation fluid per well. $IC_{50}$'s were calculated by plotting % inhibition versus $\log_{10}$ inhibitor concentrations.

Representative $IC_{50}$ data is present below. The $IC_{50}$ of all compounds except I-1 and I-2 were less than 100 nanomoles.

TABLE 2

| Compound | $IC_{50}$ |
|---|---|
| I-6 | 0.0118 |
| I-7 | 0.0076 |
| I-11 | 0.001 |
| I-13 | 0.0086 |
| I-16 | 0.0033 |
| I-28 | 0.0037 |
| I-48 | 0.0009 |

Example 28

Homopolymer HIV Reverse Transcriptase Assay: Inhibitor $IC_{50}$ Determination

HIV-1 RT assay was carried out in 96-well Millipore filtermat NOB50 plates using purified recombinant enzyme and a poly(rA)/oligo(dT)$_{16}$ template-primer in a total volume of 50 μL. The assay constituents were 50 mM Tris/HCl, 50 mM NaCl, 1 mM EDTA, 6 mM MgCl$_2$, 5 μM dTTP, 0.1 μCi [$^3$H] dTTP, 5 μg/ml poly (rA) pre annealed to 2.5 μg/ml oligo (dT)$_{16}$ and a range of inhibitor concentrations in a final concentration of 10% DMSO. Reactions were initiated by adding 5 nM HIV-1 RT and after incubation at 37° C. for 30 min, they were stopped by the addition of 50 μl ice cold 20% TCA and allowed to precipitate at 4° C. for 30 min. The precipitates were collected by applying vacuum to the plate and sequentially washing with 2×200 μl of 10% TCA and 2×200 μl 70% ethanol. Finally the plates were dried and radioactivity counted in a Wallac Microbeta 1450 after the addition of 15 μL scintillation fluid per well. $IC_{50}$'s (TABLE 3) were calculated by plotting % inhibition versus $\log_{10}$ inhibitor concentrations.

TABLE 3

| Compound | $IC_{50}$ |
|---|---|
| I-3 | 0.052 |
| I-5 | 0.055 |

Example 29

Pharmaceutical Compositions

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula I

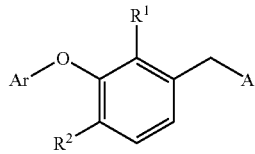

I

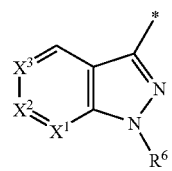

A2 wherein:
A is A-2 wherein $X^2$ and one of $X^1$ and $X^3$ are N and the other of $X^1$ and $X^3$ is $CR^3$;
$R^1$ is fluorine or hydrogen;
$R^2$ is hydrogen, halogen, $C_{1-6}$ alkyl, $C_{3-7}$ cycloalkyl, $C_{1-6}$ haloalkyl, $C_{1-6}$ alkoxy, or $C_{1-6}$ alkylsulfonyl;
Ar is phenyl substituted with one to three groups independently selected in each occurrence from the group consisting of hydrogen, halogen, cyano, $C_{1-6}$ alkyl, $C_{1-6}$ alkoxy, $C_{1-6}$ haloalkyl and $C_{3-7}$ cycloalkyl;
$R^3$ is independently selected in each occurrence from the group consisting of:
   (i) hydrogen,
   (ii) hydroxy,
   (iv) halogen,
   (v) $NR^{4a}R^{4b}$,
   (vi) $C_{1-6}$ acylamino,
   (vii) $C_{1-6}$ alkylsulfonylamino,
   (viii) cyano,
   (ix) nitro,
   (x) $NHNH_2$; and
   (xi) phenyl optionally substituted with one to three substituents independently selected from the group consisting of halogen, $C_{1-6}$ alkyl, $C_{1-6}$ alkoxy, cyano, intro;
$R^{4a}$ and $R^{4b}$ are independently hydrogen or $C_{1-6}$ alkyl;
$R^5$ is hydrogen or $C_{1-3}$ alkyl;
$R^6$ is hydrogen or $C_{1-6}$ alkyl; and,
pharmaceutically acceptable salt thereof.

2. A compound according to claim 1 wherein A is A2, $X^1$ and $X^2$ are N and $X^3$ is $CR^3$.

3. A compound according to claim 2 wherein $R^1$ is fluoro; $R^2$ is $C_{1-6}$ alkyl, $C_{1-6}$ alkoxy, or halogen; Ar is 3-cyano-phenyl optionally substituted with one or two groups independently selected from halogen, cyano and $C_{1-6}$ haloalkyl; and $R^6$ is hydrogen.

4. A compound according to claim 3 wherein Ar is 3-cyano-phenyl optionally substituted with halogen, cyano or $C_{1-6}$ haloalkyl meta to the cyano substituent.

5. A compound according to claim 4 wherein $R^2$ is bromo or chloro.

6. A compound according to claim 1 which compound is selected from the group consisting of:

- 3-chloro-5-[6-chloro-2-fluoro-3-(1H-pyrazolo[3,4-c]pyridazin-3-ylmethyl)-phenoxy]-benzonitrile;
- 3-[6-bromo-2-fluoro-3-(1H-pyrazolo[3,4-c]pyridazin-3-ylmethyl)-phenoxy]-5-chloro-benzonitrile:
- 5-[6-bromo-2-fluoro-3-(1H-pyrazolo[3,4-c]pyridazin-3-ylmethyl)-phenoxy]-isophthalonitrile; trifluoroacetate salt;
- 5-[6-ethyl-2-fluoro-3-(1H-pyrazolo[3,4-c]pyridazin-3-ylmethyl)-phenoxy]-isophthalonitrile;
- 3-chloro-5-[6-ethyl-2-fluoro-3-(1H-pyrazolo[3,4-c]pyridazin-3-ylmethyl)-phenoxy]-benzonitrile;
- 3-[6-chloro-2-fluoro-3-(1H-pyrazolo[3,4-c]pyridazin-3-ylmethyl)-phenoxy]-5-difluoromethyl-benzonitrile; and,
- 3-chloro-5-[2-fluoro-6-methanesulfonyl-3-(1H-pyrazolo[3,4-c]pyridazin-3-ylmethyl)-phenoxy]-benzonitrile.

7. A pharmaceutical composition comprising a therapeutically effective quantity of a compound according to claim 1 and at least one carrier, excipient or diluent.

* * * * *